US008898910B2

(12) United States Patent
Ichiyanagi et al.

(10) Patent No.: US 8,898,910 B2
(45) Date of Patent: Dec. 2, 2014

(54) CUTTER

(75) Inventors: Masao Ichiyanagi, Gifu (JP); Akira Takahashi, Aichi (JP)

(73) Assignee: Feather Safety Razor Co., Ltd., Osaka-shi (JP)

( * ) Notice: Subject to any disclaimer, the term of this patent is extended or adjusted under 35 U.S.C. 154(b) by 310 days.

(21) Appl. No.: 13/580,795

(22) PCT Filed: Feb. 8, 2011

(86) PCT No.: PCT/JP2011/052569
§ 371 (c)(1),
(2), (4) Date: Aug. 23, 2012

(87) PCT Pub. No.: WO2011/108337
PCT Pub. Date: Sep. 9, 2011

(65) Prior Publication Data
US 2012/0311869 A1 Dec. 13, 2012

(30) Foreign Application Priority Data

Mar. 4, 2010 (JP) .................... PCT/JP2010/053538

(51) Int. Cl.
*B26B 3/06* (2006.01)
*A61B 17/3213* (2006.01)
(52) U.S. Cl.
USPC .............................. 30/162; 30/151; 606/167
(58) Field of Classification Search
USPC ......... 30/2, 350, 151, 162, 152; 606/167, 180
See application file for complete search history.

(56) References Cited

U.S. PATENT DOCUMENTS

| 4,617,738 A | 10/1986 | Kopacz |
| 4,922,614 A | 5/1990 | Machida |
| 5,496,340 A | 3/1996 | Abidin et al. |

(Continued)

FOREIGN PATENT DOCUMENTS

| EP | 0 162 186 A1 | 11/1985 |
| JP | 60 21745 | 2/1985 |

(Continued)

OTHER PUBLICATIONS

Office Action and Search Report issued on Apr. 23, 2014 in the corresponding Chinese Patent Application No. 201180012220.0 (with English Translation).

(Continued)

*Primary Examiner* — Sean Michalski
(74) *Attorney, Agent, or Firm* — Oblon, Spivak, McClelland, Maier & Neustadt, L.L.P.

(57) ABSTRACT

A cutter formed by detachably attaching a replaceable blade to a cutter body. The cutter body can include a main body block and slide block. The main body block includes a main body supporting section supporting the replaceable blade back face, and a main body connecting section connecting with the replaceable blade from the front face side. The slide block includes a rear side supporting section supporting the replaceable blade back face, a slide connecting section connecting with and retracting the replaceable blade toward the rear side, and a back side protruding section protruding on the back side in a thickness direction. When attached, the replaceable blade elastically deforms to curve in the thickness direction, the slide block presses toward a main body block side in the thickness direction by elastic force of the replaceable blade, and the back side protruding section engages with a main body block engaged section.

14 Claims, 43 Drawing Sheets

(56) References Cited

U.S. PATENT DOCUMENTS

| | | |
|---|---|---|
| 5,527,329 A | 6/1996 | Gharibian |
| 5,620,454 A | 4/1997 | Pierce et al. |
| 5,662,669 A | 9/1997 | Abidin et al. |
| 5,752,968 A | 5/1998 | Jolly et al. |
| 5,792,162 A | 8/1998 | Jolly et al. |
| 5,827,309 A | 10/1998 | Jolly et al. |
| 5,868,771 A | 2/1999 | Herbert et al. |
| 5,919,201 A | 7/1999 | Carter et al. |
| 5,938,675 A | 8/1999 | Gharibian |
| 5,938,676 A | 8/1999 | Cohn et al. |
| 5,941,892 A | 8/1999 | Cohn et al. |
| 6,053,929 A | 4/2000 | Cohn et al. |
| 6,216,868 B1 | 4/2001 | Rastegar et al. |
| 6,626,925 B2 | 9/2003 | Newman et al. |
| 6,629,985 B1 | 10/2003 | Kiehne |
| 7,207,999 B2 | 4/2007 | Griffin et al. |
| 2006/0095057 A1 | 5/2006 | Yi et al. |
| 2006/0100650 A1 | 5/2006 | Kiehne |
| 2006/0212058 A1 | 9/2006 | Djordjevic et al. |
| 2007/0255298 A1 | 11/2007 | Djordjevic et al. |
| 2007/0265651 A1 | 11/2007 | Yi et al. |
| 2013/0245656 A1* | 9/2013 | Austria .......... 606/167 |

FOREIGN PATENT DOCUMENTS

| | | |
|---|---|---|
| JP | 60 227747 | 11/1985 |
| JP | 63 172411 | 11/1988 |
| JP | 1 155412 | 10/1989 |
| JP | 2 82315 | 6/1990 |
| JP | 11 318913 | 11/1999 |
| JP | 2003 339722 | 12/2003 |
| JP | 2007 61429 | 3/2007 |
| JP | 2007 159938 | 6/2007 |

OTHER PUBLICATIONS

International Search Report Issued Mar. 8, 2011 in PCT/JP11/52569 Filed Feb. 8, 2011.

Supplementary European Search Report issued May 19, 2014 in Patent Application No. 11750450.6.

Extended European Search Report issued Feb. 17, 2014 in Patent Application No. 11750450.6.

* cited by examiner (A)

(B)

CUTTER

TECHNICAL FIELD

The present invention relates to a cutter formed by detachably attaching a replaceable blade to a cutter body.

BACKGROUND ART

As a cutter used for a knife for medical use, a knife for pathologic use, or razors for facial shaving or haircut, there is a cutter formed by detachably attaching a replaceable blade to a cutter body.

In such a cutter, the replaceable blade is attached to the cutter body by inserting the replaceable blade into a groove section provided in the cutter body. Then, the replaceable blade can be replaced after a predetermined number of times or a period of use.

Various efforts are made to such a blade-replaceable type cutter in order to facilitate easy replacement of the replaceable blade. For example, a cutter described in patent document 1 includes an engaging member capable of sliding with respect to a cutter body, and the replaceable blade can be attached to and detached from the cutter body by using a fore end section of the cutter body and the engaging member such that an opening section provided in the replaceable blade is engaged and being pulled in a longitudinal direction.

Further, as a cutter in patent document 2, there is a type in which a replaceable blade cartridge composed of a replaceable blade and a protection cover can be detachably attached to a cutter body.

PRIOR ART DOCUMENT

Patent Documents

Patent Document 1: Japanese Patent Application Publication No. 2007-61429
Patent Document 2: U.S. Pat. No. 7,207,999

SUMMARY OF THE INVENTION

Problem to be Solved by the Invention

However, in the cutter of patent document 1, a coil spring is used for retaining the engaging member on a rear end side in the longitudinal direction so that the replaceable blade does not fall off. That is, the replaceable blade is retained on the cutter body by the engaging member being pulled to the rear end side in the longitudinal direction by a biasing force of the coil spring. Due to this, the coil spring needs to be contained in the cutter body, which causes problems that the configuration thereof becomes complicated, and the number of components increases.

Further, the cutter of patent document 2 is capable of replacing the replaceable blade cartridge composed of a replaceable blade and a protection cover, as described above. That is, not only the replaceable blade but also the replaceable blade cartridge composed of the replaceable blade and the protection cover is a disposable component. In this configuration, a cost (running cost) in a long-term use becomes high despite being a blade-replaceable type, which is not economical.

The present invention has been made in view of the foregoing problem, and aims to provide a cutter in which only the replaceable blade can be replaced, and that has less number of components, and a simple configuration.

Means of Solving the Problem

The first aspect of the present invention is a cutter formed by detachably attaching a replaceable blade to a cutter body, wherein the replaceable blade has flexibility in a thickness direction, the cutter body is composed of a main body block and a slide block retained in the main body block so as to be able to move in a longitudinal direction of the cutter, the main body block includes a main body supporting section that supports a back face of the replaceable blade, and a main body connecting section that connects with the replaceable blade from a front face side, the slide block includes a rear-side supporting section that supports the back face of the replaceable blade at a farther rear side from the main body supporting section, a slide connecting section that connects with the replaceable blade so as to retract the replaceable blade toward the rear side, and a back side protruding section that protrudes on a back side in the thickness direction, and in an attached state in which the replaceable blade is attached to the cutter body, the replaceable blade is elastically deformed to curve in the thickness direction, the slide block is pressed toward the back side in the thickness direction by an elastic force of the replaceable blade, and the back side protruding section is engaged with an engaged section provided in the main body block.

Effects of the Invention

In the cutter of the present invention, when the replaceable blade is to be attached to the cutter body, a blade replacing state in which the replaceable blade can be detachably attached is realized by moving the slide block forward, and the replaceable blade is temporarily connected with the main body connecting section and the slide connecting section. Then, the main body connecting section and the slide connecting section pull the replaceable blade to both sides in the longitudinal direction by causing the slide block to retract rearward. Due to this, the attached state in which the replaceable blade is attached to the cutter body can be realized.

Further, contrary to the above, the replacement of the replaceable blade becomes easily performed by forcingly moving the slide block forward from the attached state to realize the blade replacing state.

Further, in the attached state, the replaceable blade is elastically deformed to curve in the thickness direction. Moreover, the slide block is pressed toward the main body block side in the thickness direction by the elastic force (restoring force) of the replaceable blade, and the back side protruding section is engaged with the engaged section provided in the main body block. Due to this, the slide block is restricted to move forward, and the attached state is maintained.

That is, in the cutter of the present invention, the slide block can be engaged with the main body block by the elastic force of the replaceable blade. According to this, in the attached state, no additional member needs to be provided for restricting the slide block to move forward. That is, a member dedicated to restricting the slide block to move forward is not necessary.

Due to this, the number of components can be decreased, and the configuration thereof can be simplified.

As described above, according to the present invention, a replacement of only the replaceable blade is enabled, and a blade with less number of components and simple configuration can be provided.

MODES TO CARRY OUT THE INVENTION

Figure 1:
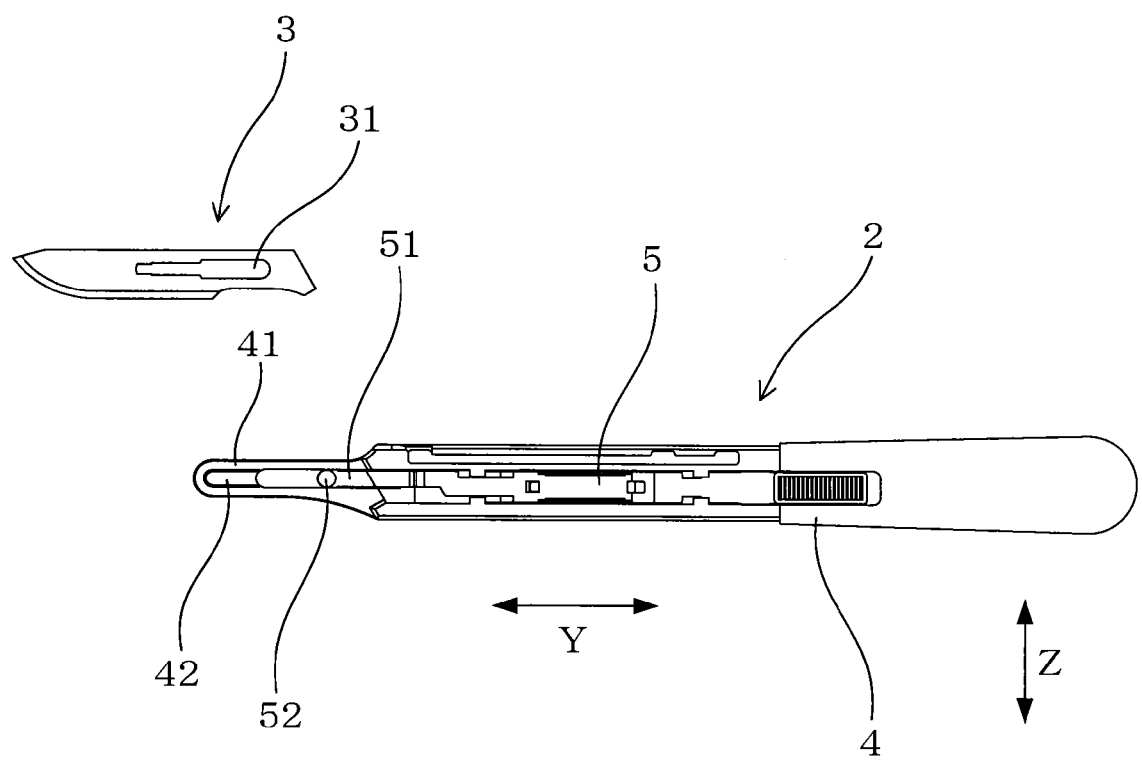
FIG. 1 is a front view of a replaceable blade and a cutter body in a first embodiment.
Figure 2:
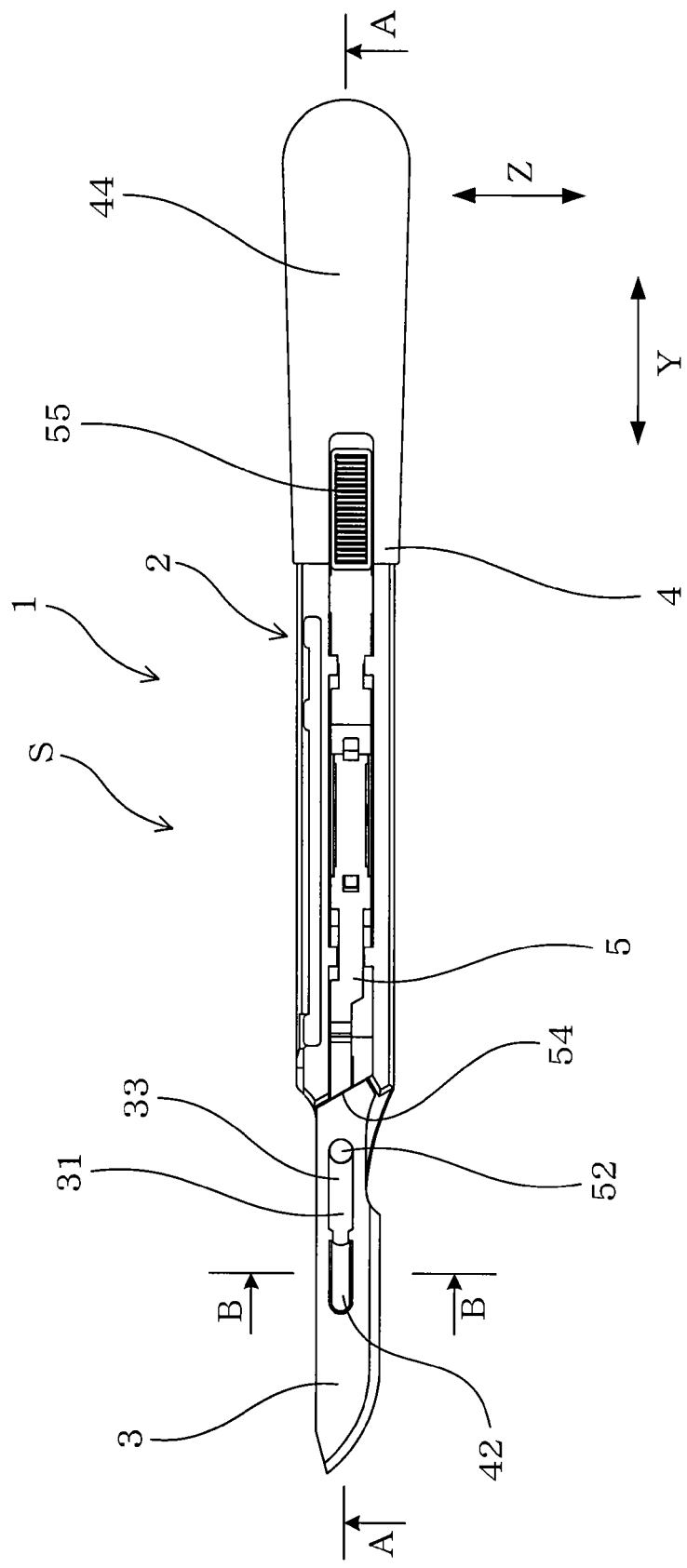
FIG. 2 is a front view of a cutter of the first embodiment.

The cutter according to the present invention may be used for example as a knife for medical use, a knife for pathologic use, or razors for facial shaving or haircut.

Further, in the attached state, it is preferable that the rear-side supporting section protrudes farther than the main body supporting section toward a protruding direction of the rear-side connecting section.

In this case, the replaceable blade that is connected with the main body connecting section and supported by the main body supporting section and the rear-side supporting section at its one main face can more easily be curved protrudingly toward the main body supporting section and the rear side supporting section. Due to this, the slide block can surely be pressed toward the main body block by the elastic force of the replaceable blade so as to engage the back face protruding section with the engaged section.

Further, it is preferable that a cylindrical dual-purposed stopper/cover mounted to the main body block so as to be slidable in the longitudinal direction and opened at both ends in the longitudinal direction is provided, the dual-purposed stopper/cover is capable of being locked at three positions including a foreside position in which the replaceable blade is covered, a rear-side position in which the replaceable blade is significantly exposed, and an intermediate position between the foreside position and the rear-side position, and the dual-purposed stopper/cover restricts a movement of the slide block with respect to the main body block when it is locked at the rear-side position.

In this case, in the attached state, since the dual-purposed stopper/cover covers the replaceable blade when the dual-purposed stopper/cover is locked at the foreside position, user's safety can be secured, and damage to the replaceable blade can be prevented.

Further, in using the cutter, by positioning the dual-purposed stopper/cover at the rear-side position, the movement of the slide block can be restricted. Due to this, the use of the cutter can smoothly be performed.

Further, by locking the dual-purposed stopper/cover at the intermediate position and moving the slide block forward, replacement of the replaceable blade can easily be performed.

Further, it is preferable that the dual-purposed stopper/cover includes a heightwise flat spring at one end in a height direction which is perpendicular to the longitudinal direction and the thickness direction, and a claw section at a free end of the heightwise flat spring, the heightwise flat spring being biased toward an opposite side from the main body block, and the claw section being formed toward an inner side in the thickness direction, the main body block includes a slide groove section, formed in the longitudinal direction and a foreside connecting groove, an intermediate connecting groove, and a rear-side connecting groove respectively formed toward an outer side in the height direction from the slide groove section at three positions in the longitudinal direction, and the claw section is slidably arranged in the slide groove section, and the dual-purposed stopper/cover can be locked at the foreside position, the intermediate position, or the rear-side position by connecting the claw section with the foreside connecting groove, the intermediate connecting groove, or the rear-side connecting groove, respectively.

In this case, the dual-purposed stopper/cover can easily be moved and locked among the foreside position, the intermediate position, and the rear-side position.

Further, it is preferable that a thicknesswise flat spring biased toward the thickness direction is fixed to the slide block, the thicknesswise flat spring being elevated toward an outer side in the thickness direction, an elevation of which increases from a rear end side toward a fore end side, and in the attached state, a fore end section of the thicknesswise flat spring contacts with a contacted section provided in the main body block so that the slide block is prevented from moving forward with respect to the main body block.

In this case, the movement of the slide block in the attached state can more surely be prevented. Further, if the thicknesswise flat spring is pressed while being tilted with its side down, the contact with the contacted section can easily be released, and the slide block can be moved forward.

Further, it may be configured such that a flat spring stopper capable of elastically deforming in the thickness direction is fixed to the slide block, the flat spring stopper includes a stopper protruding part that protrudes in a height direction perpendicular to the longitudinal direction and the thickness direction, and in the attached state, the stopper protruding part contacts with a stopper connection section provided in the main body block so that the slide block is prevented from moving forward with respect to the main body block.

In this case also, the movement of the slide block in the attached state can more surely be prevented. Further, by elastically deforming the flat spring stopper in the thickness direction, the connected state of the stopper protruding part with respect to the stopper connecting section can easily be ended. Due to this, the slide block is allowed to move forward with respect to the main body block.

Further, it is preferable that the flat spring stopper includes a back side connecting part capable of deforming in the height direction, and the rear side connecting part is capable of being connected with a thicknesswise connecting part provided in the main body block from a back face side.

In this case, in a state where the replaceable blade is taken off of the cutter body, the slide block can be prevented from falling off of the main body block. For example, in taking off the replaceable blade for storing or washing the cutter body, the slide block can be prevented from being taken off of the main body block. Due to this, handling of the cutter body becomes easy.

Further, it is preferable that a spring-integrated cover is provided which includes a cylindrical cover main body mounted with respect to the main body block so as to be slidable in the longitudinal direction and opened at both ends in the longitudinal direction, a flat spring section extending in the longitudinal direction and capable of elastically deforming in the thickness direction, and a lock claw provided at a movable end of the flat spring section, the cover main body, the flat spring section, and lock claw being integrally formed by one metal plate, wherein the main body block includes a foreside connecting concave section, a rear-side connecting concave section, and an intermediate connecting concave section, respectively concaved in the thickness direction at three positions in the longitudinal direction, and the spring-integrated cover is capable of being locked at a foreside position in which the replaceable blade is covered, a rear-side position in which the replaceable blade is significantly exposed, and an intermediate position between the foreside position and the rear-side position by connecting the lock claw with the foreside connecting concave section, the rear-side connecting concave section, or the intermediate connecting concave section, respectively.

In this case, in the attached state, since the spring-integrated cover covers the replaceable blade by locking the spring-integrated cover at the foreside position, user's safety can be secured, and damage to the replaceable blade can be prevented. Further, the spring-integrated cover includes the flat spring section and the lock claw, and the main body block includes the foreside connecting concave section, the rear-side connecting concave section, and the intermediate connecting concave section. Due to this, the spring-integrated cover can easily and surely be fixed to the cutter body at one of the foreside position, the rear-side position, and the intermediate position. Further, the spring-integrated cover is formed by integrally forming the cover main body, the flat spring section and the lock claw by one metal plate. Due to this, the number of components can be reduced, and a cost of the cutter can be cut down.

Further, it is preferable that the spring-integrated cover includes a stopper releasing part that presses the flat spring stopper, in a state the cover being locked at the intermediate position with respect to the main body block, to elastically deform the flat spring stopper in the thickness direction so that the stopper protruding part disconnects from the stopper connecting section.

In this case, when the spring-integrated cover is locked at the intermediate position, the replaceable blade can easily be replaced.

Further, it is preferable that the replaceable blade includes an opening section that penetrates the replaceable blade in the thickness direction, the main body connecting section protrudes on a foreside in the thickness direction from the main body supporting section, and is inserted in the opening section to make contact with a fore end of the opening section in the attached state, and the slide connecting section protrudes on the foreside in the thickness direction from the rear-side supporting section, and is inserted in the opening section to make contact with a rear end of the opening section in the attached state.

In this case, the replaceable blade can easily and surely be connected by the main body connecting section and the slide connecting section, and the attached state can easily be obtained.

Further, in this case, the replaceable blade can be attached to the cutter body as below, for example. Firstly, the slide block is moved forward to realize the blade replacing state, and the main body connecting section and the slide connecting section are inserted into the opening section of the replaceable blade. Then, the slide block is moved rearward, whereby the main body connecting section is caused to make contact with the fore end of the opening section of the replaceable blade, and the slide connecting section is caused to make contact with the rear end of the opening section of the replaceable blade. Due to this, the attached state in which the replaceable blade is attached to the cutter body can easily be obtained.

Further, it is preferable that one of the slide block and the main body block includes a heightwise elastic member biased toward an opposing side in a height direction perpendicular to the longitudinal direction and the thickness direction, in using the blade, the replaceable blade is configured to be supported at three points including a lower face of the slide connecting section, an upper face of a rear end section of the main body connecting section and a lower face of a fore end section of the main body connecting section at the opening section by the slide block being pressed toward a lower side with respect to the main body block by a biasing force of the heightwise elastic member and the slide connecting section pressing the rear end section of the opening section toward the lower side, and the lower side is a side in the height direction on which a blade edge of the replaceable blade is formed, and the upper side is an opposite side from the lower side.

In this case, in the attached state, looseness in the height direction between the replaceable blade and the cutter body is effectively prevented. Especially, by supporting the replaceable blade at the three positions at the opening section, namely, the lower face of the slide connecting section, the upper face of the rear end section of the main body connecting section and the lower face of the fore end section of the main body connecting section, the replaceable blade is retained in an attitude with which a fore end of the replaceable blade 3 does not point upward any more. An upward counterforce that is exerted on a blade end while the blade being used can be resisted in this state, and a displacement of the replaceable blade can more effectively be prevented.

Further, it is preferable that, one of the main body block and the slide block on which the heightwise elastic member is not formed includes a foreside pressure-contact section that is capable of making a pressurized contact with the heightwise elastic member in the height direction in a blade replacing state in which the slide block is moved forward with respect to the main body block, and the movement of the slide block with respect to the main body block is restricted by the heightwise elastic member making a pressurized contact with the foreside pressure-contact section.

In this case, since the blade replacing state can easily be retained, the replacement of the replaceable blade can easily be performed.

Further, it is preferable that the opening section is composed of a fore end side opening section and a rear end side opening section, the fore end side opening section being formed on the foreside of the opening section and having a relatively small up and down width in the height direction perpendicular to the longitudinal direction and the thickness direction, and the rear end side opening section being continuously formed on the rear side of the fore end side opening section and having a larger up and down width than the fore end side opening section, the main body connecting section includes a head section whose up and down width in the height direction is smaller than the rear end side opening section and larger than the fore end side opening section, slit groove sections that are cut from both sides in the height direction are provided between the head section and the main body supporting section, and the replaceable blade is configured to connect with the slit groove sections at an outer periphery of the fore end side opening section.

In this case, the replaceable blade can easily be attached to the cutter body, and a stable attached state can be realized.

Further, in this case, the replaceable blade can be attached to the cutter body as below, for example. Firstly, the cutter body is put into the blade replacing state, and the main body connecting section and the slide connecting section are inserted into the rear end side opening section of the replaceable blade. Then, the slide block is moved rearward, whereby the main body connecting section is caused to connect with the fore end side opening section of the replaceable blade, and the slide connecting section is caused to make contact with the rear end of the rear end side opening section. Due to this, the attached state can easily and surely be obtained.

Further, it is preferable that the main body supporting section has a larger up and down width than the rear end side opening section.

In this case, the replaceable blade can easily and stably be attached to the cutter body.

Further, it is preferable that the slide block includes a rear-side opposing face that opposes a rear end of
the replaceable blade in the longitudinal direction, and the rear-side opposing face presses the replaceable blade toward a foreside by the rear-side opposing face making contact with the rear end of the replaceable blade when the slide block is moved forward with respect to the main body block.

In this case, the connection with the main body connecting section can easily be disconnected by moving the replaceable blade forward by moving the slide block forward. Due to this, the replacement of the replaceable blade can more easily be performed.

Further, it is preferable that the slide block is diverged into a center part and a pair of diverged parts at a position on a foreside than the back side protruding section, the center part including the rear-side supporting section and the slide connecting section and the pair of diverged parts being arranged at both sides of the center part in a height direction perpendicular to the longitudinal direction and the thickness direction, and the rear-side opposing face is formed at fore ends of the pair of diverged parts.

In this case, the rear-side opposing face can more stably be made to contact the rear end of the replaceable blade. That is, since the pair of diverged parts is formed at different portions from the center part, the fore ends of the diverged parts can be processed as end surfaces. Due to this, by forming the rear-side opposing face at the fore ends of these diverged parts, the rear-side opposing face can be a face that is parallel to the thickness direction of the replaceable blade. As a result, the rear-side opposing face can stably be made to contact the back end of the replaceable blade, so that the replaceable blade can stably be pushed out foreside when the slide block is moved forward with respect to the main body block.

Further, it is preferable that the rear end of the replaceable blade and the rear-side opposing face are formed obliquely with respect to the longitudinal direction when viewed from the thickness direction.

In this case, an error in the orientation of the replaceable blade to be attached can be prevented.

EMBODIMENTS

First Embodiment

A cutter according to an embodiment of the present invention will be explained with reference to FIG. 1 to FIG. 22.

As shown in FIG. 1 to FIG. 6, a cutter 1 of the present embodiment is a knife for medical use formed by detachably attaching a replaceable blade 3 to a cutter body 2.

Figure 7:
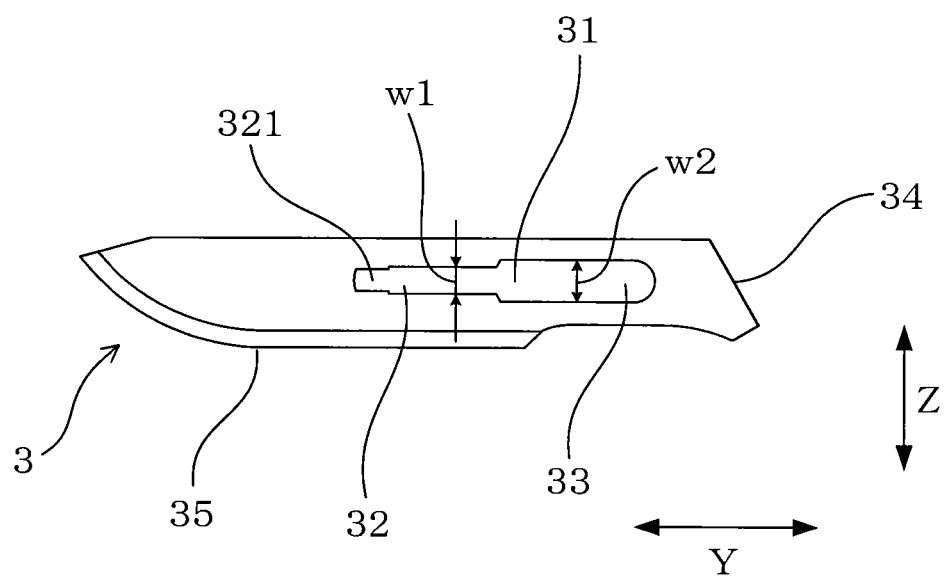
FIG. 7 is a front view of the replaceable blade of the first embodiment.

The replaceable blade 3 has flexibility in a thickness direction X, and as shown in FIG. 7, has an opening section 31 that penetrates in the thickness direction X. The opening section 31 is composed of a fore end side opening section 32 formed on a fore end side and having a relatively small up and down width w1 in a height direction Z perpendicular to a longitudinal direction Y and the thickness direction X of the cutter 1, and a rear end side opening section 33 continuously formed on a rear end side of the fore end side opening section 32 and having a larger up and down width w2 than the fore end side opening section 32.

As shown in FIG. 1, the cutter body 2 is formed of a main body block 4 and a slide block 5 retained in the main body block 4 so as to be capable of moving with respect to the main body block 4 in the longitudinal direction Y.

Figure 12:
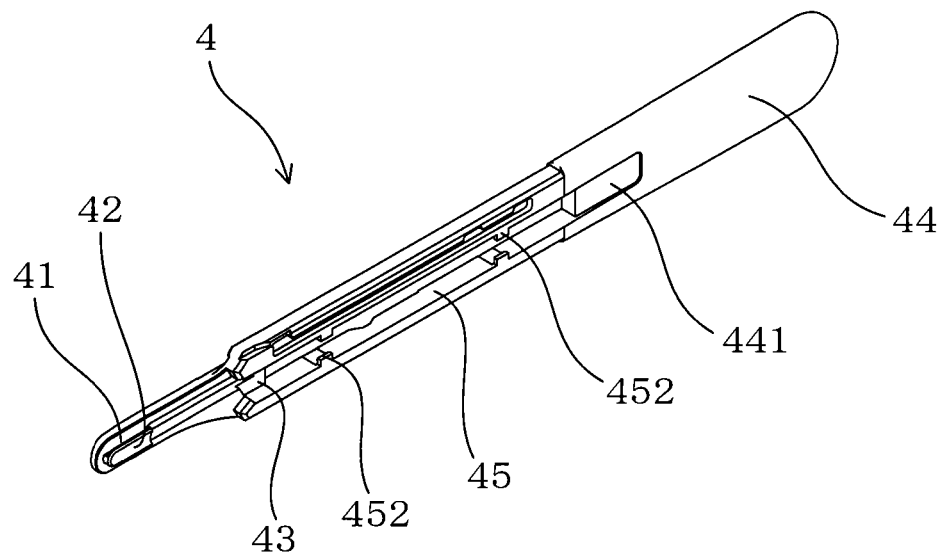
FIG. 12 is a perspective view of a main body block according to the first embodiment.
Figure 13:
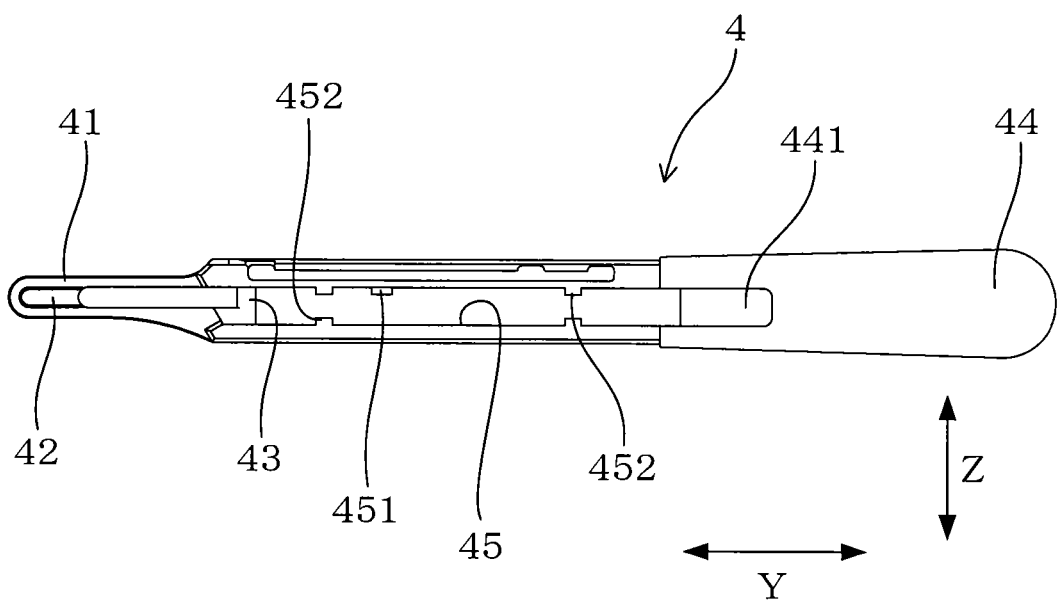
FIG. 13 is a front view of the main body block according to the first embodiment.
Figure 14:
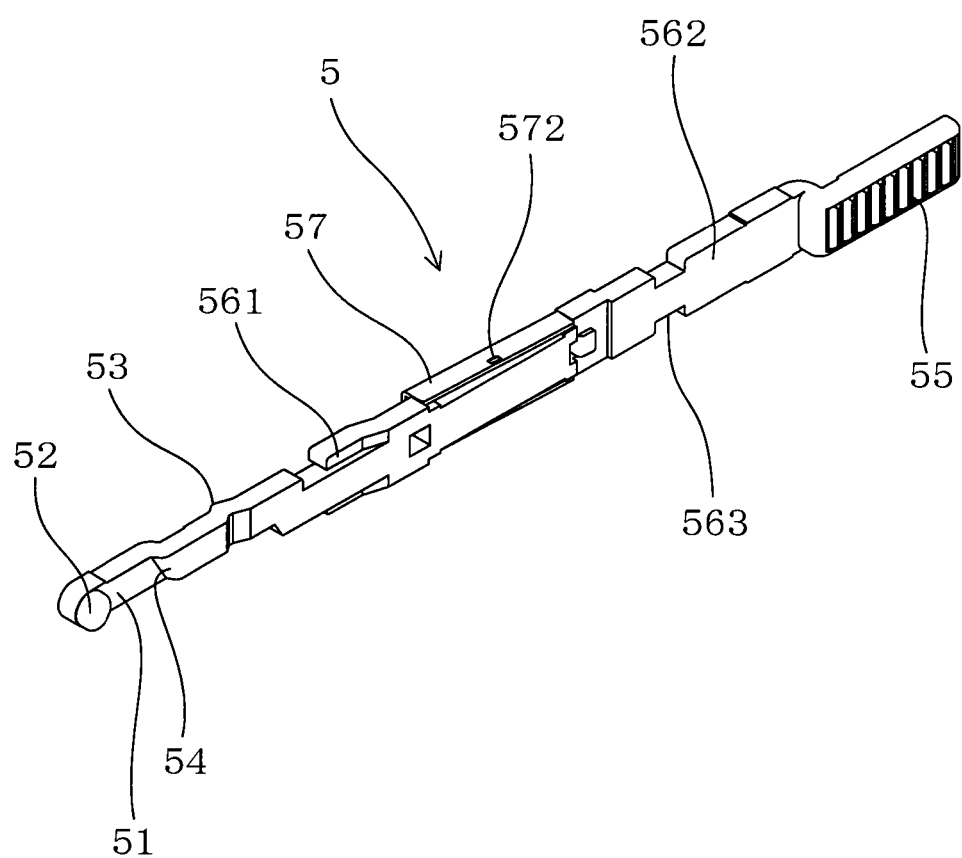
FIG. 14 is a perspective view of a slide block according to the first embodiment.
Figure 15:
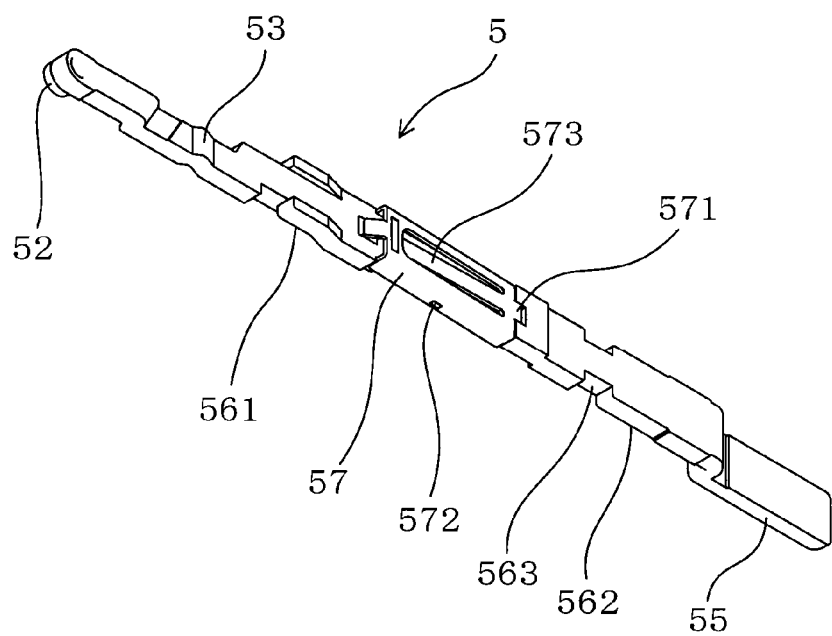
FIG. 15 is another perspective view of the slide block according to the first embodiment.
Figure 16:
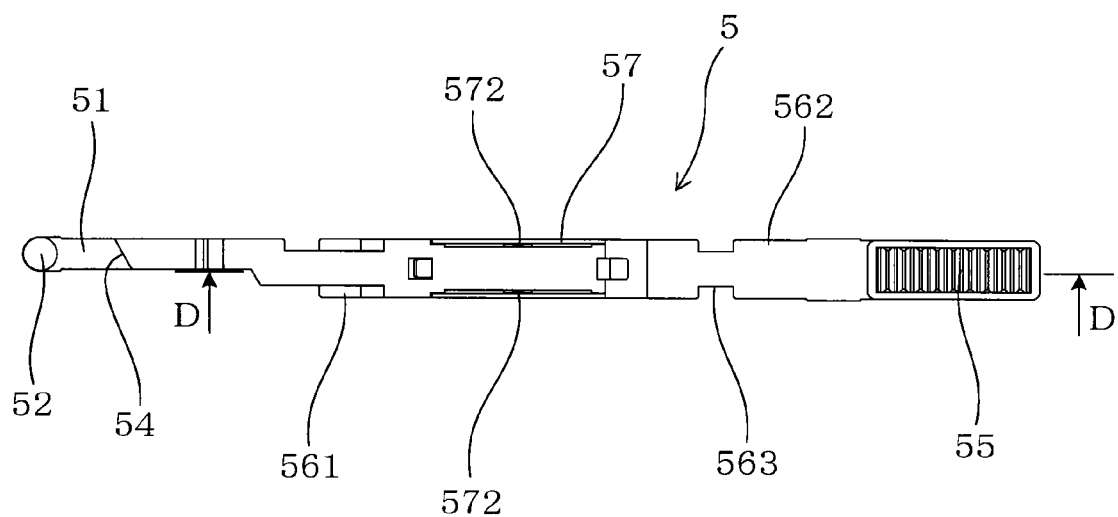
FIG. 16 is a front view of the slide block according to the first embodiment.

As shown in FIG. 12 and FIG. 13, the main body block 4 has a main body supporting section 41 that supports one of primary faces (back face) of the replaceable blade 3, and a main body connecting section 42 that protrudes in the thickness direction X from the main body supporting section 41, is inserted in the fore end side opening section 32 of the replaceable blade 3, and is caused to make contact with a fore end of the opening section 31.

Further, as shown in FIG. 14 to FIG. 18, the slide block 5 has a rear side supporting section 51 that supports the one of primary faces (back face) of the replaceable blade 3, a slide connecting section 52 that protrudes in the thickness direction X from the rear side supporting section 51, is inserted in the rear end side opening section 33, and is caused to make contact with a rear end of the opening section 31, and a back side protruding section 53 that protrudes on an opposite side to the direction in which the slide connecting section 52 protrudes.

Figure 9:
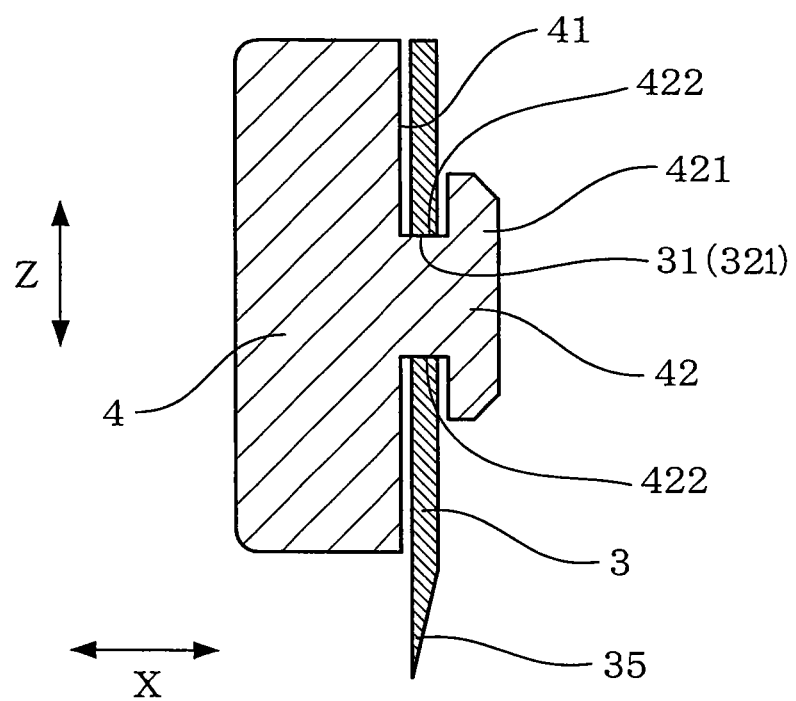
FIG. 9 is a cross sectional view along a line B-B of FIG. 2.

As shown in FIG. 9, the main body connecting section 42 has a head section 421 whose up and down width in the height direction Z is smaller than the rear end side opening section 33 and larger than the fore end side opening section 32, and, slit groove sections 422 that are cut from both sides in the height direction Z are provided between the head section 421 and the main body supporting section 41. The replaceable blade 3 is connected with the slit groove sections 422 at an outer periphery of the fore end side opening section 32.

Figure 11:
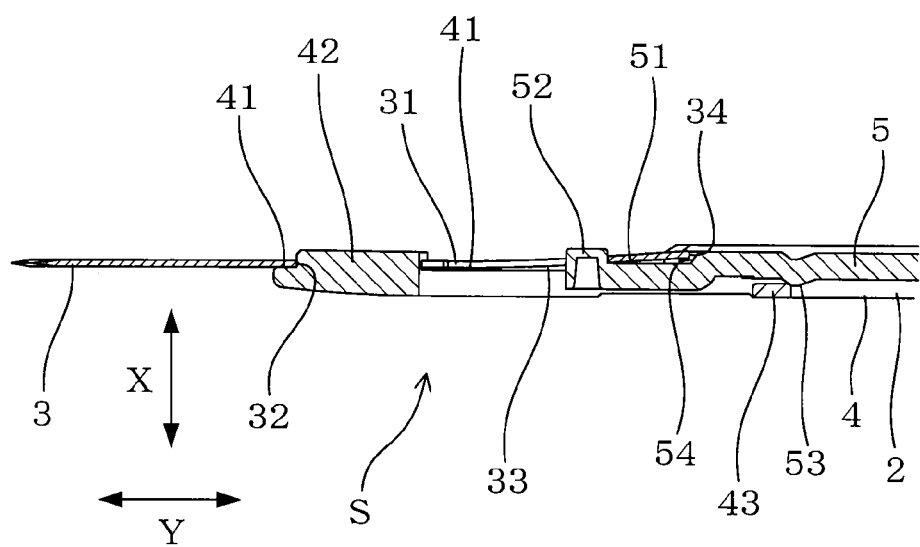
FIG. 11 is a cross sectional view along a line C-C of FIG. 10.

As shown in FIG. 11, in an attached state S in which the replaceable blade 3 is attached to the cutter body 2, the replaceable blade 3 is elastically deformed to curve in the thickness direction X. Due to this, the slide block 5 is pressed toward a main body block 4 side in the thickness direction X by an elastic force of the replaceable blade 3, and the back side protruding section 53 is engaged with an engaged section 43 provided in the main body block 4.

As shown in FIG. 11, in the attached state S, the rear side supporting section 51 protrudes farther than the main body supporting section 41 in the direction in which the rear side connecting section 52 protrudes.

Figure 10:
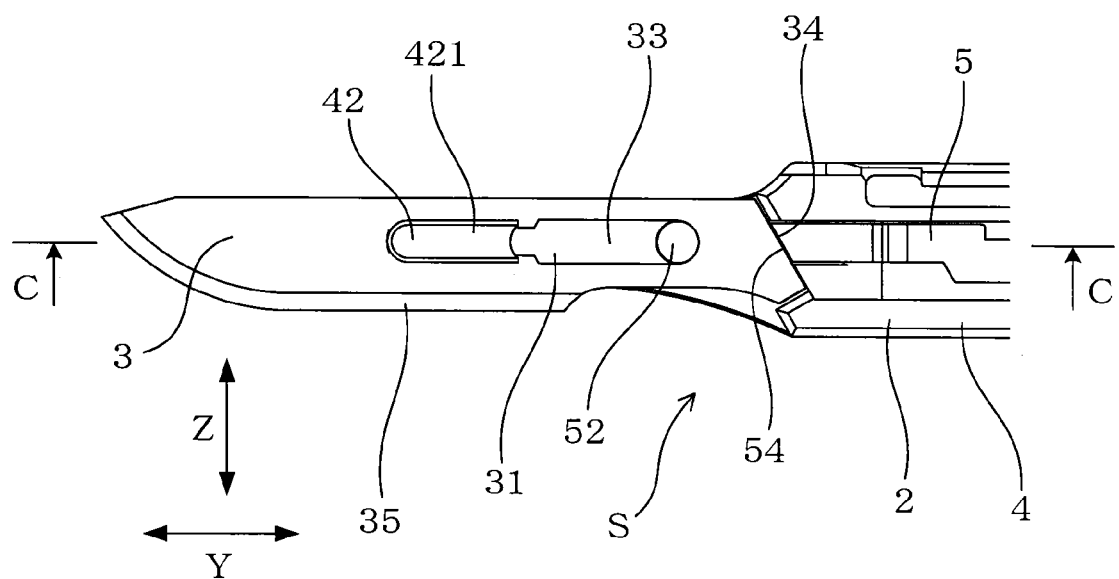
FIG. 10 is a front view of a fore end portion of the cutter according to the first embodiment.
Figure 21:
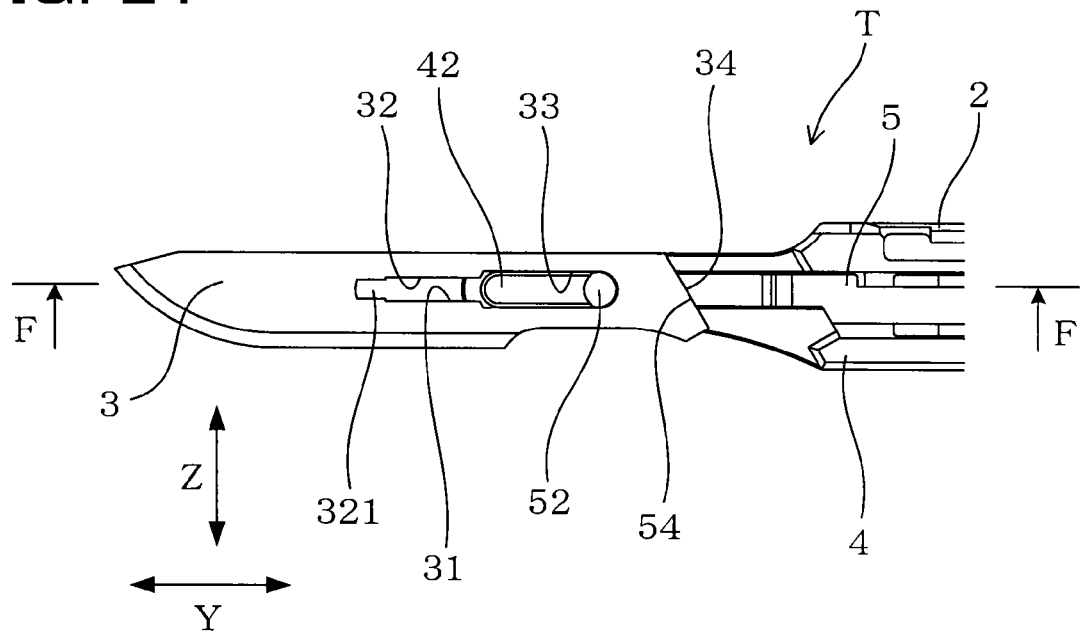
FIG. 21 is a front view of the fore end portion of the cutter in the blade replacing state according to the first embodiment.
Figure 22:
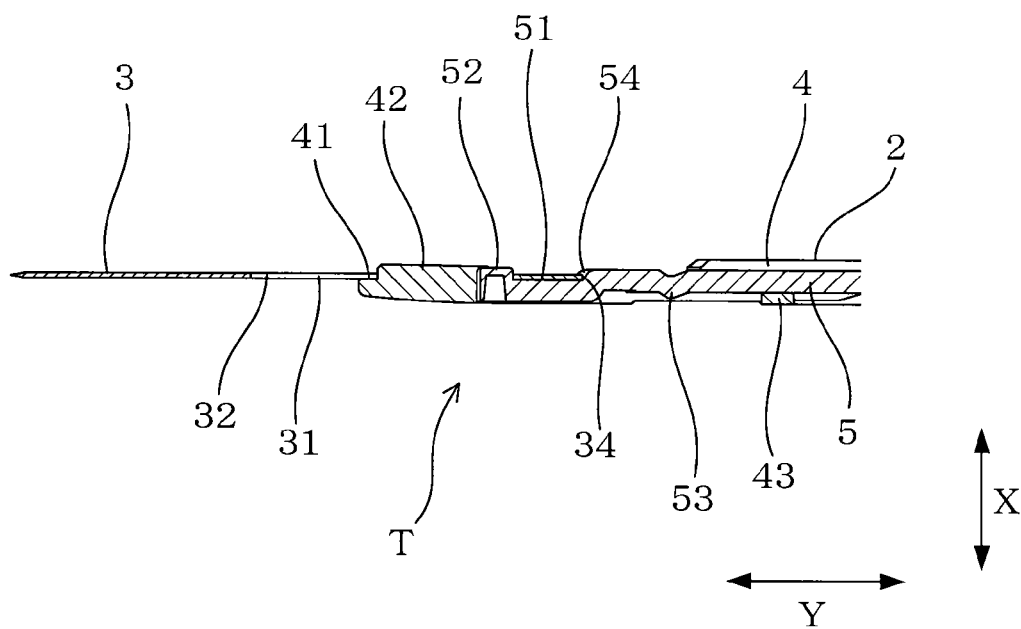
FIG. 22 is a cross sectional view along a line F-F of FIG. 21.

As shown in FIG. 10 and FIG. 11, the slide block 5 includes a rear side opposing face 54 that opposes a rear end 34 of the replaceable blade 3 in the longitudinal direction Y. Further, as shown in FIG. 21 and FIG. 22, when the slide block 5 is moved forward with respect to the main body block 4, the rear side opposing face 54 pushes the replaceable blade 3 out forward by making contact with the rear end 34 of the replaceable blade 3.

The rear end 34 of the replaceable blade 3 and the rear side opposing face 54 are obliquely formed with respect to the longitudinal direction Y when viewed in the thickness direction X.

Further, the main body supporting section 41 has a wider up and down width in the height direction Z than the rear end side opening section 33.

As shown in FIG. 7, the replaceable blade 3 is configured to form a cutting edge 35 on one side in the height direction Z. In the present description, explanation will be given with a direction of the side onto which the blade 35 is formed in the height direction Z being defined as a "lower direction", and an opposite side thereof being defined as an "upper side". Further, in the thickness direction X, the side onto which the replaceable blade 3 is mounted with respect to the cutter body 2 is termed a "front side", and an opposite side thereof is termed a "back side".

The rear end 34 of the replaceable blade 3 is tilted so as to face obliquely upward.

Further, at the fore end side of the fore end side opening section 32, a small width portion 321 having a smaller up and down width in the height direction Z is formed. A stable connecting state can be obtained by fitting a fore end section of the main body connecting section 42 of the main body block 4 into this small width portion 321.

As shown in FIG. 12 and FIG. 13, the main body block 4 of the cutter body 2 has the main body supporting section 41 and the main body connecting section 42 at its fore end portion, and has a grip section 44 at its rear end portion in the longitudinal direction Y. The main body block 4 is configured to provide a container section 45 for slidably containing the slide block 5 at its inside (see FIG. 2 and FIG. 4). The container section 45 almost penetrates in the thickness direction X. Further, on the back side of the container section 45, the engaged section 43 and a back face supporting section 451, which is positioned on the rear side of the engaged section 43 so as to extend from one side in the height direction Z, are formed. Further, on the font side of the container section 45, two pairs of front face supporting sections 452 that are arranged opposing one another are formed.

Figure 8:
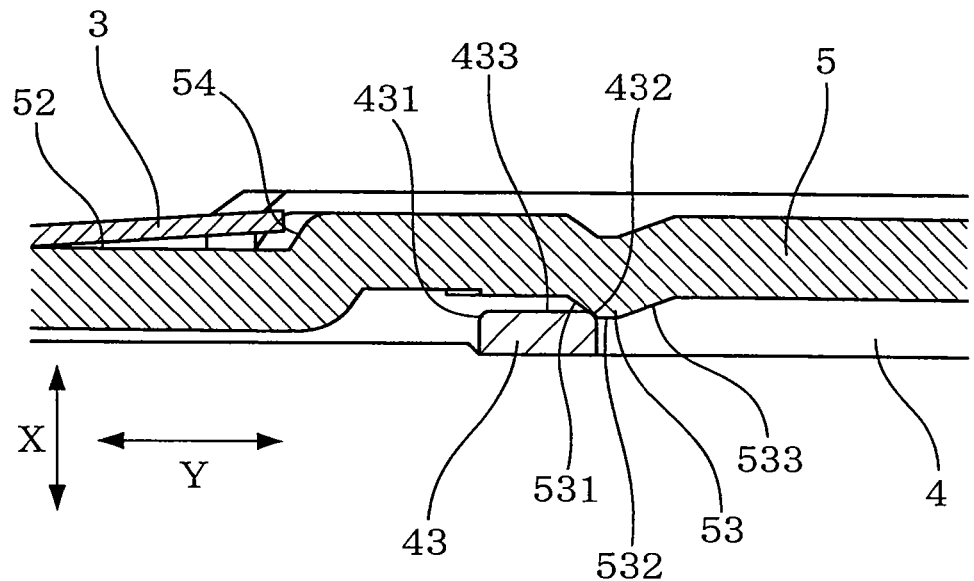
FIG. 8 is an enlarged explanatory cross sectional view of a back side protruding section and a back face engaging section in a connected state of the first embodiment.

As shown in FIG. 8, the engaged section 43 has a substantially rectangular cross section, but chamfered sections having a curved shape are provided at corner sections 431, 432 on the front side.

As shown in FIG. 14 to FIG. 18, the slide block 5 has the rear side supporting section 51 and the slide connecting section 52 at its fore end portion in the longitudinal direction Y, and has an operating section 55 that is raised upwardly on the front side and extends rearward at its rear end portion. A concave-convex section for preventing slippage with a finger of a user (operator) is formed at a front face of the operating section 55. As shown in FIG. 2, FIG. 3, FIG. 19 and FIG. 20, the operating section 55 is slidably mounted on a concaved mounting face 441 provided at the fore end portion of the grip section 44 of the main body block 4.

Further, the slide block 5 is configured to have the rear side opposing face 54 at the rear end of the rear side supporting section 51, and the back side protruding section 53 that protrudes on the back face side on the rear side of the rear side opposing face 54. As shown in FIG. 8, the back side protruding section 53 is formed by two tilted sections 531, 533, and a peak section 532 formed therebetween as an outer shape of a cross section orthogonally intersecting the height direction Z.

Further, the slide block 5 has front face contacting sections 561, 562 respectively at upper and lower positions in the height direction Z on the rear side of the back side protruding section 53 and a foreside of the operating section 55. The front face contacting sections 561, 562 are respectively opposing the front face supporting sections 452 provided in the main body block 4 in a state of not making pressure contact therebetween. Further, at positions respectively adjacent to foresides of the front face contacting sections 561, 562, constricted sections 563 are formed. The slide block 5 can be attached to and detached from the main body block 4 from its front face side under a state in which these constricted sections 563 are aligned at the positions of the front face supporting sections 452.

Figure 3:
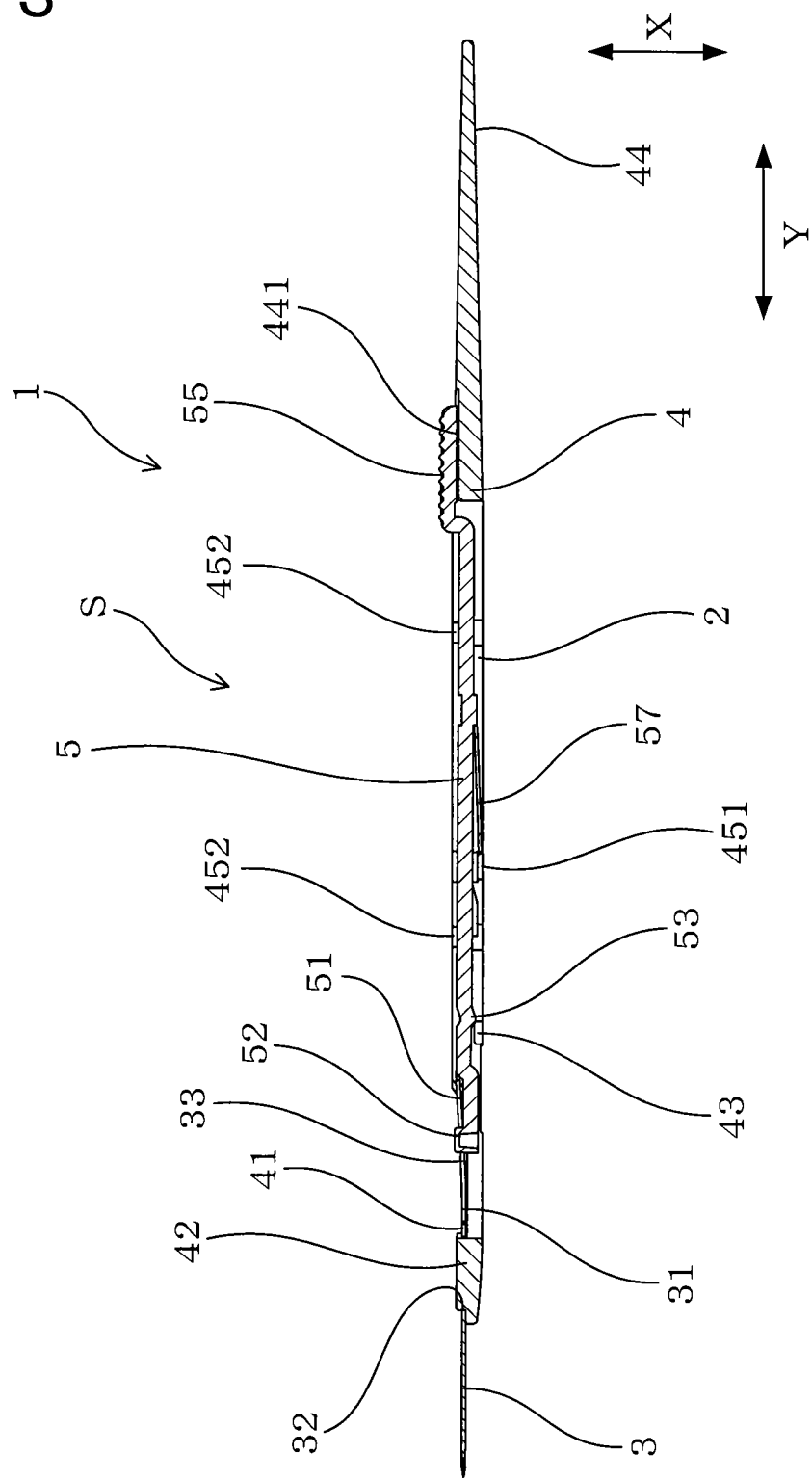
FIG. 3 is a cross sectional view along a line A-A of FIG. 2.
Figure 4:
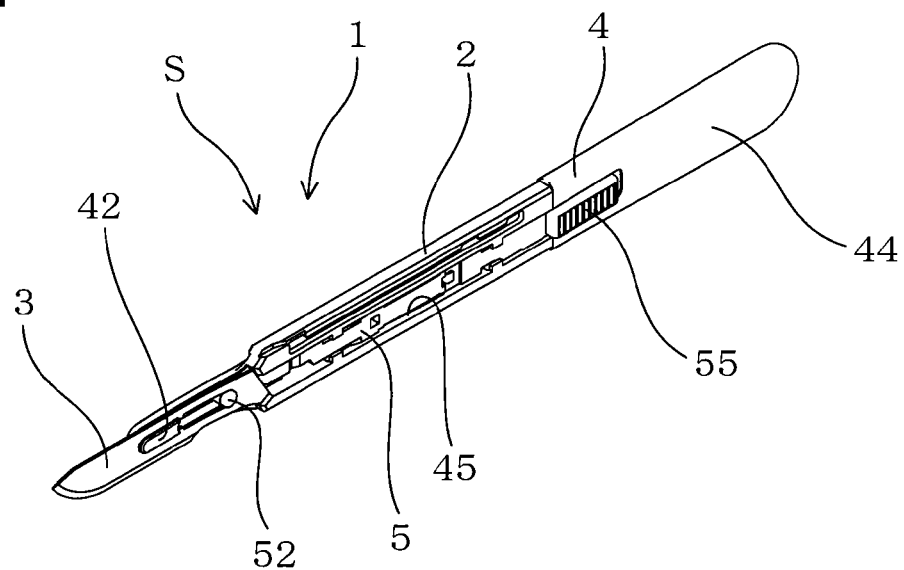
FIG. 4 is a perspective view of the cutter of the first embodiment.
Figure 5:
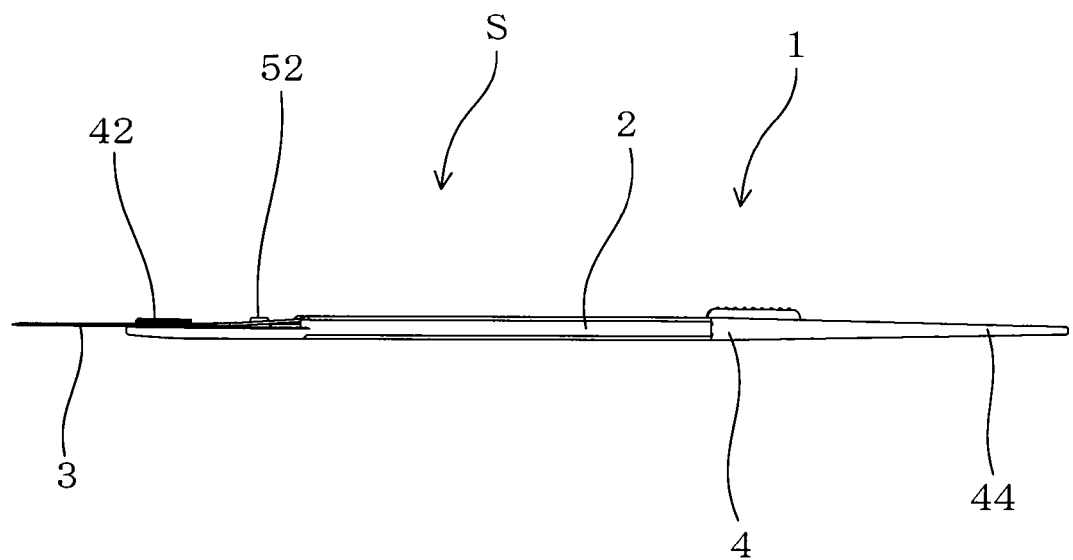
FIG. 5 is a bottom view of the cutter of the first embodiment.
Figure 6:
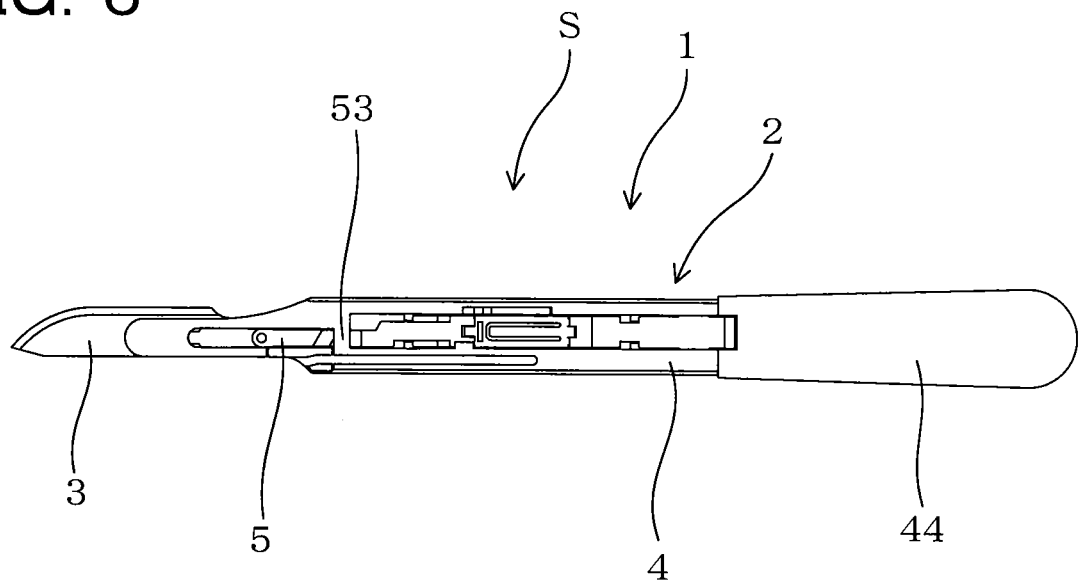
FIG. 6 is a rear face view of the cutter of the first embodiment.

As shown in FIG. 14 to FIG. 18, to the slide block 5 there is fixed a thicknesswise flat spring 57 that extends upwardly on the back side in the thickness direction X and its extension degrees are increased from the rear end side to the fore end side, and that is biased in the thickness direction X. Further, as shown in FIG. 3, in an attached state S, the slide block 5 is prevented from moving forward with respect to the main body block 4 by a fore end section of the thicknesswise flat spring 57 making contact with the contacted section (the back face supporting section 451) provided in the main body block 4.

The thicknesswise flat spring 57 has at its rear end section a fixing section 571 for fixing the thicknesswise flat spring 57 with respect to the slide block 5 so as not to be displaced in the longitudinal direction Y, a pair of engaging claws 572 that engages on the front face side of the slide block 5 at both end sections in the height direction Z, and a center spring section 573 that is bent in the front side compared with its surroundings at a center section in the height direction Z. The center spring section 573 makes contact with the back face of the slide block 5, and the engaging claws 572 are engaged with the front face of the slide block 5, whereby a main body section of the thicknesswise flat spring 57 is put in the state of being biased toward the back face side.

In ending the attached state S, the thicknesswise flat spring 57 is moved along the back face of the slide block 5 against the biasing force of the center spring section 573, whereby the thicknesswise flat spring 57 can end its contacting state with the back face supporting section 451.

Next, an attaching method and a detaching method of the replaceable blade 3 in the cutter 1 of this embodiment will be explained.

Figure 19:
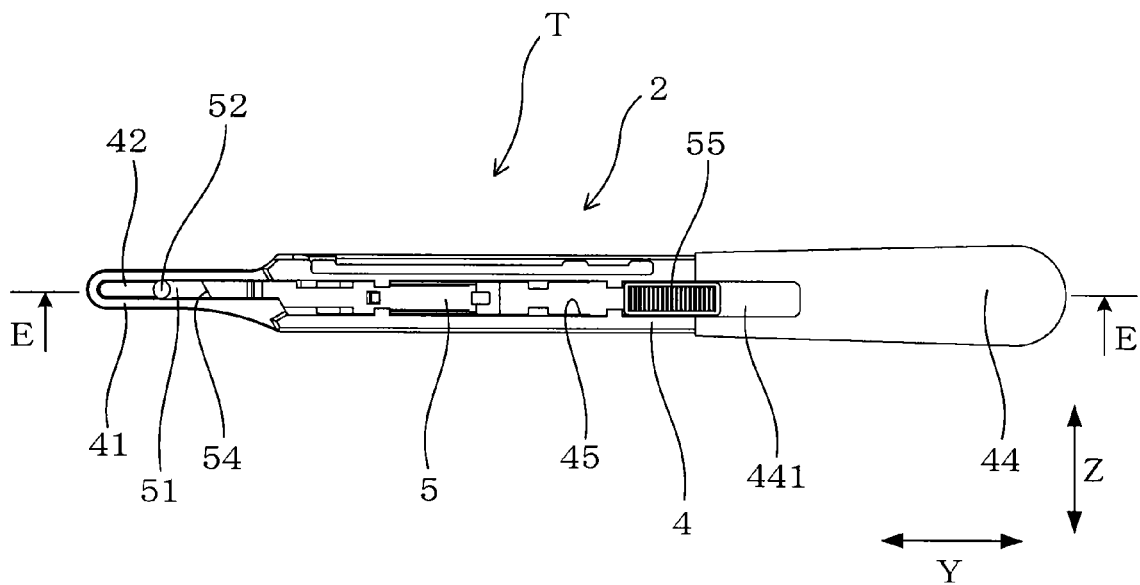
FIG. 19 is a front view of the cutter in a blade replacing state according to the first embodiment.
Figure 20:
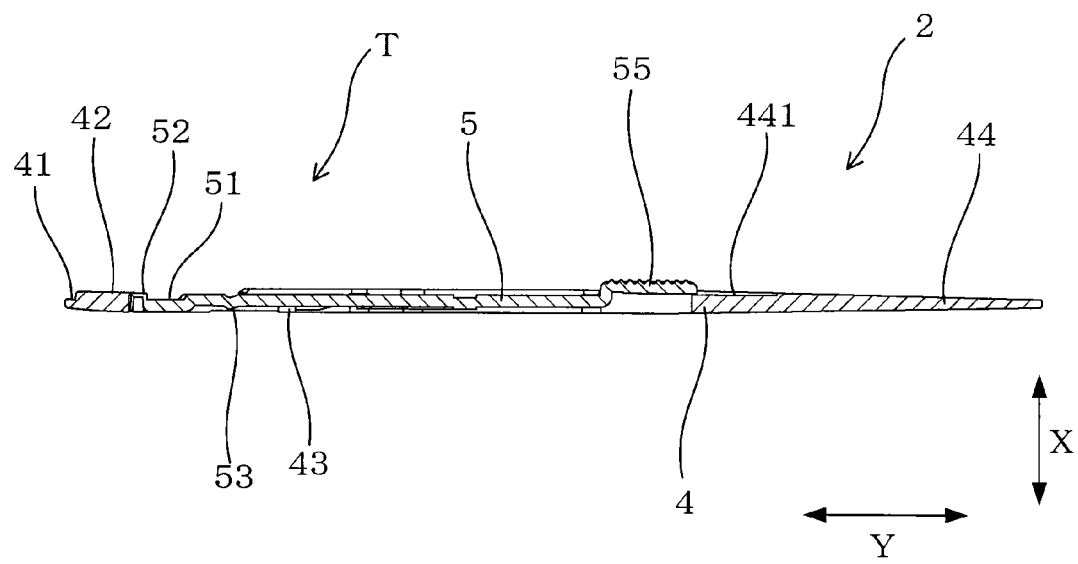
FIG. 20 is a cross sectional view along a line E-E of FIG. 19.

Firstly, as shown in FIG. 19 and FIG. 20, the slide block 5 is moved forward, and the cutter body 2 is put in a blade replacing state T. In this state, the main body connecting section 42 of the main body block 4 and the slide connecting section 52 of the slide block 5 are connected. The replaceable blade 3 is arranged at the fore end section of the cutter body 2 as shown in FIG. 21 and FIG. 22 with the connected main body connecting section 42 and slide connecting section 52 passing through the rear end side opening section 33 of the replaceable blade 3.

At this occasion, one face (back face) of the replaceable blade 3 is caused to make contact with the main body supporting section 41 of the main body block 4 and the rear side supporting section 51 of the slide block 5.

Further, the rear end 34 of the replaceable blade 3 is arranged to oppose the rear side opposing face 54 of the slide block 5, and a small space is formed between them.

Next, the slide block 5 is moved rearward with respect to the main body block 4. Due to this, the slide connecting section 52 pulls the replaceable blade 3 rearward at the rear end of the rear end side opening section 33. Then, as the replaceable blade 3 moves rearward, the main body connecting section 42 moves relatively toward the fore end side opening section 32 of the replaceable blade 3. Due to this, as shown in FIG. 9, the replaceable blade 3 is connected to the slit groove sections 422 provided in the main body connecting section 42 at upper and lower portions of the fore end side opening section 32. Then, by further pulling the slide block 5 farther in the rear side with respect to the main body block 4, as shown in FIG. 10 and FIG. 11, the fore end of the main body connecting section 42 is fitted into the small width portion 321 of the fore end side opening section 32 of the replaceable blade 3, and makes contact with a fore end thereof.

On the other hand, as shown in FIG. 8, upon the slide block 5 being pulled rearward with respect to the main body block 4, the back side protruding section 53 of the slide block 5 is moved on the engaged section 43 from the front side and is engaged with the corner section 432 positioned rear side. That is, in pulling in the slide block 5, the tilted section 533 of the back side protruding section 53 makes contact with the corner section 431 at the foreside of the engaged section 43. Next, the peak section 532 of the back side protruding section 53 is moved on a surface section 433 of the engaged section 43. Next, the tilted section 531 on the foreside of the back side protruding section 53 makes contact with the corner section 432 at the rear side of the engaged section 43. In this state, as shown in FIG. 3 and FIG. 11, the slide block 5 is engaged in the longitudinal direction Y under a state of being pushed out into the front side in the thickness direction X with respect to the main body block 4.

Due to this, the attached state S in which the replaceable blade 3 is attached to the cutter body 2 is realized.

In this attached state S, as shown in FIG. 11, the replaceable blade 3 is elastically deformed in the state of being bend toward the back side in the shape of a convex. That is, as described above, in the attached state S, the slide block 5 is pushed out into the front side with respect to the main body block 4, and the rear side supporting section 51 of the slide block 5 is protruding farther out toward the foreside than the main body supporting section 41 in the main body block 4. Further, a foreside portion of the replaceable blade 3 is connected with the slit groove sections 422 of the main body connecting section 42, and is pressed by the head section 421 from the front side. Due to this, the replaceable blade 3 is attached to the cutter body 2 with elastically deformed into the state in which the rear end 34 is curved toward the front side.

As a result, the slide block 5 is biased toward the back side by the elastic force (restoring force) of the replaceable blade 3, and the back side protruding section 53 is engaged with the engaged section 43. Due to this, the attached state S is locked.

Further, in this state, the thicknesswise flat spring 57 is engaged with the back face supporting section 451, and the lock of the attached state S is made more difficult to be released.

Further, in detaching the replaceable blade 3 from the cutter body 2, the slide block 5 is moved forward with respect to the main body block 4 from the attached state S. On this occasion, by pressing the thicknesswise flat spring 57 in toward the front side along the slide block 5, the connection of the thicknesswise flat spring 57 with the back face supporting section 451 (see FIG. 3) is disconnected.

Then, as the slide block 5 is moved forward, as shown in FIG. 21 and FIG. 22, the replaceable blade 3 is moved forward by the rear side opposing face 54 provided in the slide block 5 pressing the rear end 34 of the replaceable blade 3 forward. Due to this, the main body connecting section 42 of the main body block 4 relatively moves rearward in the opening section 31 of the replaceable blade 3, and shifts from the fore end side opening section 32 to the rear end side opening section 33. Then, when the slide block 5 is moved forward until the slide connecting section 52 makes contact with the main body connecting section 42, both the main body connecting section 42 and the slide connecting section 52 are arranged at the rear end side opening section 33. In this state, the replaceable blade 3 is detached toward the front side.

The replaceable blade 3, the main body block 4 and the slide block 5 are all made of metal such as stainless steel, etc.

Next, an advantageous effect of the present embodiment will be explained.

In the above cutter 1, as described above, easy replacement of only the replaceable blade 3 is to be enabled by moving the slide block 5 forward and backward with respect to the main body block 4 to form the blade replacing state T and the attached state S.

Then, in the attached state S, the replaceable blade 3 is elastically deformed so as to curve in the thickness direction X. Further, the slide block 5 is pressed toward the main body block 4 side (back side) in the thickness direction X by the elastic force of the replaceable blade 3, and the back side protruding section 53 is configured to be engaged with the engaged section 43 provided in the main body block 4. Due to this, the slide block 5 is restricted to move forward, and the attached state S is maintained.

That is, in the cutter 1 of the present embodiment, the slide block 5 can be engaged with the main body block 4 by the elastic force (restoring force) of the replaceable blade 3. Due to this, no new member for restricting the slide block 5 to move forward in the attached state S is required. That is, no member dedicated for restricting the slide block 4 to move forward is required. Thus, the number of components can be decreased, and the configuration thereof can be simplified.

In the present embodiment, although the thicknesswise flat spring 57 is provided as the member for restricting the slide block 5 to move forward, this is merely supplementary providing, and the replaceable blade 3 cannot stably be retained by the cutter body 2 because a play of some degree is formed. That is, a stably fixed state of the replaceable blade 3 can only be realized when a biasing force that pulls the replaceable blade 3 rearward is exerted by the connecting state of the back side protruding section 53 and the engaged section 43 and the elastic force of the replaceable blade 3.

Further, as shown in FIG. 11, when in the attached state S, the rear side supporting section 51 protrudes toward a front side than the main body supporting section 41. Due to this, the replaceable blade 3 connected with the main body connecting section 42 and supported from one of primary faces (back face) by the main body supporting section 41 and the rear side supporting section 51 can easily curve to be in a convex shape toward the main body supporting section 41 and the rear side supporting section 51. Due to this, the slide block 5 is surely biased toward the main body block 4 by the elastic force of the replaceable blade 3, and the back face protruding section 53 can be engaged with the engaged section 43.

Further, the slide block 5 includes the rear side opposing face 54. Due to this, the replaceable blade 3 can be moved forward to easily end the connection with the main body connecting section 42 by moving the slide block 5 forward. Due to this, the replacement of the replaceable blade 3 can more easily be performed.

Further, the rear end 34 of the replaceable blade 3 and the rear side opposing face 54 are obliquely formed with respect to the longitudinal direction Y when viewed from the thickness direction X. Thus, an error in the orientation of the replaceable blade to be attached can be prevented.

Further, the main body supporting section 41 has wider up and down width in the height direction Z than the rear end side opening section 33. Thus, the replaceable blade 3 can easily and stably be attached to the cutter body 2.

As described above, according to the present embodiment, the replacement of only the replaceable blade is enabled while providing the blade with simple configuration with less number of components.

Second Embodiment

As shown in FIG. 23 to FIG. 33, the present embodiment is an example of the cutter 1 having a dual-purposed stopper/cover 6 slidably attached in the longitudinal direction Y with respect to the main body block 4.

Figure 30:
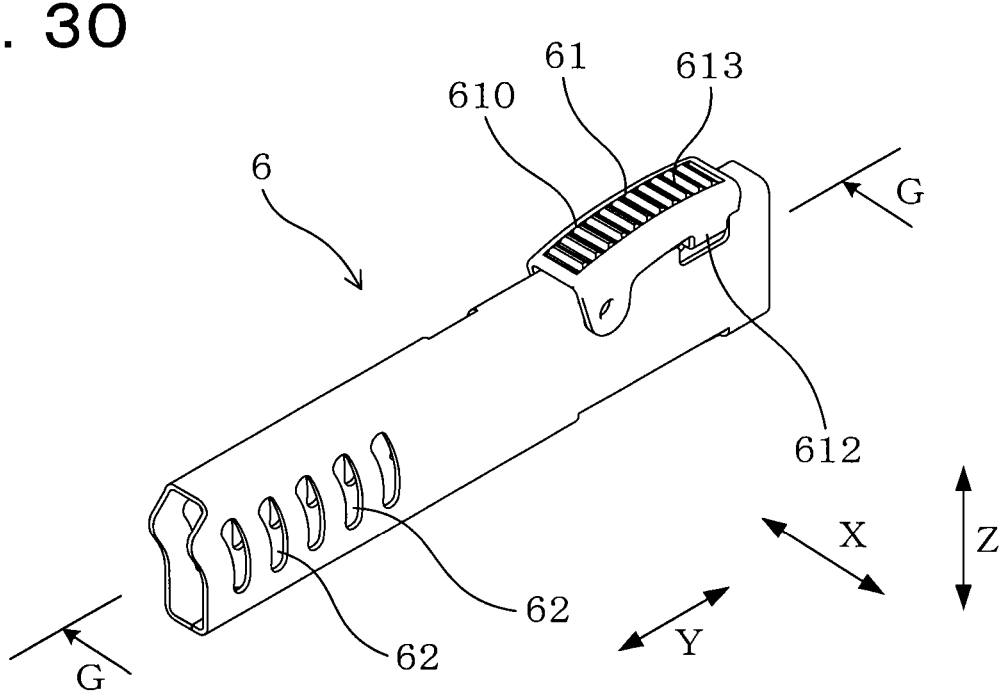
FIG. 30 is a perspective view of the dual-purposed stopper/cover according to the second embodiment.
Figure 31:
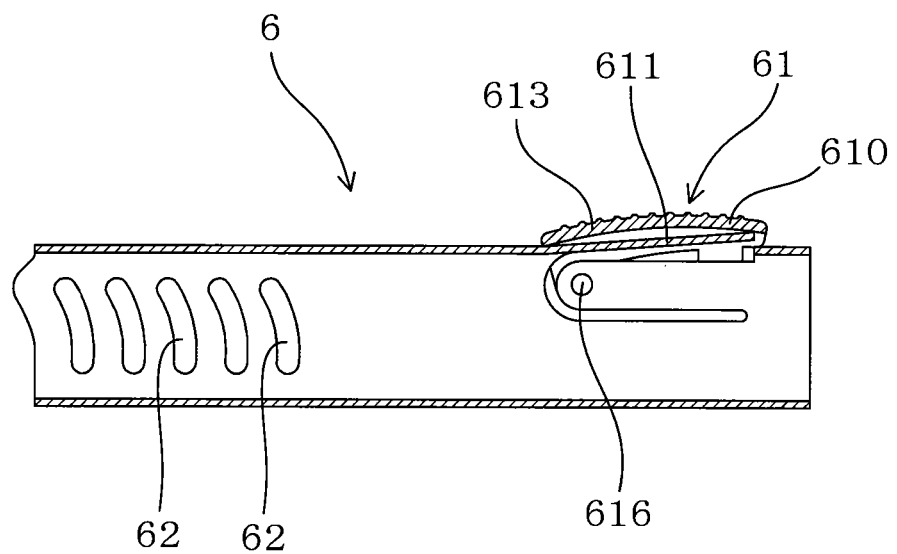
FIG. 31 is a cross sectional view along a line G-G of FIG. 30.

As shown in FIG. 30 and FIG. 31, the dual-purposed stopper/cover 6 has a cylindrical shape that opens in both sides in the longitudinal direction Y. The dual-purposed stopper/cover 6 is made of metal such as stainless steel, etc.

Figure 26:
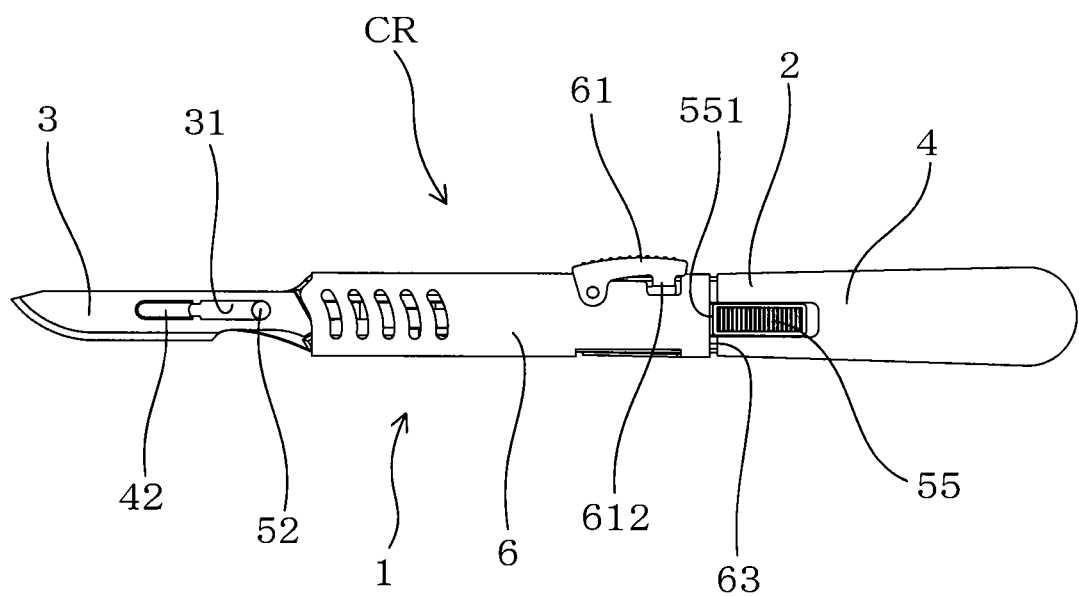
FIG. 26 is a front view of the cutter having the dual-purposed stopper/cover arranged at the rear-side position according to the second embodiment.
Figure 27:
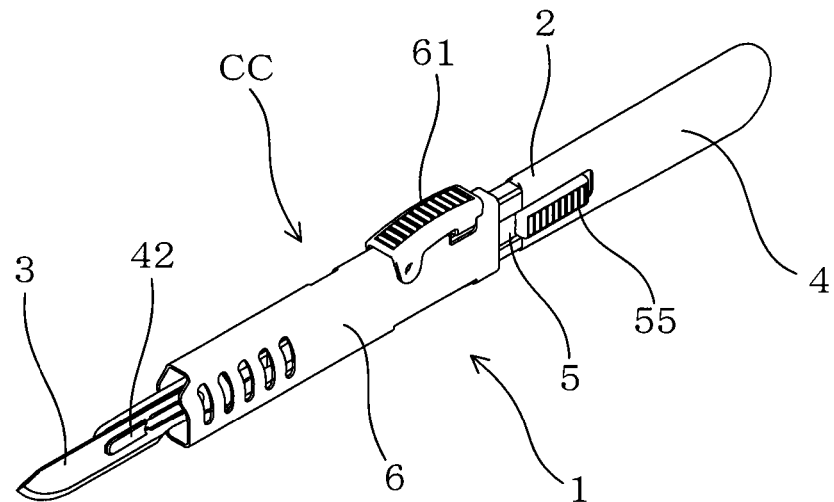
FIG. 27 is a perspective view of the cutter having the dual-purposed stopper/cover arranged at an intermediate position according to the second embodiment.
Figure 28:
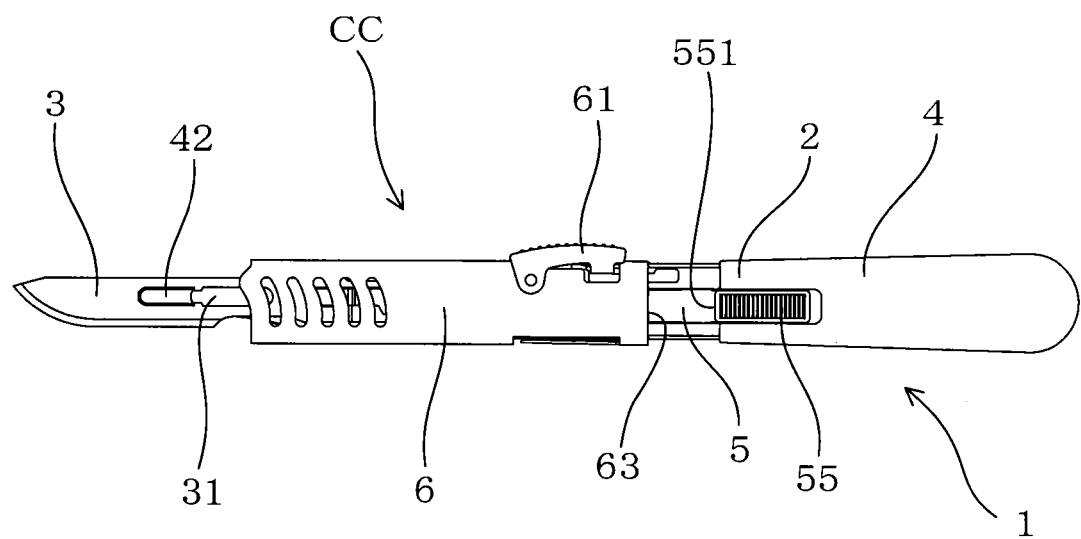
FIG. 28 is a front view of the cutter having the dual-purposed stopper/cover arranged at the intermediate position according to the second embodiment.

Further, the dual-purposed stopper/cover 6 is configured to be capable of being locked at three positions including a foreside position CF in which the replaceable blade 3 is covered (FIG. 23 and FIG. 24), a rear-side position CR in which the replaceable blade 3 is significantly exposed (FIG. 25 and FIG. 26), and an intermediate position CC between the foreside position CF and the rear-side position CR (FIG. 27 and FIG. 28).

The dual-purposed stopper/cover 6 restricts a movement of the slide block 5 with respect to the main body block 4 when it is locked at the rear-side position CR.

Figure 32:
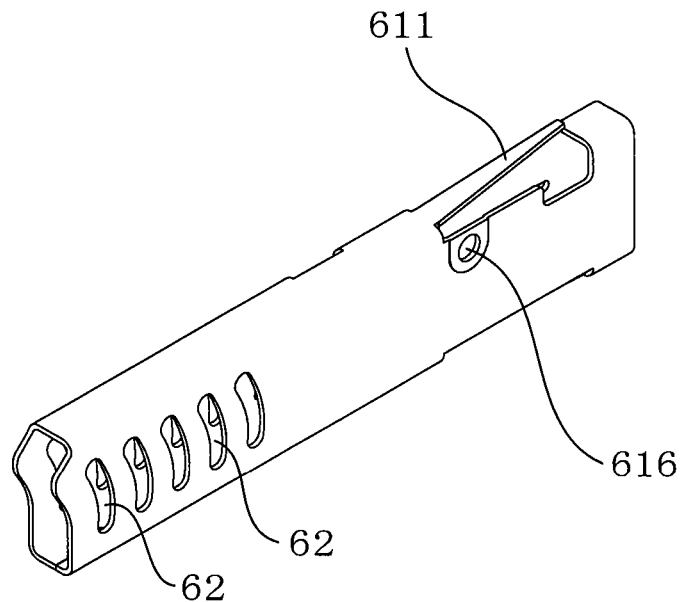
FIG. 32 is a perspective view of the dual-purposed stopper/cover with a lock member detached according to the second embodiment.
Figure 33:
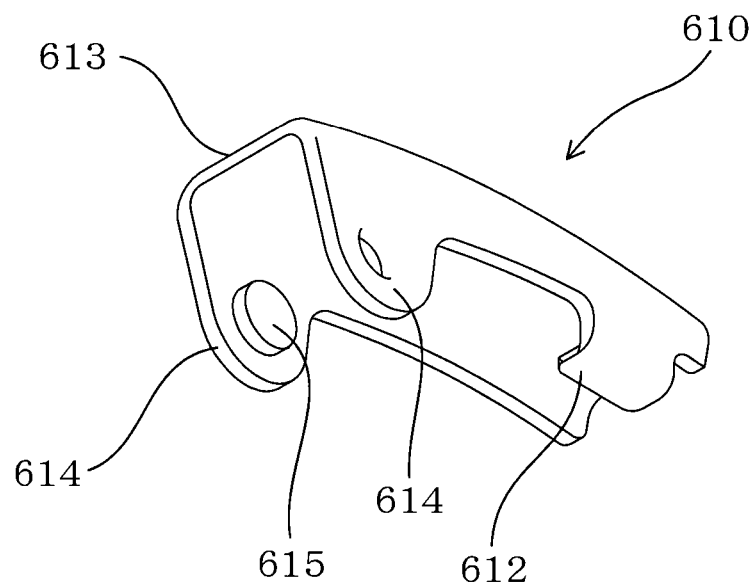
FIG. 33 is a perspective view of the lock member according to the second embodiment.

As shown in FIG. 30 and FIG. 31, the dual-purposed stopper/cover 6 is configured to include a back face lock section 61 at an upper end in the height direction Z. This back face lock section 61 includes a heightwise flat spring 611 biased in an opposite side from the main body block 4, and a claw section 612 formed at a free end of the heightwise flat spring 611 toward an inner side in the thickness direction X. In the present embodiment, as shown in FIG. 32, the heightwise flat spring 611 is formed on an upper face of the dual-purposed stopper/cover 6 so as to elevate from the foreside to the rear side. A lock member 610 shown in FIG. 33 is attached to a main body of the dual-purposed stopper/cover 6 so as to cover the heightwise flat spring 611 from its upper direction and thickness direction X (FIG. 30, FIG. 31). The lock member 610 includes a back face plate 613, a pair of leg sections 614 extending downward from both sides in the thickness direction X at a fore end section of the back face plate 613, and columnar connection protruding sections 615 that protrude inward from the leg sections 614. Further, at a rear portion of the back face plate 613, the claw section 612 is formed so as to extend downward from one end in the thickness direction X and bend inward in the thickness direction X.

Further, as shown in FIG. 31 and FIG. 32, a pair of round holes 616 for connecting the connection protruding sections 615 of the lock member 610 is formed on the main body of the dual-purposed stopper/cover 6. By fitting the connection protruding sections 615 rotatably in the pair of round holes 616, the lock member 610 is connected rotatably with the main body of the dual-purposed stopper/cover 6. As shown in FIG. 30 and FIG. 31, the back face lock section 61 is configured thereby.

Figure 29:
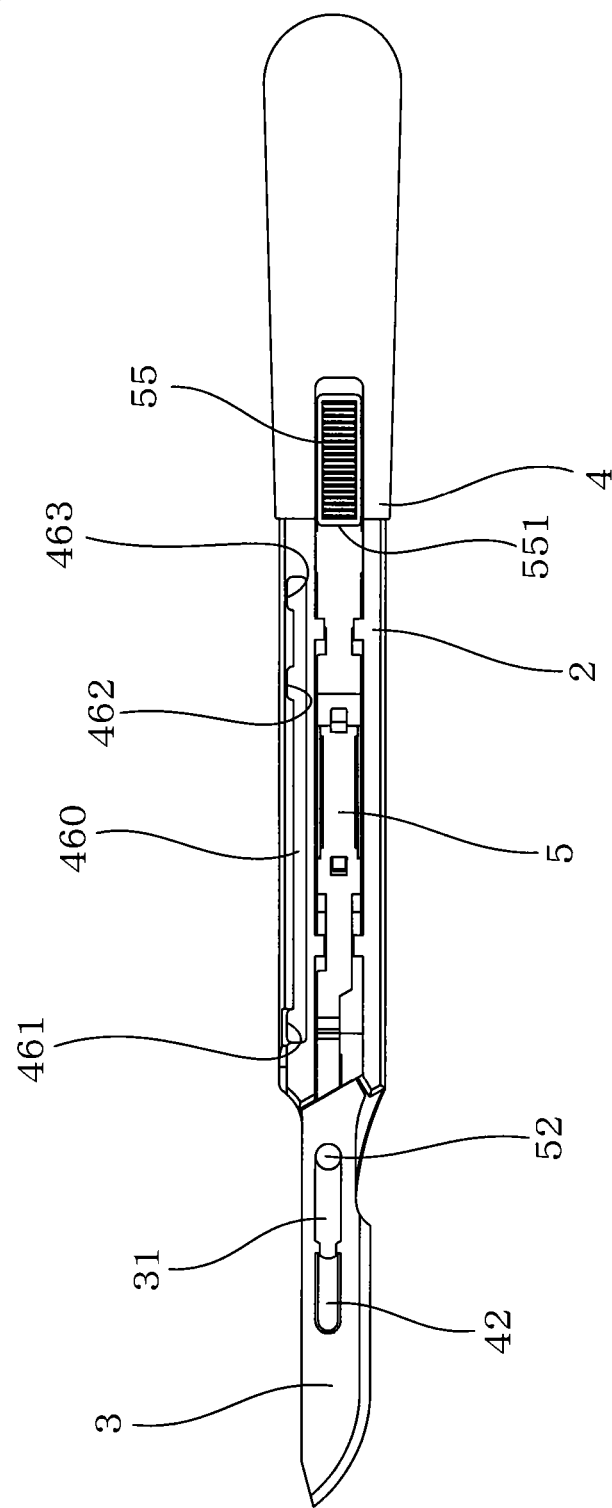
FIG. 29 is a front view of the cutter with the dual-purposed stopper/cover detached according to the second embodiment.

As shown in FIG. 29, the main body block 4 includes the slide groove section 460 formed at a front face thereof in the longitudinal direction Y, a foreside connecting groove 461, an intermediate connecting groove 462, and a rear side connecting groove 463 respectively formed toward an outer side (upper side) in the height direction Z from the slide groove section 460 at three positions in the longitudinal direction Y. The claw section 612 of the dual-purposed stopper/cover 6 is arranged slidably in the slide groove section 460. Further, the dual-purposed stopper/cover 6 is locked at the foreside position CF, the intermediate position CC, or the rear side position CR by connecting the claw section 612 to the foreside connecting groove 461, the intermediate connecting groove 462, or the rear side connecting groove 463, respectively.

Figure 23:
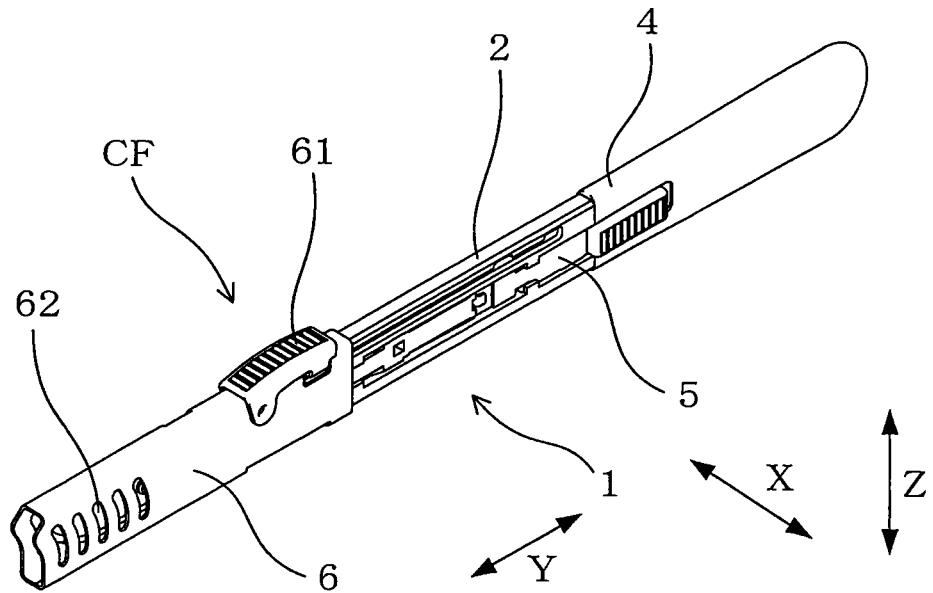
FIG. 23 is a perspective view of a cutter having a dual-purposed stopper/cover arranged at a foreside position according to a second embodiment.
Figure 24:
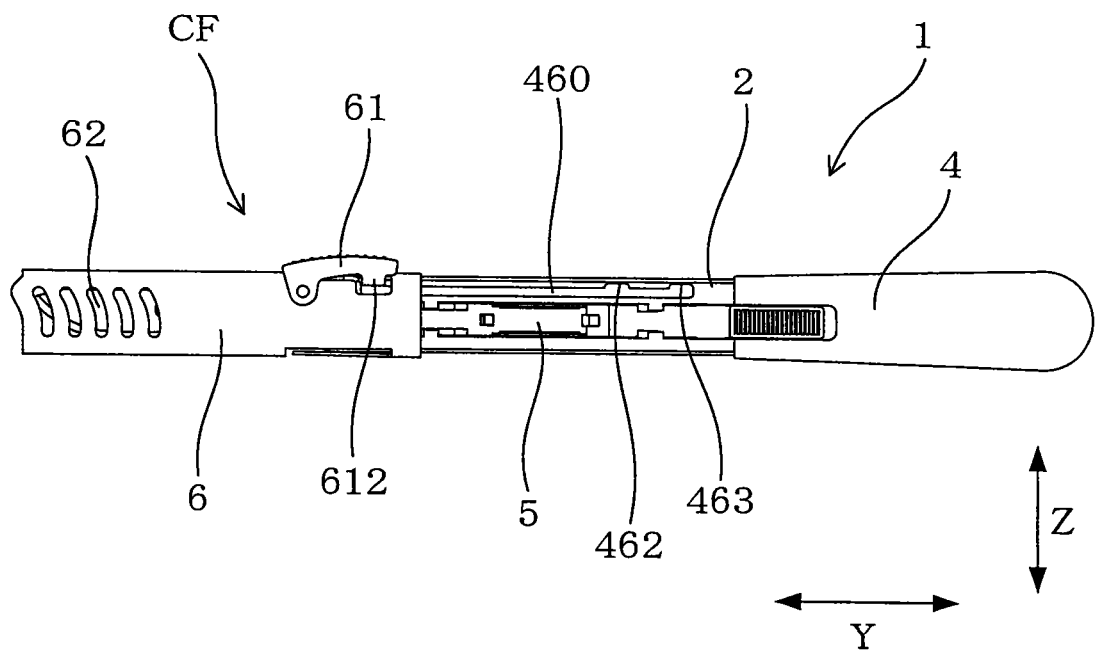
FIG. 24 is a front view of the cutter having the dual-purposed stopper/cover arranged at the foreside position according to the second embodiment.

As shown in FIG. 30, at faces on both sides in the thickness direction X of the dual-purposed stopper/cover 6, a plurality of window sections 62 are formed, each of which penetrates inside the dual-purposed stopper/cover 6. As shown in FIG. 23 and FIG. 24, even when the dual-purposed stopper/cover 6 is arranged at the foreside position CF and realize the state of covering the replaceable blade 3, the replaceable blade 3 can be visually recognized by the presence of the window sections 62. Further, in sterilizing the cutter 1, since the sterilizing solution can pass through the window sections 62, the sterilization of the replaceable blade 3 and the fore end portion of the cutter body 2 can effectively be performed.

Figure 25:
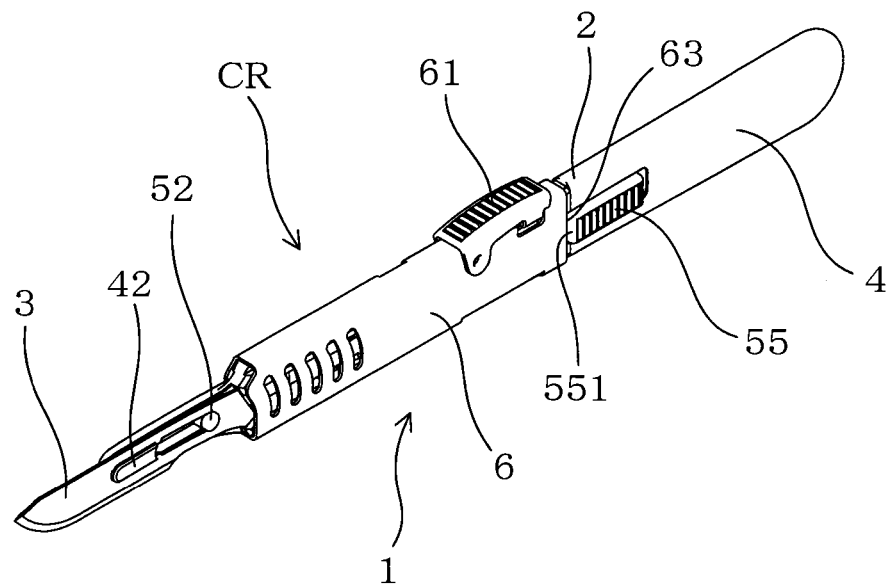
FIG. 25 is a perspective view of the cutter having the dual-purposed stopper/cover arranged at a rear-side position according to the second embodiment.

In the present embodiment, when using the cutter 1, as shown in FIG. 25 and FIG. 26, the dual-purposed stopper/cover 6 is locked at the rear side position CR. In this state, a rear end 63 of the dual-purposed stopper/cover 6 makes contact with a fore end 551 of an operating section 55 of the slide block 5. Accordingly, the forward movement of the slide block 5 can be restricted also by the dual-purposed stopper/cover 6.

Further, when not using the cutter 1, for example, in cases of handing the cutter 1, sterilizing it, or storing it, as shown in FIG. 23 and FIG. 24, the dual-purposed stopper/cover 6 is locked at the foreside position CF. In this state, the dual-purposed stopper/cover 6 is arranged around the replaceable blade 3 attached to the cutter body 2.

Further, when replacing the replaceable blade 3, as shown in FIG. 27 and FIG. 28, the dual-purposed stopper/cover 6 is locked at the intermediate position CC. Due to this, since the operating section 55 is allowed to move forward, the operating section 55 is moved forward, the replaceable blade 3 is detached, and another replaceable blade 3 can be attached.

When the dual-purposed stopper/cover 6 is arranged at the intermediate position CC, the thicknesswise flat spring 57

(see FIG. 3 and FIG. 15) is configured to lay down along the slide block 5 by the dual-purposed stopper/cover 6. Due to this, the thicknesswise flat spring 57 is detached from the back face supporting section 451, and the lock of the attached state S may be unlocked.

Further, to unlock the locked state of the dual-purposed stopper/cover 6 at the foreside position CF, the intermediate position CC or the rear side position CR, the back face lock section 61 is pressed in downward. Due to this, the claw section 612 is detached from the foreside connecting groove 461, the intermediate connecting groove 462, or the rear side connecting groove 463, and arranged in the slide groove section 460. Then, by sliding the dual-purposed stopper/cover 6 in the longitudinal direction Y, the dual-purposed stopper/cover 6 is moved between the foreside position CF, the intermediate position CC, and the rear side position CR.

Other features are identical to those of the first embodiment.

In the present embodiment, since the dual-purposed stopper/cover 6 covers replaceable blade 3 by locking the dual-purposed stopper/cover 6 at the foreside position CF, user's safety can be ensured, and damage to the replaceable blade 3 can be prevented.

Further, in using the cutter 1, the movement of the slide block 5 can be restricted by arranging the dual-purposed stopper/cover 6 at the rear side position CR. Due to this, the use of the cutter 1 can be performed smoothly.

Further, by locking the dual-purposed stopper/cover 6 at the intermediate position CC and moving the slide block 5 forward, the replacement of the replaceable blade 3 can easily be performed.

Further, the dual-purposed stopper/cover 6 includes the heightwise flat spring 611 and the claw section 612, and the main body block 4 includes the slide groove section 460, the foreside connecting groove 641, the intermediate connecting groove 462, and the rear side connecting groove 463. Due to this, the dual-purposed stopper/cover 6 can easily be moved between the foreside position CF, the intermediate position CC, and the rear side position CR and also locked thereat.

Other advantageous effects are identical to those of the first embodiment.

Third Embodiment

Figure 34:
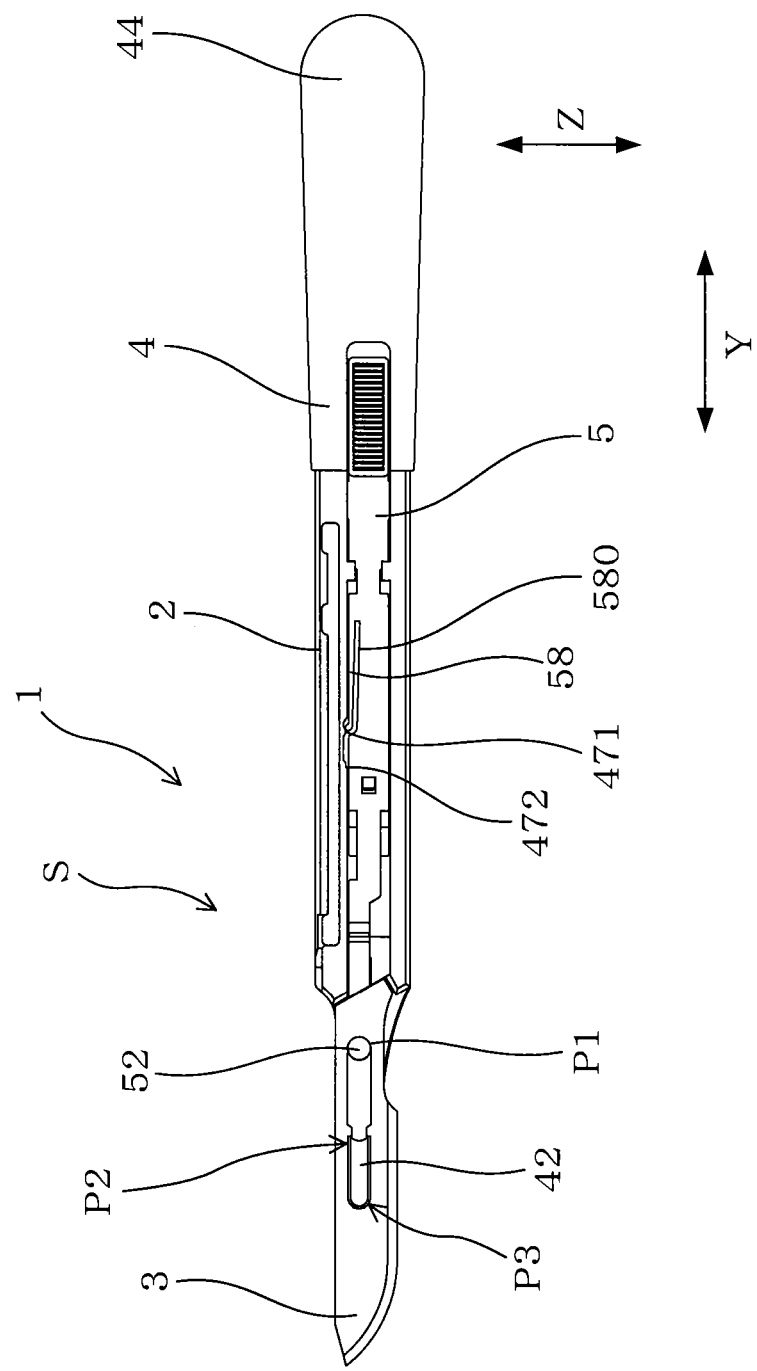
FIG. 34 is a front view of a cutter in the attached state according to a third embodiment.
Figure 35:
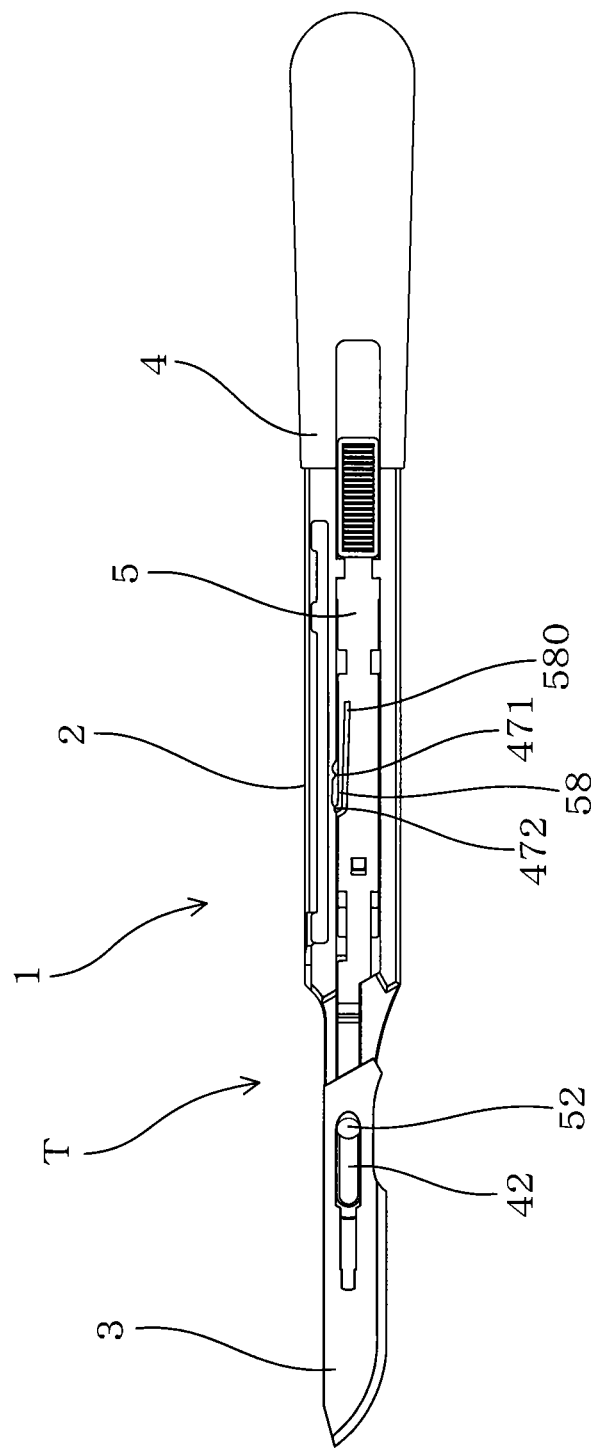
FIG. 35 is a front view of the cutter in the blade replacing state according to the third embodiment.

This embodiment is an example as shown in FIG. 34 and FIG. 35 in which a heightwise elastic member 58 biased toward an upper side in the height direction Z is provided in the slide block 5.

The heightwise elastic member 58 is formed by providing a cut slit section 580 that is cut downwardly from an upper face and extending obliquely to a rear side in the slide block 5. When using a cutter 1, that is, in an attached state S, as shown in FIG. 34, the heightwise elastic member 58 is engaged with a rear side engaging protruding section 471 provided in the main body block 4 in the state of being biased upward.

Further, the slide block 5 is pressed downward with respect to the main body block 4 by a biasing force of the heightwise elastic member 58, and the slide connecting section 52 provided at a fore end portion of the slide block 5 presses a rear end section of a rear end side opening section 33 downward. Due to this, the replaceable blade 3 is supported at the opening section 31 at three points including a lower face (P1) of the slide connecting section 52, an upper face (P2) of the rear end section of the main body connecting section 42, and a lower face (P3) of the fore end section of the main body connecting section 42.

Further, as shown in FIG. 35, the main body block 4 includes a foreside pressure-contact section 472 that is capable of making a pressurized contact with the heightwise elastic member 58 in the height direction Z in the blade replacing state T in which the slide block 5 is moved forward with respect to the main body block 4. The foreside pressure-contact section 472 is configured to restrict a movement of the slide block 5 with respect to the main body block 4 by the heightwise elastic member 58 making the pressurized contact with the foreside pressure-contact section 472. That is, in the blade replacing state T, the slide block 5 can maintain immovable state with respect to the main body block 4 by a friction force between the heightwise elastic member 58 and the foreside pressure-contact section 472.

In the present embodiment, the thicknesswise flat spring 57 shown in the first embodiment is not provided.

The others are identical to those of the first embodiment.

In the case of the present embodiment, as shown in FIG. 34, in the attached state S, looseness in the height direction Z between the replaceable blade 3 and the cutter body 2 can effectively be prevented. Especially, by supporting the replaceable blade 3 at the three positions at the opening section 31, namely, the lower face (P1) of the slide connecting section 52, the upper face (P2) of the rear end section of the main body connecting section 42, and the lower face (P3) of the fore end section of the main body connecting section 42, the replaceable blade 3 is retained in an attitude with which a fore end of the replaceable blade 3 does not point further upward. An upward counterforce that is exerted on the cutting edge upon using the blade 3 can be resisted in this state, and a displacement of the replaceable blade 3 can more effectively be prevented.

Further, the main body block 4 includes the foreside pressure-contact section 472, and is configured to restrict the movement of the slide block 5 with respect to the main body block 4 by the heightwise elastic member 58 making the pressurized contact with the foreside pressure-contact section 472. Due to this, since the blade replacing state T can easily be retained, the replacement of the replaceable blade 3 can easily be performed.

Other advantageous effects are identical as those of the first embodiment.

Figure 36:
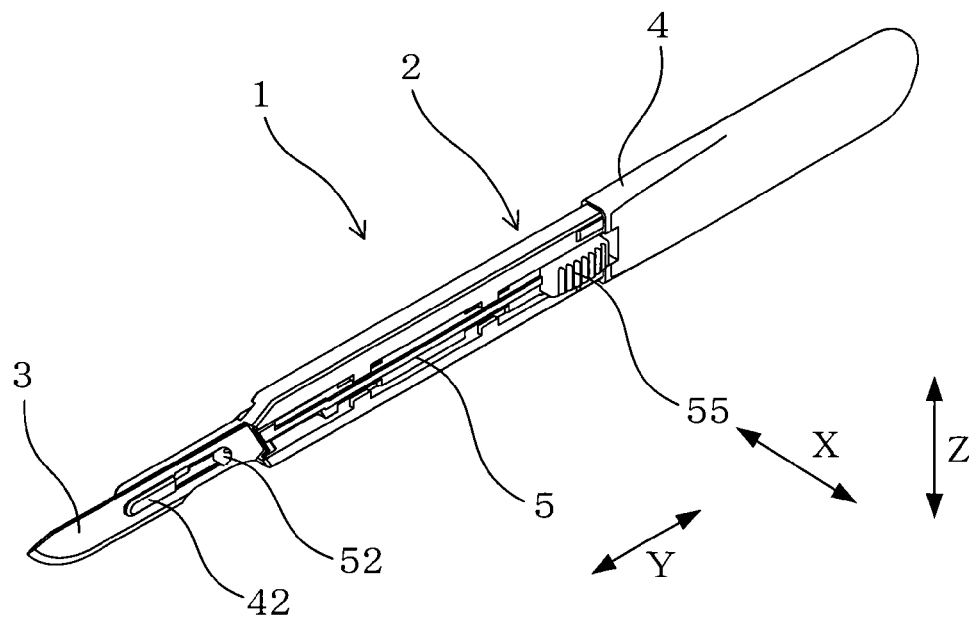
FIG. 36 is a perspective view of a cutter according to a fourth embodiment.
Figure 37:
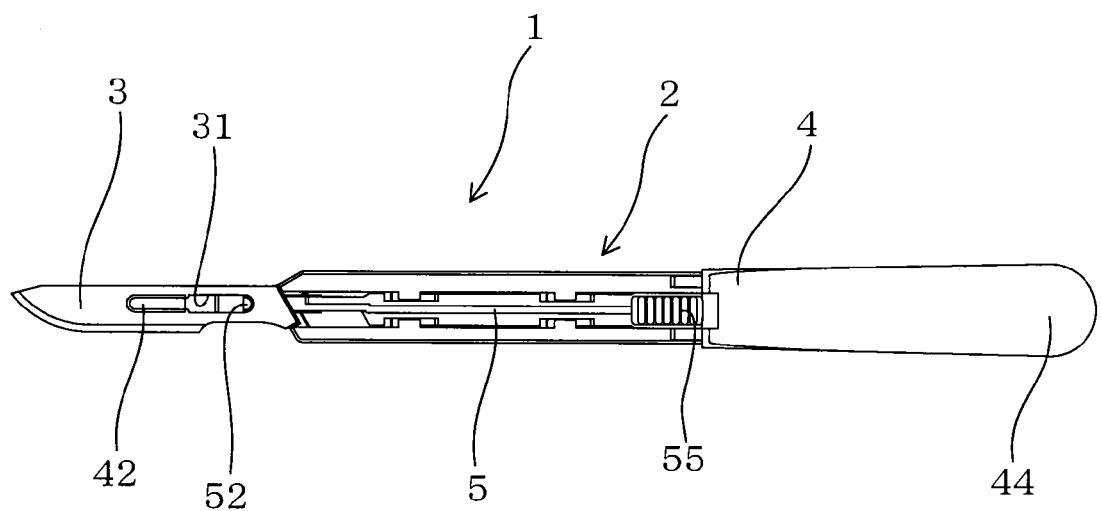
FIG. 37 is a front view of the cutter according to the fourth embodiment.

The reference numerals given in FIG. 34 and FIG. 35 correspond to those shown in the first embodiment, unless mentioned otherwise. The same applies to FIG. 36 and the following figures to be described later.

Fourth Embodiment

This embodiment is an example as shown in FIG. 36 to FIG. 39 of a cutter 1 in which the shape of the cutter body 2 is different from that of the first embodiment.

Figure 38:
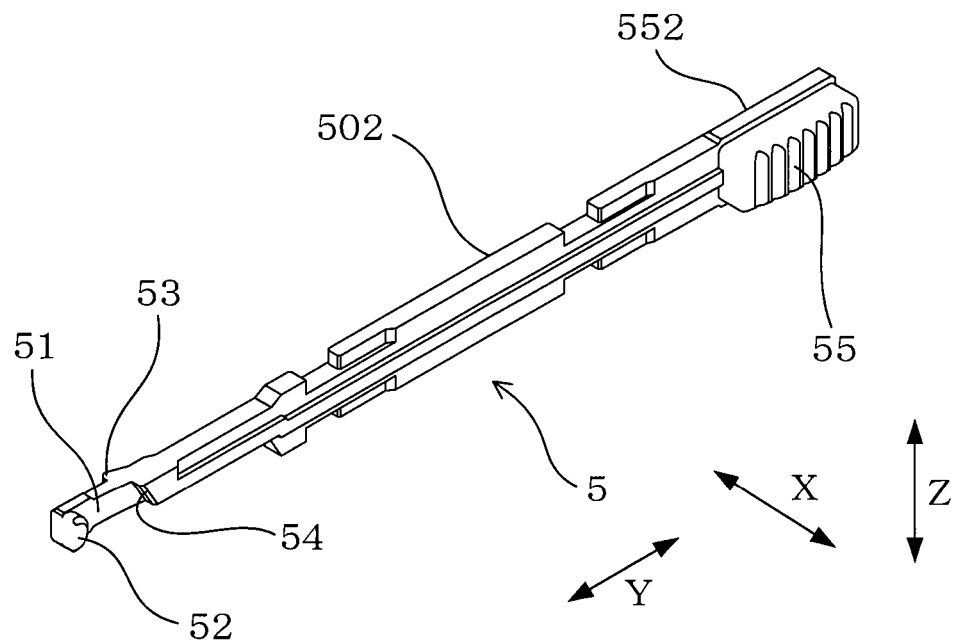
FIG. 38 is a perspective view of a slide block according to the fourth embodiment.
Figure 39:
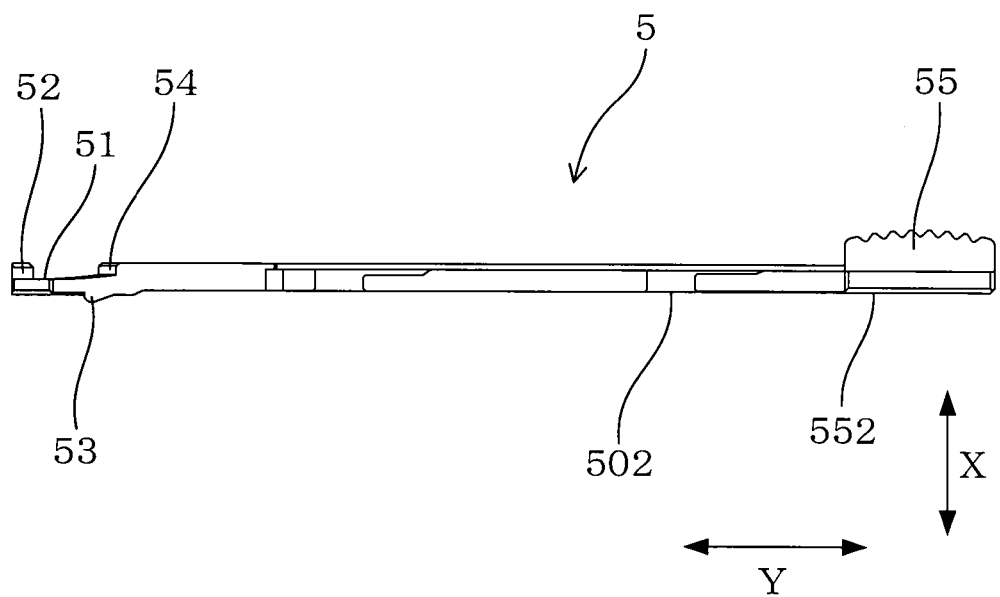
FIG. 39 is a bottom view of the slide block according to the fourth embodiment.
Figure 40:
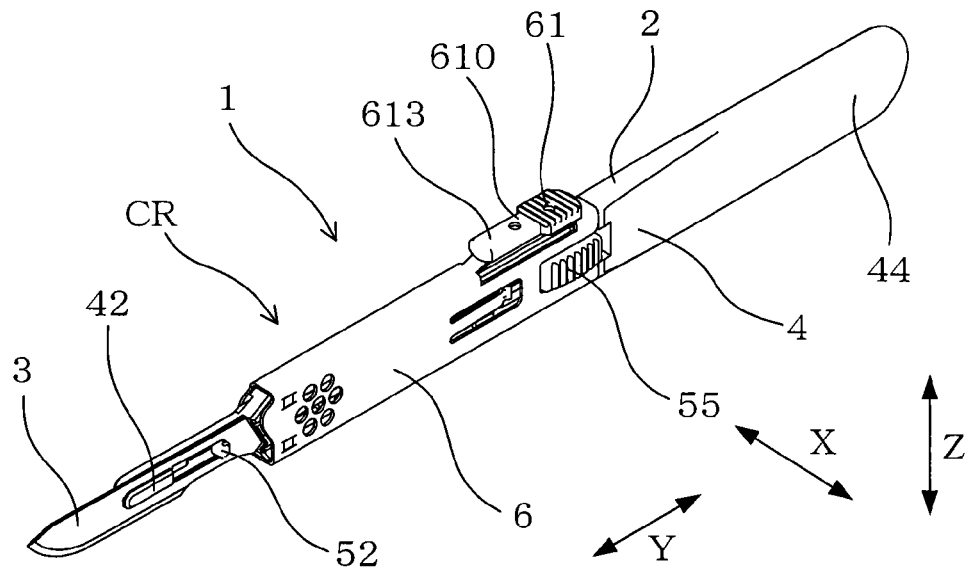
FIG. 40 is a perspective view of a cutter having a dual-purposed stopper/cover arranged at the rear-side position according to a fifth embodiment.
Figure 41:
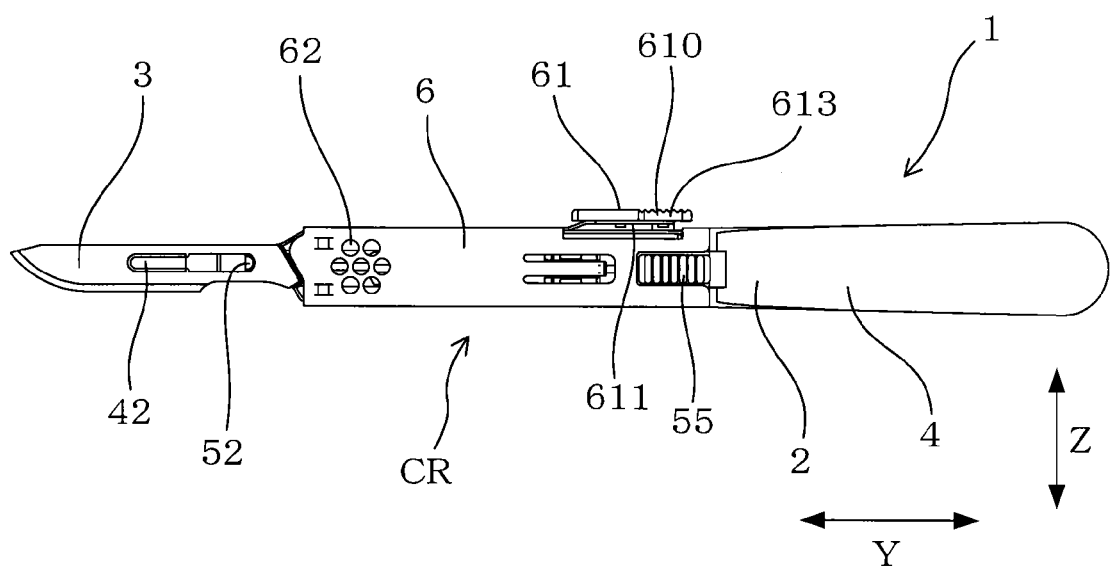
FIG. 41 is a front view of the cutter having the dual-purposed stopper/cover arranged at the rear-side position according to the fifth embodiment.

In the cutter 1 of the present embodiment, as shown in FIG. 38 and FIG. 39, the slide block 5 has a shape in which a back face 552 of the operating section 55 provided at a rear end portion is arranged on the same plane as a back face 502 of a foreside portion of the operating section 55.

Figure 17:
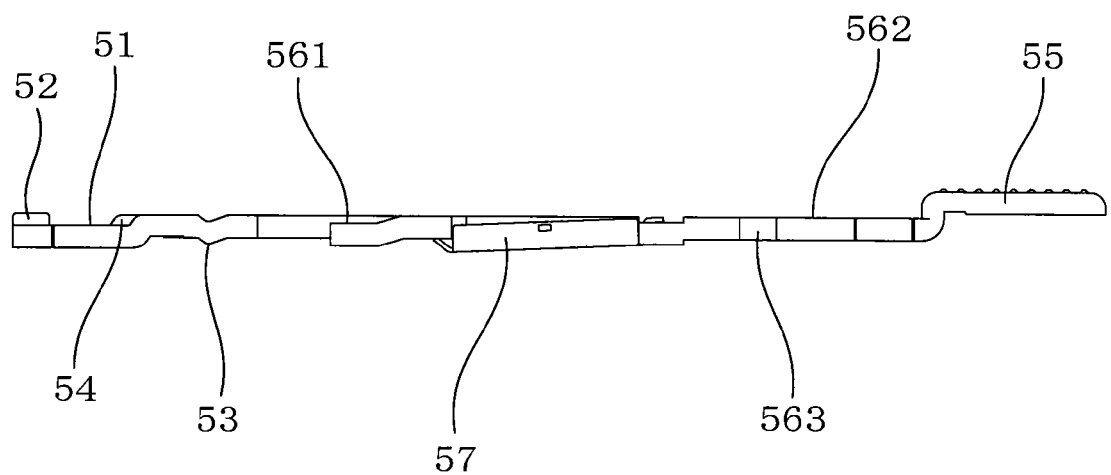
FIG. 17 is a bottom view of the slide block according to the first embodiment.
Figure 18:
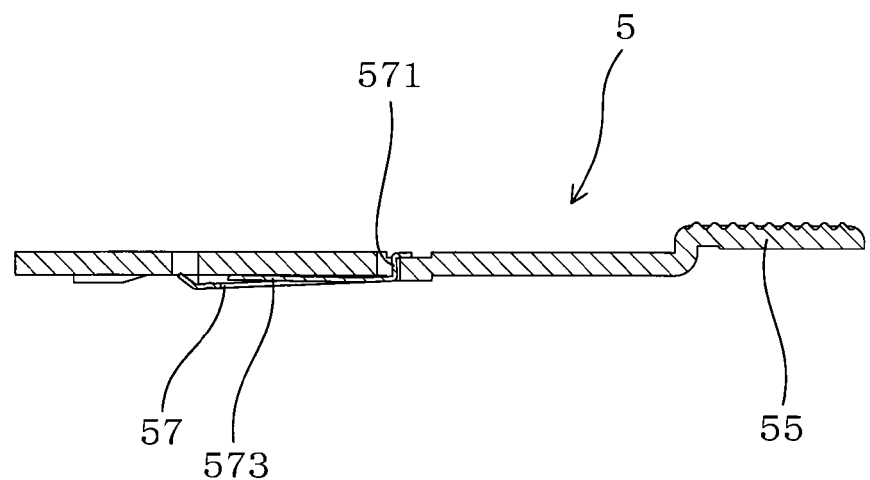
FIG. 18 is a cross sectional view along a line D-D of FIG. 16

That is, as shown in FIG. 17, the operating section 55 of the cutter 1 of the first embodiment has a shape that is raised upwardly on the front side and extends rearward, and the back face of the operating section 55 is located farther frontward than the back face of the foreside portion of the operating section 55. Whereas, the back face 552 of the operating section 55 in the cutter 1 of the present embodiment is not displaced frontward, and forms the same plane that is continuing from the back face 502 of the foreside portion.

Due to this arrangement, the main body block 4 does not need the concaved mounting face 441 (FIG. 12 and FIG. 13) as in the first embodiment, and the back face 552 of the operating section 55 is slidably placed on the surface that forms continuous plane with the surface on which the back face 502 of the other parts are slidably placed (not shown).

Other features are identical to those of the first embodiment.

In the present embodiment also, the identical advantageous effects as those of the first embodiment are obtained.

Fifth Embodiment

This embodiment is an example as shown in FIG. 40 to FIG. 47 in which a dual-purpose stopper/cover 6 is slidably attached in the longitudinal direction Y to the main body block 4 of the cutter 1 (FIG. 36 and FIG. 37) according to the fourth embodiment.

Functions and configuration of the dual-purposed stopper/cover 6 are substantially identical to those of the dual-purposed stopper/cover 6 in the cutter 1 (FIG. 23 to FIG. 28) of the second embodiment.

Figure 42:
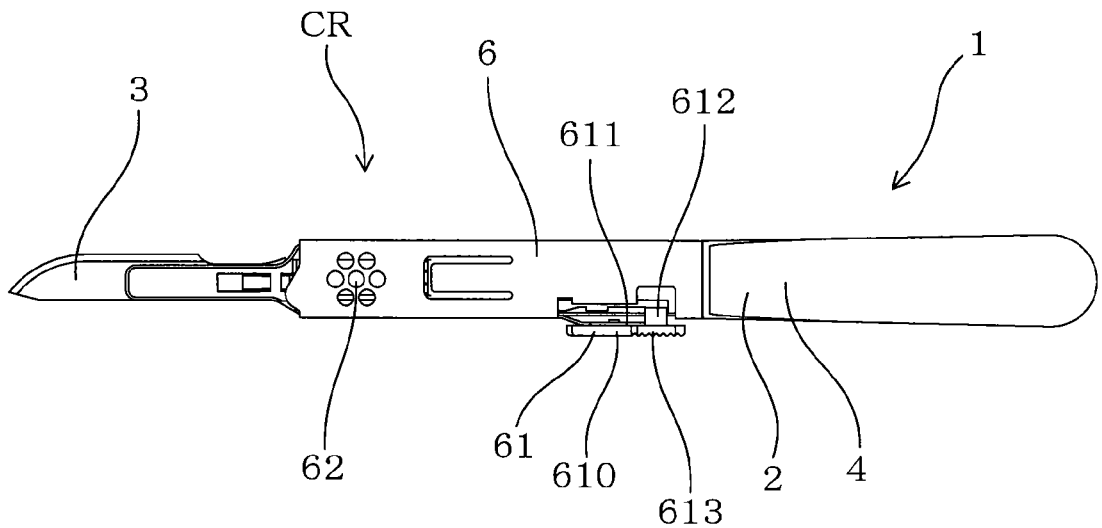
FIG. 42 is a rear face view of the cutter having the dual-purposed stopper/cover arranged at the rear-side position according to the fifth embodiment.
Figure 43:
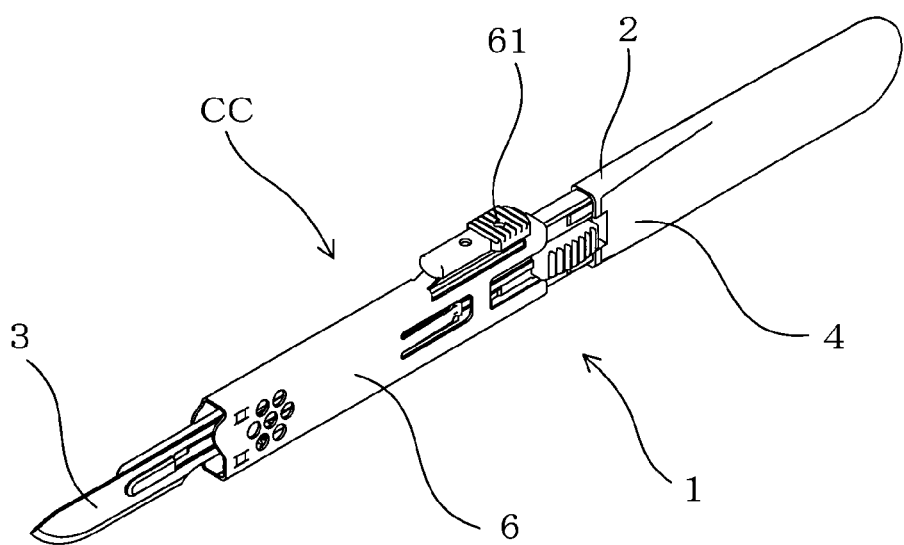
FIG. 43 is a perspective view of the cutter having the dual-purposed stopper/cover arranged at the intermediate position according to the fifth embodiment.
Figure 44:
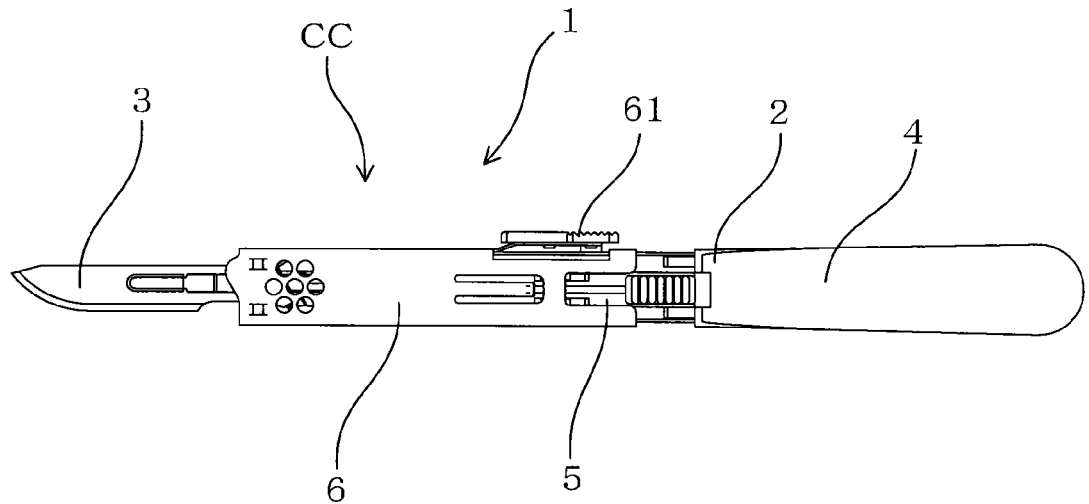
FIG. 44 is a front view of the cutter having the dual-purposed stopper/cover arranged at the intermediate position according to the fifth embodiment.
Figure 45:
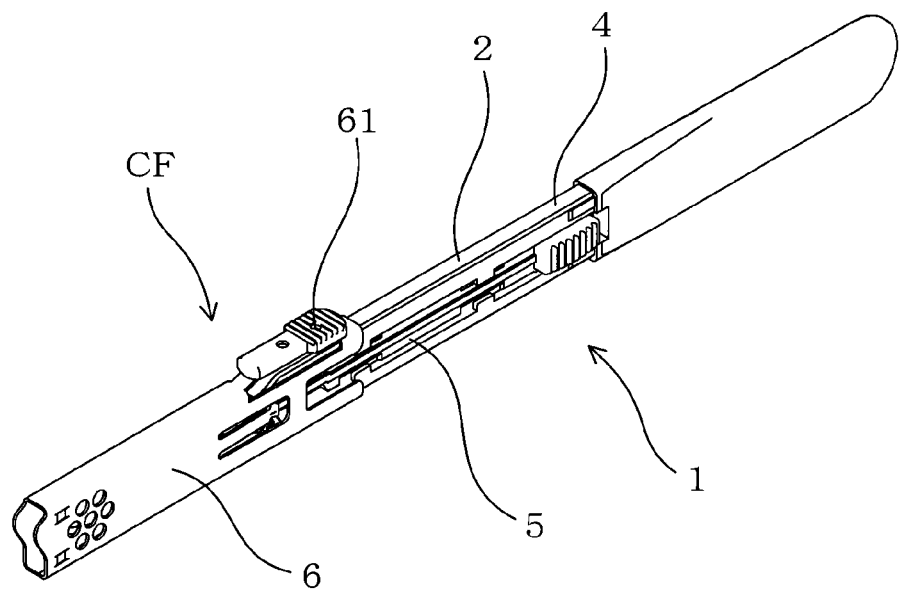
FIG. 45 is a perspective view of the cutter having the dual-purposed stopper/cover arranged at the foreside position according to the fifth embodiment.
Figure 46:
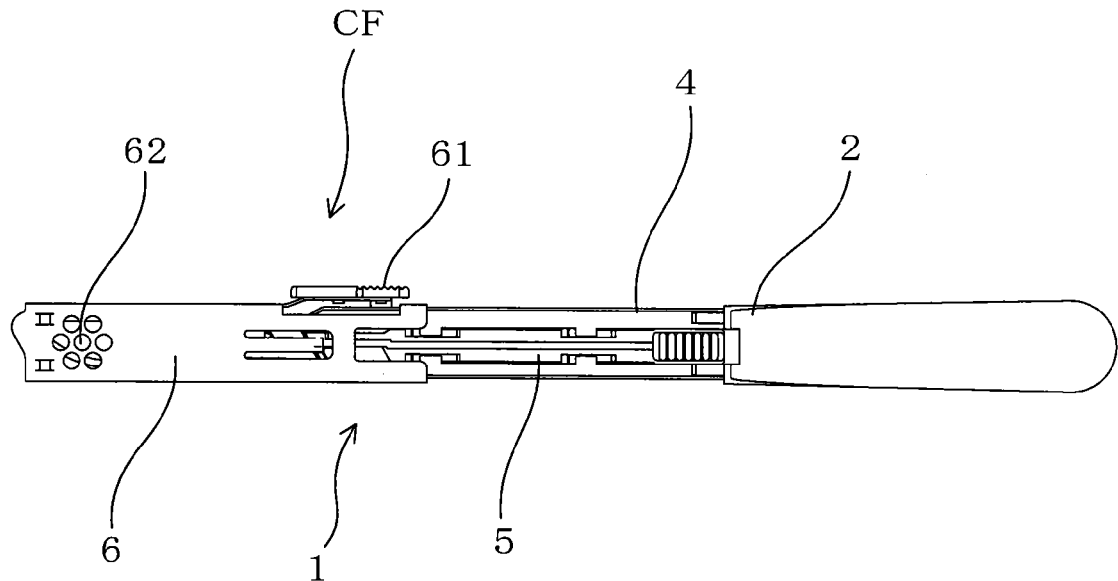
FIG. 46 is a front view of the cutter having the dual-purposed stopper/cover arranged at the foreside position according to the fifth embodiment.

In this embodiment also, as shown in FIG. 40 to FIG. 46, although the dual-purposed stopper/cover 6 is configured to have the back face lock section 61, its configuration slightly differs from that shown in the second embodiment. That is, in the present embodiment, as shown in FIG. 42, the lock member 610 is fixed to an upper face of the heightwise flat spring 611 formed on an upper face of the dual-purposed stopper/cover 6. The lock member 610 has formed therein the claw section 612 at a rear-side section of the back face plate 613 arranged along the upper face of the heightwise flat spring 611, where the claw section 612 extends downward from one end in the thickness direction X (back face side) and bends inward in the thickness direction X.

Thus, the back face lock section 61 is configured to include the heightwise flat spring 611 and the lock member 610 fixed thereto.

Figure 47:
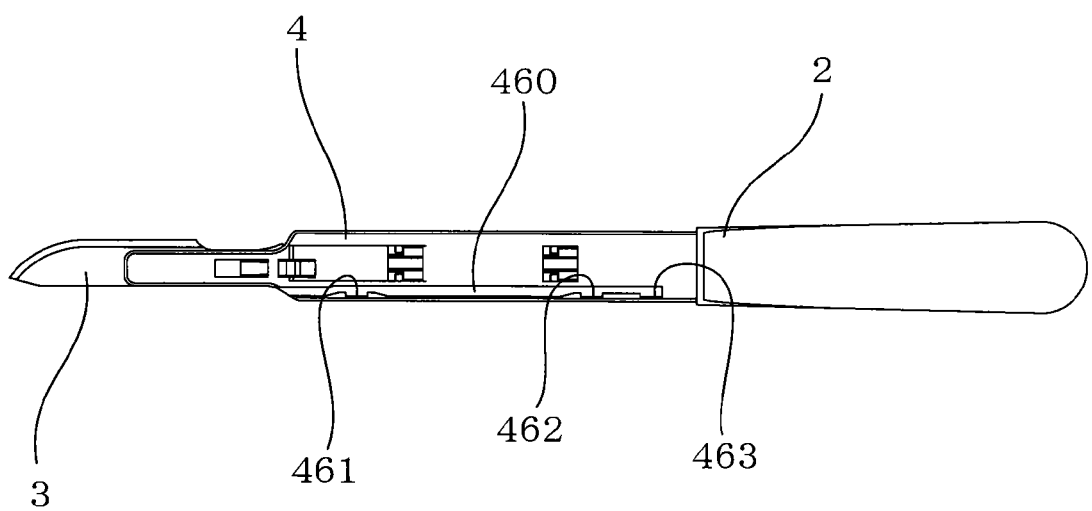
FIG. 47 is a rear face view of the cutter with the dual-purposed stopper/cover detached according to the fifth embodiment.

Further, in the present embodiment, as shown in FIG. 47, the slide groove section 460, the foreside connecting groove 461, the intermediate connecting groove 462, and the rear side connecting groove 463 are provided at the back face of the main body block 4. The dual-purposed stopper/cover 6 is locked at the foreside position CF (FIG. 45 and FIG. 46), the intermediate position CC (FIG. 43 and FIG. 44), or the rear side position CR (FIG. 40 to FIG. 42) by connecting the claw section 612 of the back face lock section 61 from the back side with the foreside connecting groove 461, the intermediate connecting groove 462, or the rear side connecting groove 463, respectively.

Other features are identical to those of the second embodiment.

In the present embodiment also, the identical advantageous effects as those of the second embodiment are obtained.

Sixth Embodiment

This embodiment is an example of a cutter 1 as shown in FIG. 48 to FIG. 64 in which the shape of a cutter body 2 is different from those of the first and third embodiments.

Figure 48:
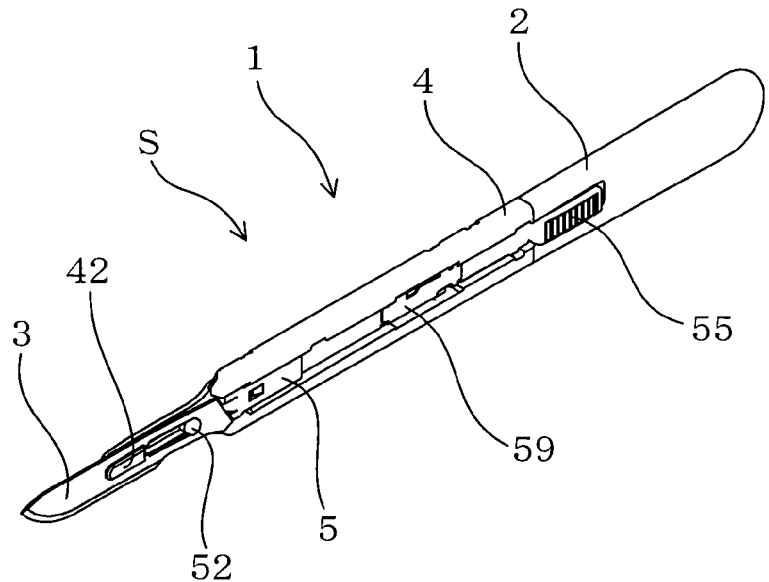
FIG. 48 is a perspective view of a cutter according to a sixth embodiment.
Figure 49:
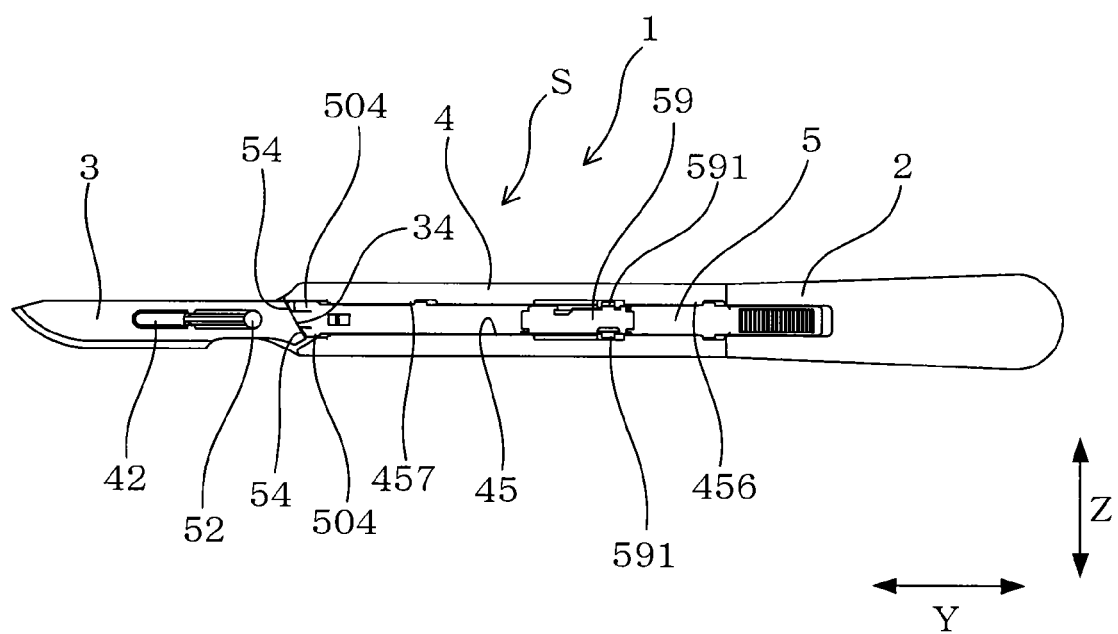
FIG. 49 is a front view of the cutter according to the sixth embodiment.
Figure 50:
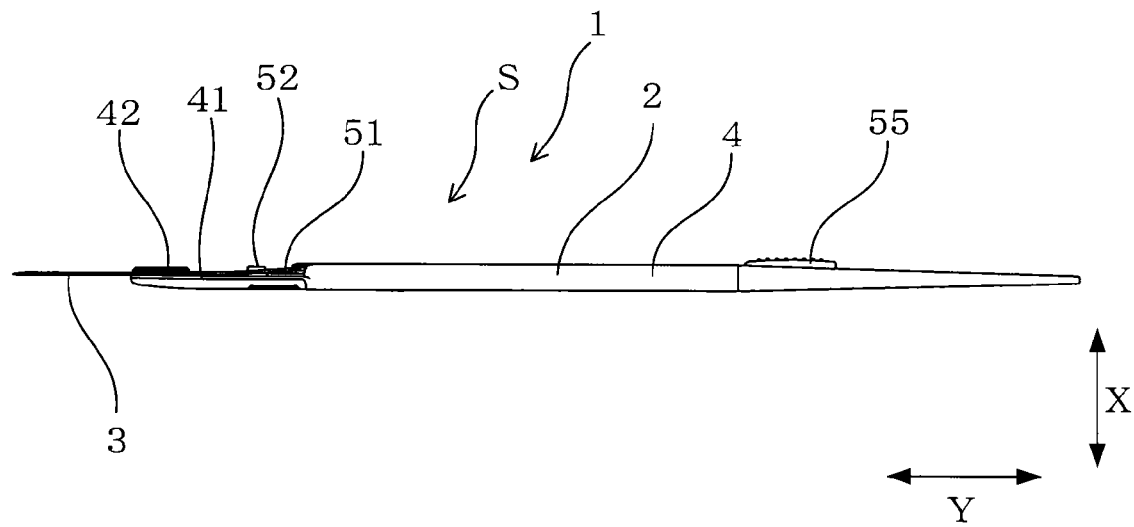
FIG. 50 is a bottom view of the cutter according to the sixth embodiment.
Figure 51:
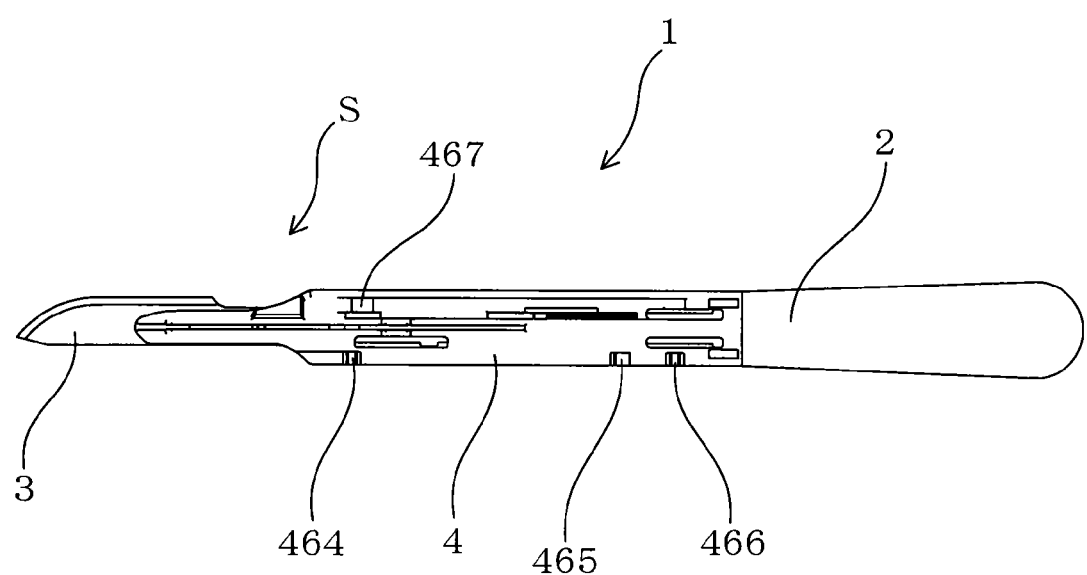
FIG. 51 is a rear face view of the cutter according to the sixth embodiment.
Figure 52:
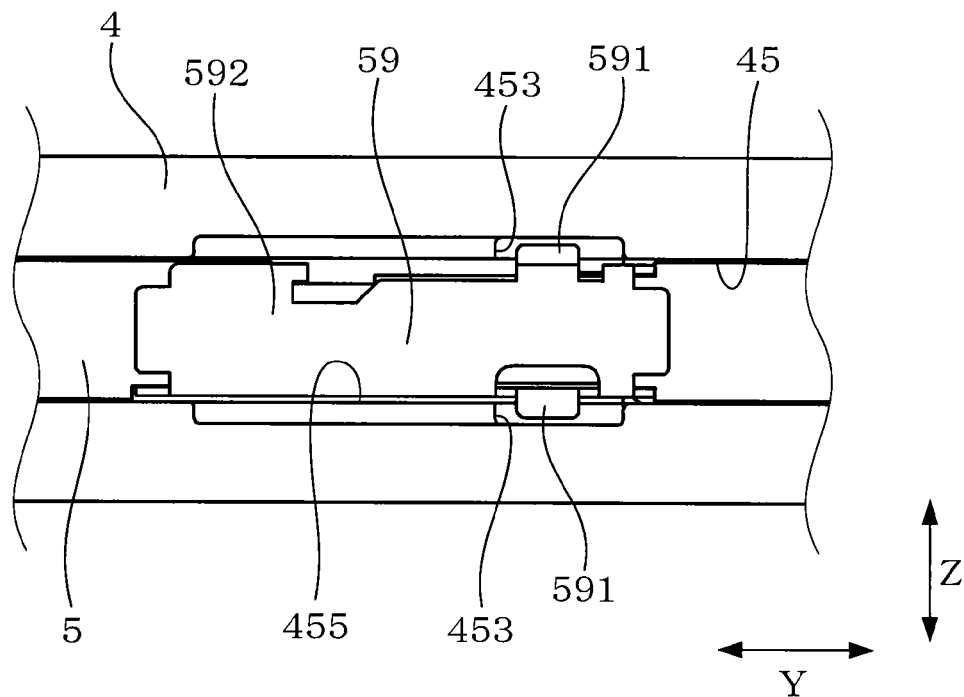
FIG. 52 is an explanatory diagram illustrating the function of a flat spring stopper according to the sixth embodiment.

In the cutter 1 of the present example, as shown in FIG. 48, FIG. 49 and FIG. 52, a flat spring stopper 59 capable of elastically deforming in the thickness direction X is fixed to the slide block 5. The flat spring stopper 59 includes a stopper protruding part 591 that protrudes in the height direction Z. Further, as shown in FIG. 52, it is configured that in the attached state S, the slide block 5 is prevented from moving forward with respect to the main body block 4 by the stopper protruding part 591 being connected with a stopper connecting section 453 provided in the main body block 4.

Figure 53:
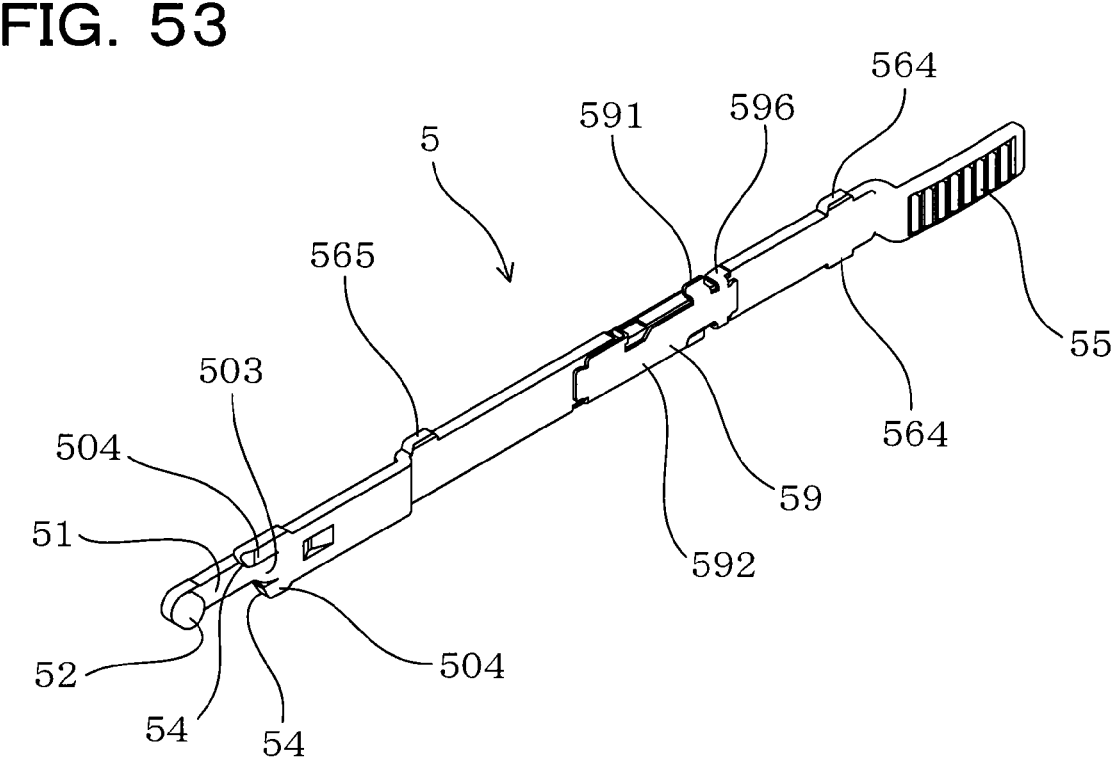
FIG. 53 is a perspective view of a slide block according to the sixth embodiment.
Figure 54:
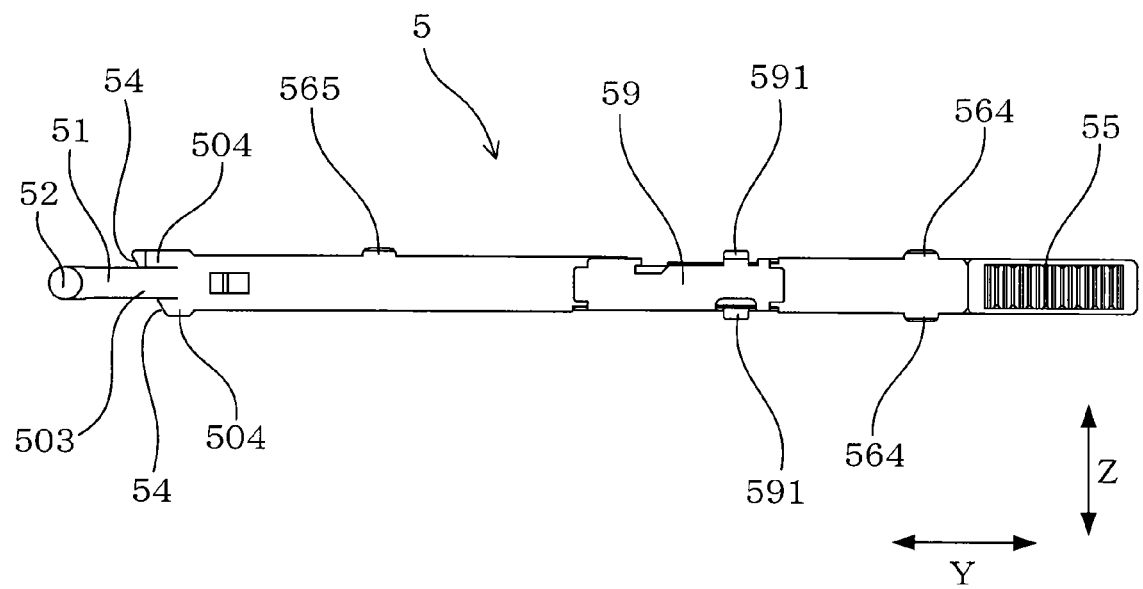
FIG. 54 is a front view of the slide block according to the sixth embodiment.
Figure 55:
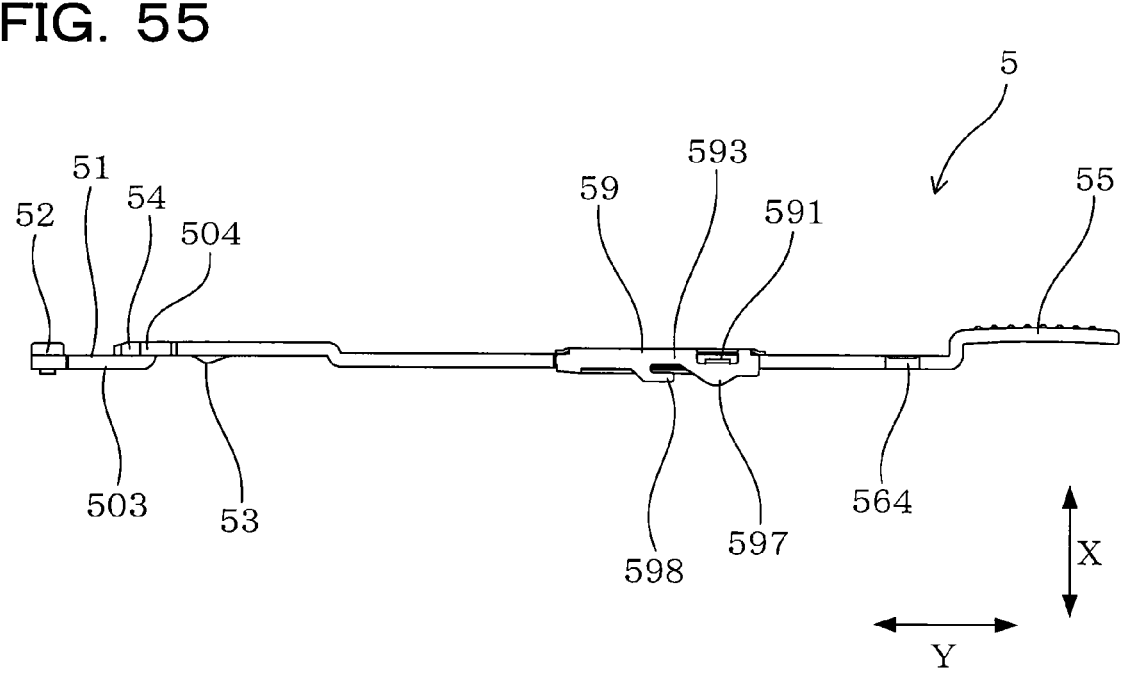
FIG. 55 is a bottom view of the slide block according to the sixth embodiment.
Figure 56:
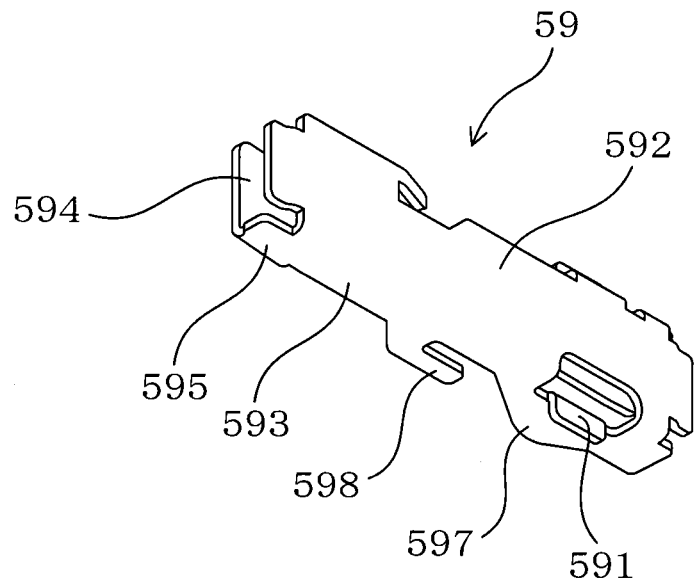
FIG. 56 is a perspective view of the flat spring stopper according to the sixth embodiment.
Figure 57:
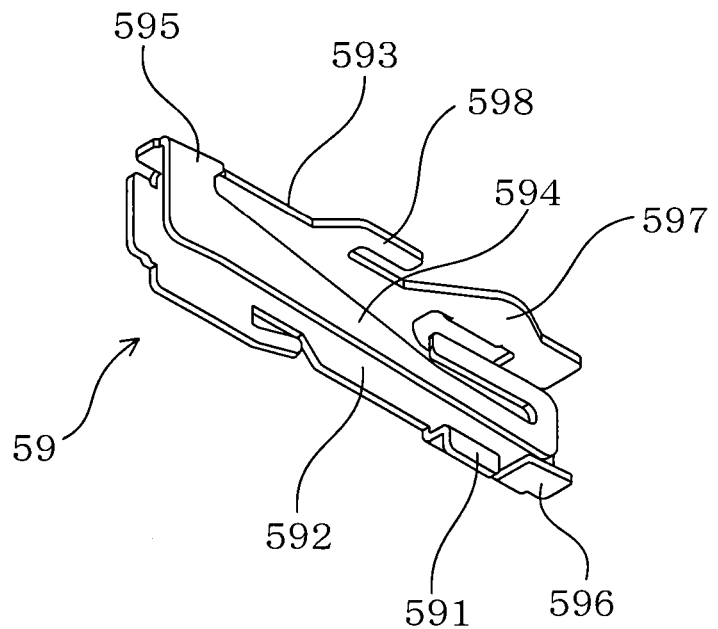
FIG. 57 is another perspective view of the flat spring stopper according to the sixth embodiment.
Figure 58:
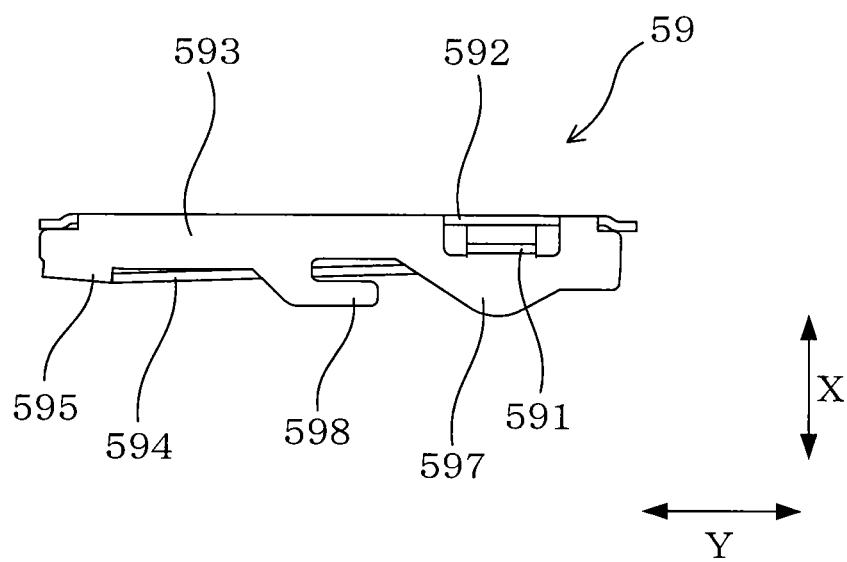
FIG. 58 is a bottom view of the flat spring stopper according to the sixth embodiment.
Figure 59:
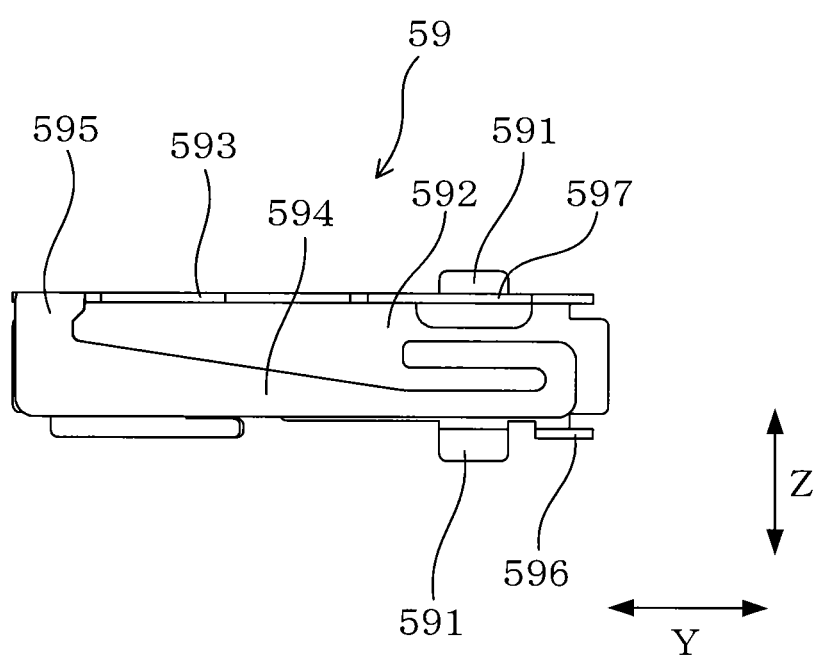
FIG. 59 is a rear face view of the flat spring stopper according to the sixth embodiment.

As shown in FIG. 53 to FIG. 55, the flat spring stopper 59 is fixed at a portion between the back side protruding section 53 and the operating section 55 of the slide block 5. Further, as shown in FIG. 56 to FIG. 59, the flat spring stopper 59 includes a front side plate 592 arranged along a front face, a back side plate 594 arranged along a back face, and a lower side plate 593 arranged along a lower face of the slide block 5, which are formed by bending one piece of metal plate. The lower side plate 593 and the back side plate 594 are coupled at a fore end section, and a slit is formed between them at a rear side of a coupled section 595 thereof.

An upper side engaging part 596 arranged along an upper face of the slide block 5 protrudes toward a back side in the thickness direction X from an upper edge of a rear end section of the front side plate 592. Further, a stopper protruding part 591 that bends toward the back side in the thickness direction X is protruding toward an upper side in the height direction Z from an upper edge of the front side plate 592. Further, another stopper protruding part 591 is protruding toward a lower side in the height direction Z from the lower side plate 593 so as to be paired with the aforementioned stopper protruding part 591.

Figure 63:
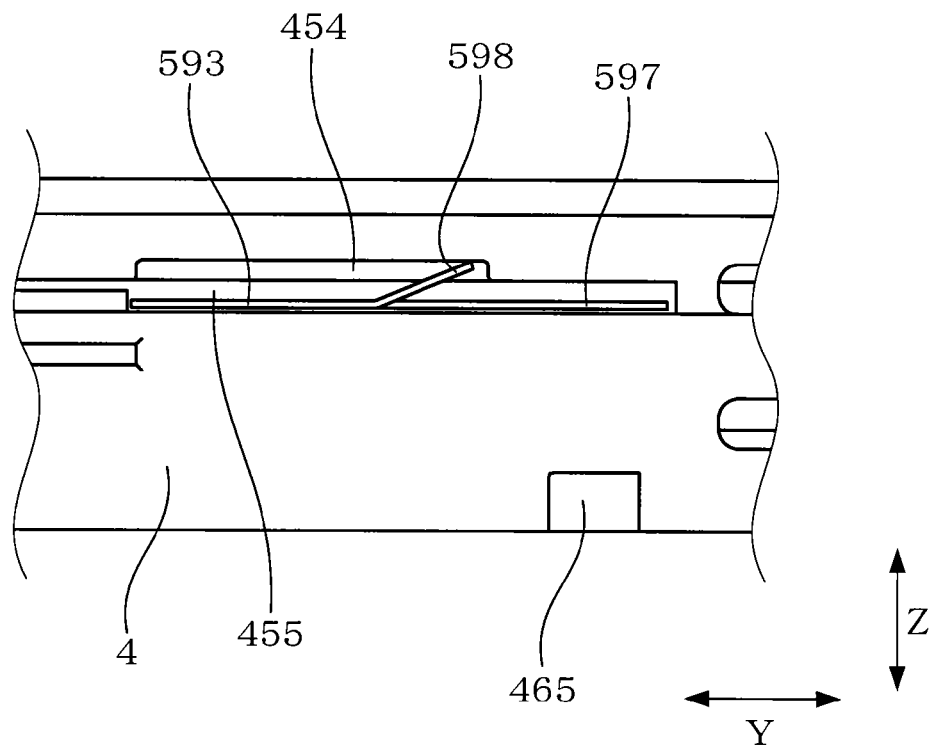
FIG. 63 is an explanatory diagram of a connected state of a back side connecting part with the thicknesswise connecting section according to the sixth embodiment.

Further, as shown in FIG. 55 to FIG. 58, the lower side plate 593 is configured to include a back face protruding section 597 in which a part of the lower side plate 593 in the vicinity of its rear end section is caused to protrude father out toward the back side than the back face of the slide block 5. Further, the lower side plate 593 includes a back side connecting part 598 configured to be capable of deforming in the height direction Z at between the back face protruding section 597 and the coupled section 595. As shown in FIG. 63, the back side connecting part 598 is configured to be capable of connecting with a thicknesswise connecting section 454 provided in the main body block 4 from the back face side. That is, the back side connecting part 598 protrudes further out toward the back side than the thicknesswise connecting section 454 of the slide block 5, and is configured to be capable of plastically deforming toward the lower side in the height direction Z (the upper side in the drawing of FIG. 63).

Figure 60:
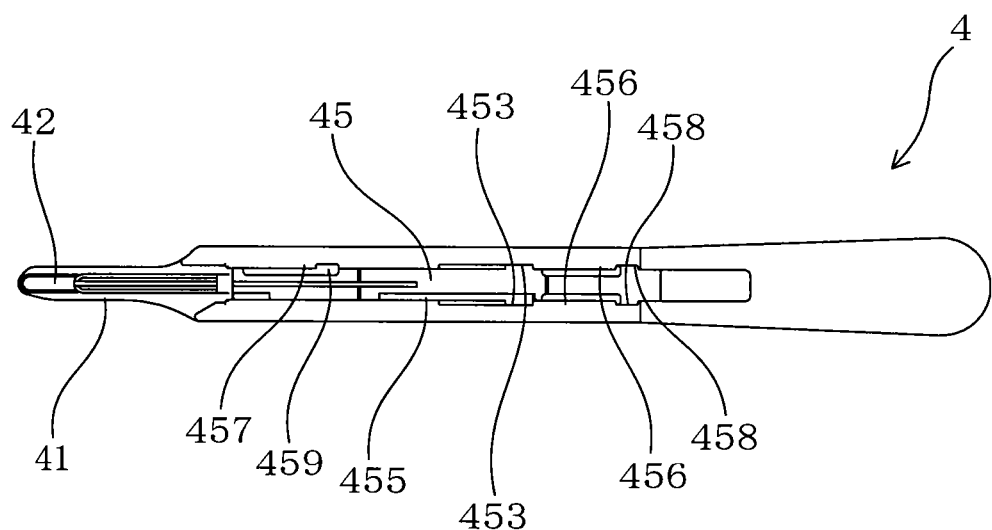
FIG. 60 is a front view of a main body block according to the sixth embodiment.
Figure 61:
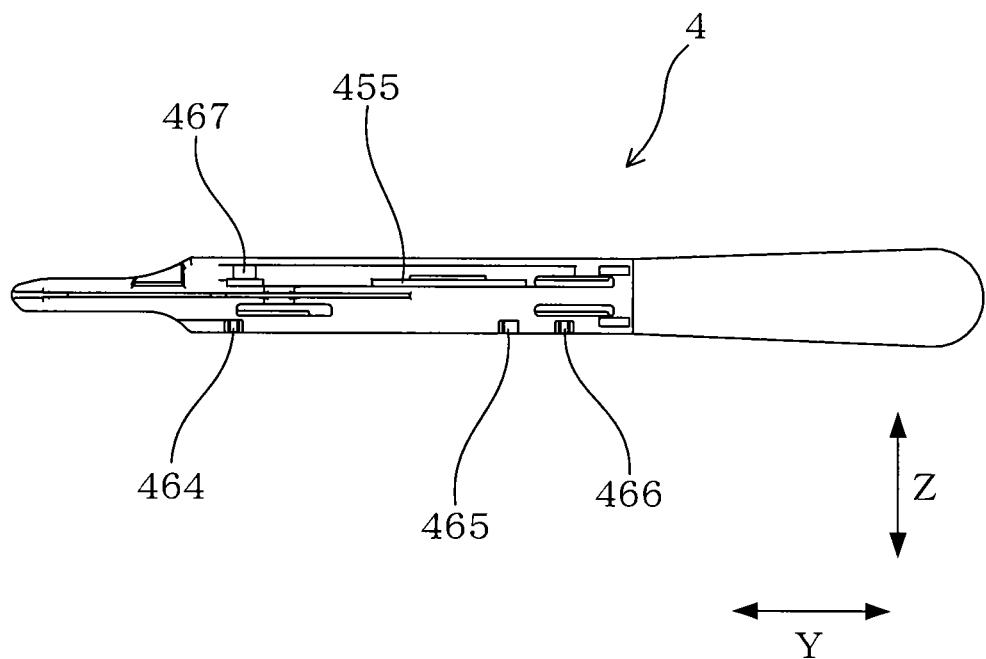
FIG. 61 is a rear face view of the main body block according to the sixth embodiment.
Figure 62:
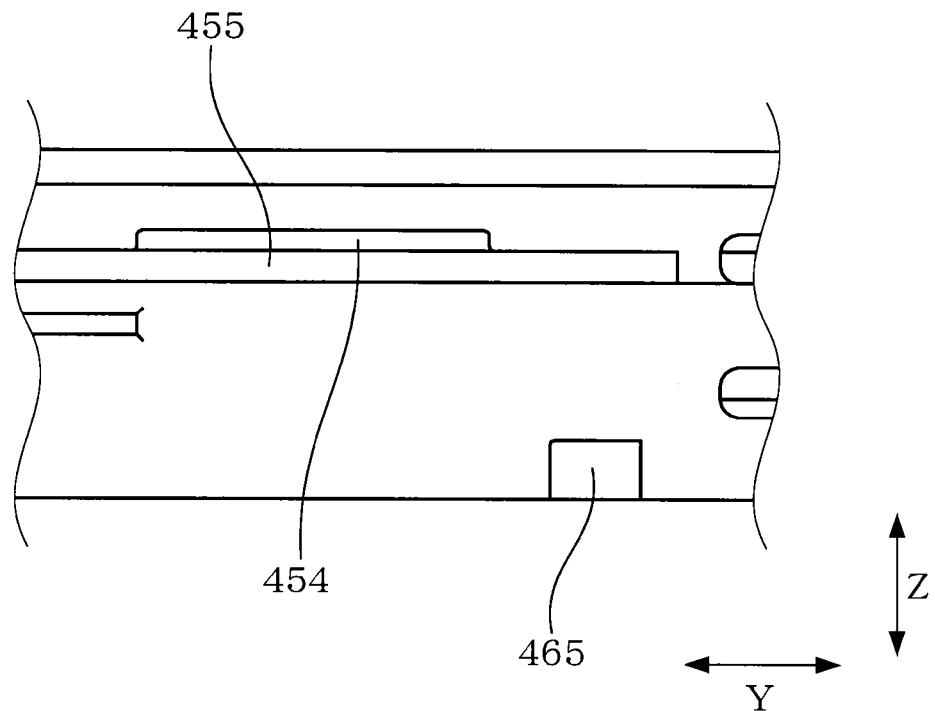
FIG. 62 is a rear face view of the main body block near a thicknesswise connecting section according to the sixth embodiment.

As shown in FIG. 60, the main body block 4 includes the stopper connecting sections 453 that are partially concaved toward the back side in the thickness direction X at both sides in the height direction Z of the container section 45. Further, at a position continuing from the stopper connecting section 453 on the lower side, a stopper slit 455 that penetrates the main body block 4 from its front to back and is elongated in the longitudinal direction Y is formed. Further, as shown in FIG. 61 and FIG. 62, at the back face of the main body block 4, the thicknesswise connecting section 454 that is elongated in the longitudinal direction Y and formed in the shape of a groove is formed at a position continuing from the stopper slit 455.

As shown in FIG. 49 and FIG. 52, in a state where the slide block 5, to which the flat spring stopper 59 is fixed, is attached to the container section 45 of the main body block 4, the pair of stopper protruding parts 591 of the flat spring stopper 59 connects with the pair of stopper connecting sections 453 of the main body block 4. Due to this, the forward movement of the slide block 5 with respect to the main body block 4 can be prevented.

Further, in this state, the back face protruding section 597 and the back side connecting part 598 of the flat spring stopper 59 are arranged in the stopper slit 455. In this state, the flat spring stopper 59 is not elastically deformed. Further, by plastically deforming the back side connecting part 598 arranged in the stopper slit 455 toward the lower side in the height direction Z, the back side connecting part 598 can be connected with the thicknesswise connecting section 454 of the main body block 4.

Figure 64:
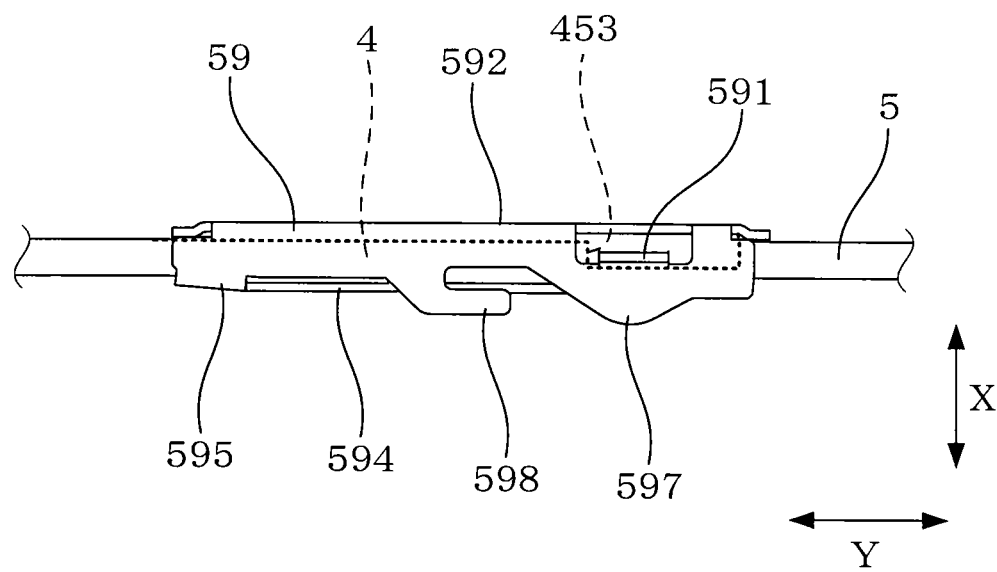
FIG. 64 is a bottom view of the flat spring stopper fixed to the main body block according to the sixth embodiment, where (A) is in an attached state, and (B) is a state at the time of releasing the stopper.
Figure 64:
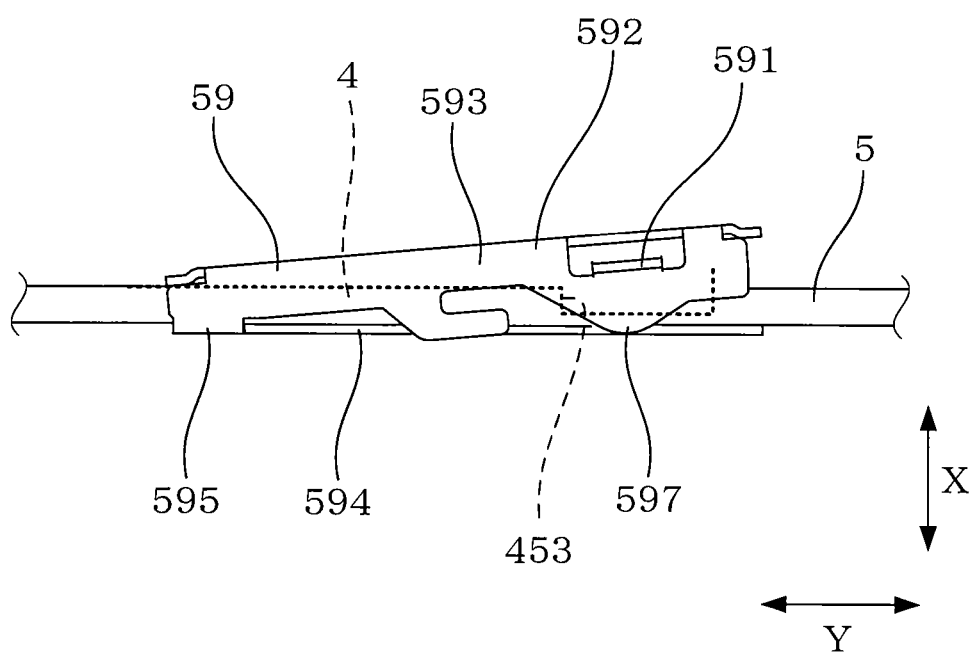
Figure 65:
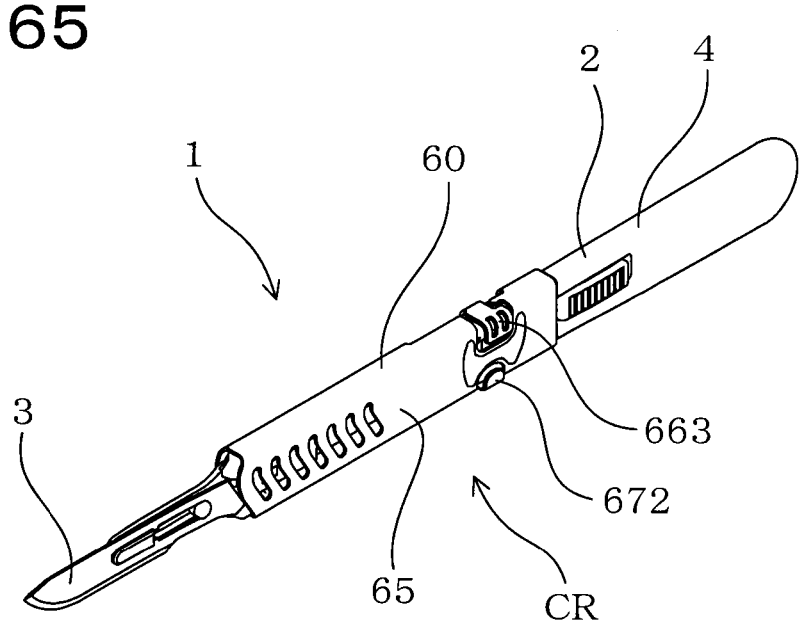
FIG. 65 is a perspective view of a cutter having a spring-integrated cover arranged at the rear-side position according to a seventh embodiment.
Figure 66:
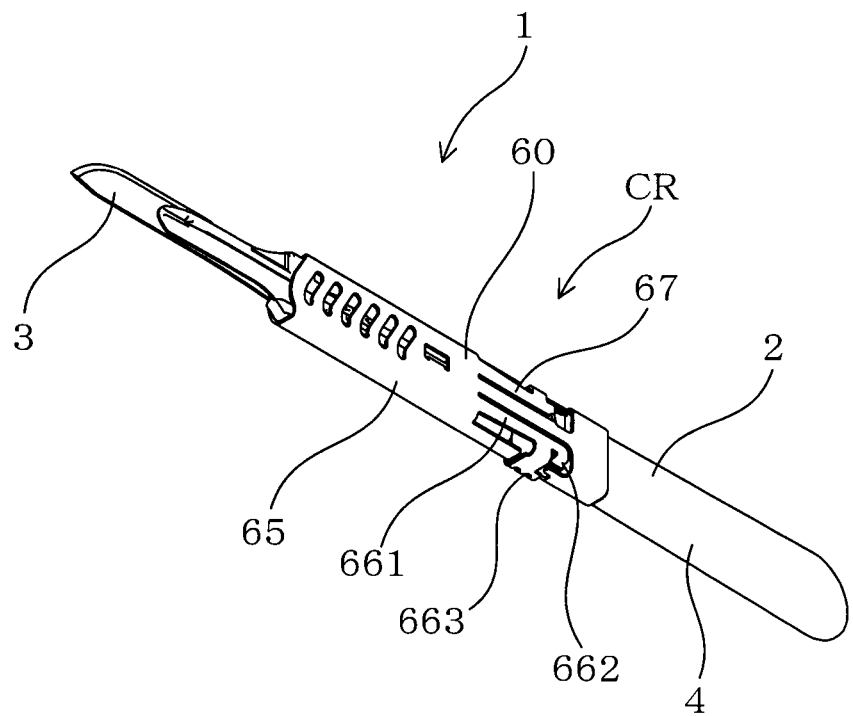
FIG. 66 is another perspective view of the blade having the spring-integrated cover arranged at the rear-side position according to the seventh embodiment.
Figure 67:
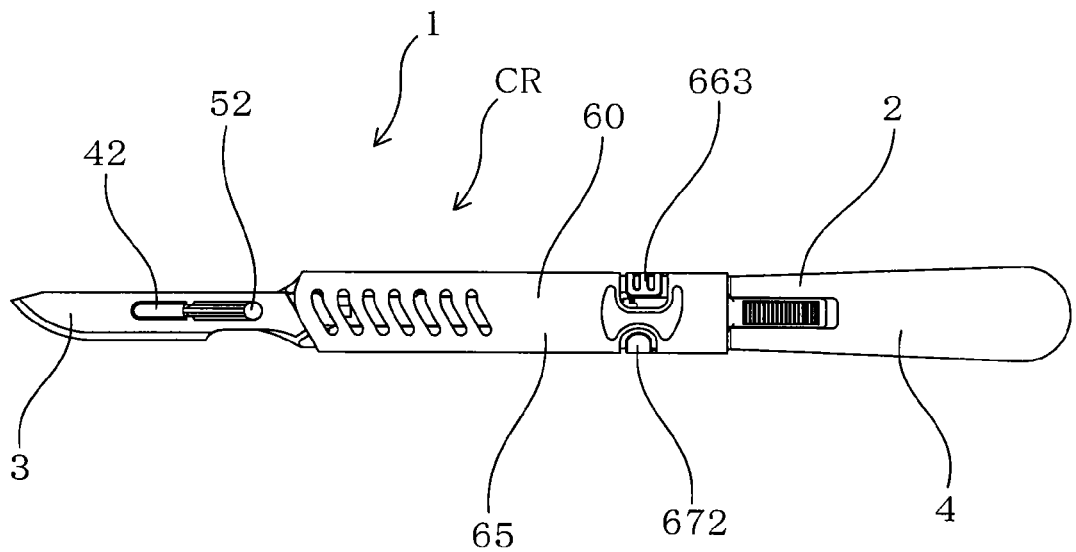
FIG. 67 is a front view of the cutter having the spring-integrated cover arranged at the rear-side position according to the seventh embodiment.
Figure 68:
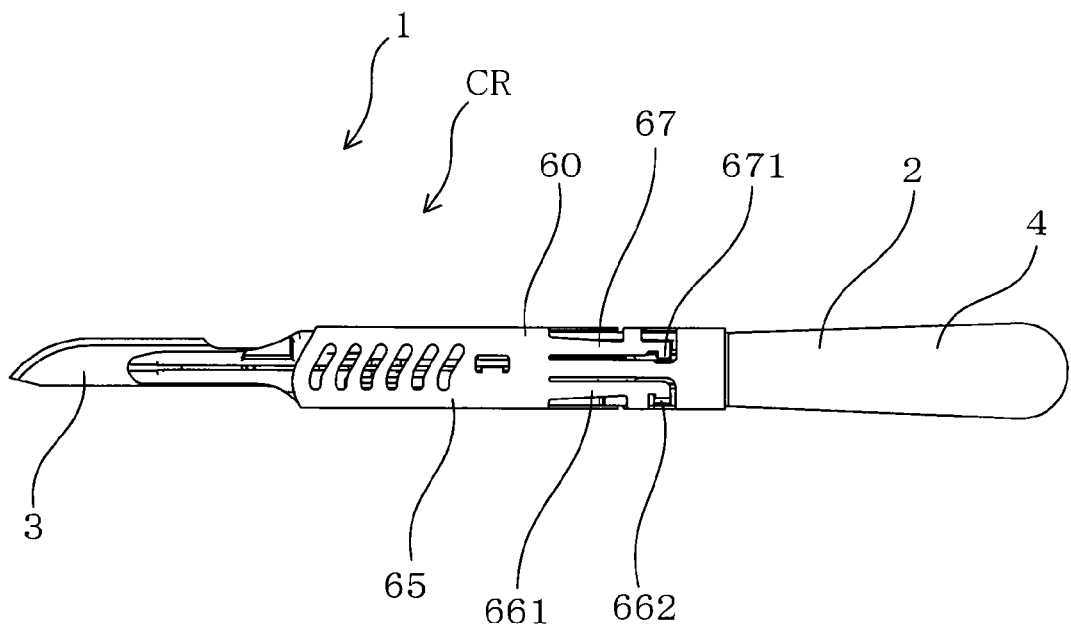
FIG. 68 is a rear face view of the cutter having the spring-integrated cover arranged at the rear-side position according to the seventh embodiment.

Moreover, as shown in FIG. 64, the flat spring stopper 59 elastically deforms in the vicinity of the coupled section 595 by having the back face protruding section 597 being pushed up from the back side toward the front side. Due to this, other portions move toward the front side with respect to the back side plate 594. Since the back side plate 594 is supported at the back face of the slide block 5, other portions of the flat spring stopper 59 moves so as to float toward the front side from the slide block 5. Due to this, the pair of stopper protruding parts 591 moves toward the front side, and is detached from the pair of stopper connecting sections 453. Due to this, the slide block 4 is allowed to move forward with respect to the main body block 5.

As shown in FIG. 53 to FIG. 55, the slide block 5 is diverged into a center part 503 and a pair of diverged parts 504 at a position on the fore side than the back side protruding section 53, where the pair of diverged parts 504 is arranged at both sides of the center part 503 in the height direction Z.

The center part 503 includes the rear side supporting section 51 and the slide connecting section 52. That is, the rear side supporting section 51 is formed so as to extend forward at a position retracted toward the back face side in the thickness direction X from the diverging portion, and the slide connecting section 52 is formed at a fore end section of the rear side supporting section 51 so as to protrude toward the front side in the thickness direction X.

The pair of diverged parts 504 is arranged at both sides of the center part 503 in the height direction Z, and extends forward. Further, the rear side opposing faces 54 that oppose the rear end 34 of the replaceable blade 3 are formed at the fore ends of this pair of diverged parts 504.

Of the pair of diverged parts 504, the diverged part 504 on the upper side in the height direction Z is longer than the diverged part 504 on the lower side. Further, the rear side opposing faces 54 formed respectively thereon are formed on the substantially same plane. Further, the rear side opposing faces 54 are obliquely formed with respect to the longitudinal direction Y and the height direction Z, and are formed parallel to the thickness direction X. That is, the pair of rear side opposing faces 54 is formed so as to be substantially parallel to the oblique rear end 34 of the replaceable blade 3.

Further, the rear side opposing faces 54 of the diverged parts 504 are formed as end surfaces of the slide block 5. That is, where the slide block 5 is formed through punching or machining, the rear side opposing faces 54 are obtained as processed ends.

When the slide block 5 is moved forward with respect to the main body block 4, the replaceable blade 3 is pushed out forward by the pair of rear side opposing faces 54 pressing the rear end 34 of the replaceable blade 3.

Further, the slide block 5 in the cutter 1 of the present embodiment includes a pair of rear side wing sections 564 that respectively protrudes in both ways in the height direction Z at between the portion where the flat spring stopper 59 is fixed and the operating section 55. Further, the slide block 5 includes a foreside wing section 565 that protrudes upward in the height direction Z at between the portion where the flat spring stopper 59 is fixed and the back side protruding section 53.

As shown in FIG. 60, the main body block 4 has a pair of rear side front face engaging sections 456 with which the pair of backside wing sections 564 is slidably engaged from the front side. Further, the main body block 4 has a foreside front face engaging section 457 with which the foreside wing section 565 in the slide block 5 is slidably engaged from the front side. Further, rear side retracting concave sections 458 that are adjacent to the rear sides of the rear side front face engaging sections 456, and retracted in the height direction Z are formed, and a foreside retracting concave section 459 that is adjacent to the rear side of the foreside front face engaging section 456 and retracted in the height direction Z is formed. When attaching or detaching the slide block 5 to or from the main body block 4, the pair of rear side wing sections 564 is correspondingly arranged in the pair of rear side retracting concave sections 458, and the foreside wing section 565 is arranged in the foreside retracting concave section 459.

Further, the container section 45 of the main body block 4 in the cutter 1 of the present embodiment is formed in a substantially concaved shape and includes a bottom face section on the back side as its basic configuration. A part of the bottom face section is penetrated from the front to the back by a plurality of slits including the stopper slit 455.

The slide block 5 is supported at its front and back by the bottom face section of the container section 45, the rear side front face engaging sections 456, and the foreside front face engaging section 457 at the pair of rear side wing sections 564 and the foreside wing section 565.

The others are identical to those of the first embodiment.

In the case of the present embodiment, the movement of the slide block 5 in the attached state S can surely be prevented by the flat spring stopper 59. Further, as shown in FIG. 64, by elastically deforming the flat spring stopper 59 in the thickness direction X, the connected state of the stopper protruding parts 591 with respect to the stopper connecting section 453 can easily be ended. Due to this, the slide block 5 is allowed to move forward with respect to the main body block 4.

Further, the flat spring stopper 59 includes the back side connecting part 598, and as shown in FIG. 63, is configured to connect with the thicknesswise connecting section 454 provided in the main body block 4 from the back face side by voluntarily deforming the back side connecting part 598 by bending. Due to this, in the state where the replaceable blade 3 is detached from the cutter body 2, the slide block 5 can be prevented from falling off of the main body block 4. For example, where the replaceable blade 3 is detached to store or wash the cutter body 2, the slide block 5 is prevented from being taken off of the main body block 4. Due to this, handling of the cutter body 2 becomes easy.

Further, as shown in FIG. 53 to FIG. 55, the slide block 5 diverges into the center part 503 and the pair of diverged parts 504 at the foreside of the back side protruding section 53, and the rear side opposing faces 54 are formed at the fore ends of the pair of diverged parts 504. Due to this, it becomes easy to make the rear side opposing faces 54 stably contact with the rear end 34 of the replaceable blade 3. That is, since the pair of diverged parts 504 is formed at portions different from the center part 503, the fore ends of these diverged parts 504 can be processed as end faces. Due to this, by forming the rear side opposing faces 54 at the fore ends of these diverged parts 504, the rear side opposing faces 54 can be formed as faces parallel to the thickness direction X of the replaceable blade 3. As a result, the rear side opposing faces 54 can make stable contact with the rear end 34 of the replaceable blade 3, and when the slide block 5 is moved forward with respect to the main body block 4, the replaceable blade 3 can stably be pushed out forward.

Thus, if the diverged parts 504 are not formed, for example as in the first embodiment (FIG. 3), the rear side opposing face 54 is to be formed to stand on the front face side of 51 by bending. In this case, it becomes difficult to accurately make the rear side opposing face 54 parallel to the thickness direction X, so that there is a possibility that a contacting state of the rear side opposing face 54 to the rear end 34 of the replaceable blade 3 is difficult to be maintained stably. Contrary to this, by providing the diverged parts 504 to form the rear side opposing faces 54 at the fore ends thereof, as aforementioned, it becomes easy to stably maintain the contacting state of the rear side opposing faces 54 to the rear end 34 of the replaceable blade 3.

Other advantageous effects are identical to those of the first embodiment.

Seventh Embodiment

As shown in FIG. 65 to FIG. 78, the present embodiment is an example in which a spring-integrated cover 60 is attached slidably in the longitudinal direction Y to the main body block 4 in the cutter 1 of the sixth embodiment (FIG. 48 to FIG. 51).

The spring-integrated cover 60 includes a cylindrical cover main body 65 that opens at both ends in the longitudinal direction Y, a flat spring section 661 extending in the longitudinal direction Y and capable of elastically deforming in the thickness direction X, and a lock claw 662 provided at a movable end of the flat spring section 661. These are integrally formed by one metal plate.

As shown in FIG. 61, the main body block 4 includes a foreside connecting concave section 464, a rear side connecting concave section 466, and an intermediate connecting concave section 465, concaved in the thickness direction X at three positions in the longitudinal direction Y, respectively. Further, the lock claw 662 can connect with the foreside connecting concave section 464, the rear side connecting concave section 466, or the intermediate connecting concave section 465. Due to this, the spring-integrated cover 60 can be locked at the foreside position CF in which the replaceable blade 3 is covered (FIG. 71 and FIG. 72), the rear side position CR in which the replaceable blade 3 is significantly exposed (FIG. 67 and FIG. 68), or the intermediate position CC between the foreside position CF and the rear side position CR (FIG. 69 and FIG. 70), respectively.

The foreside connecting concave section 464, the intermediate connecting concave section 465, and the rear side connecting concave section 466 are respectively formed at three positions in the longitudinal direction Y at an upper end section in the height direction Z at a back face of the main body block 4.

Figure 73:
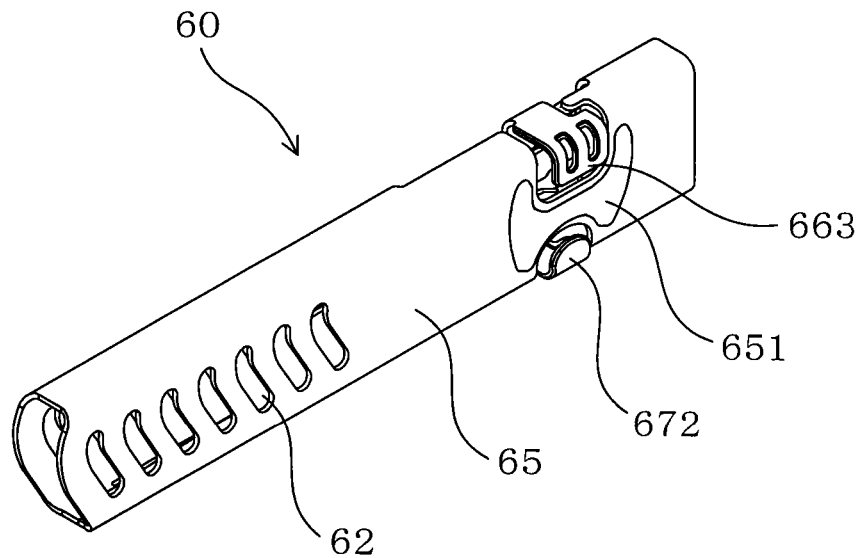
FIG. 73 is a perspective view of the spring-integrated cover according to the seventh embodiment.
Figure 74:
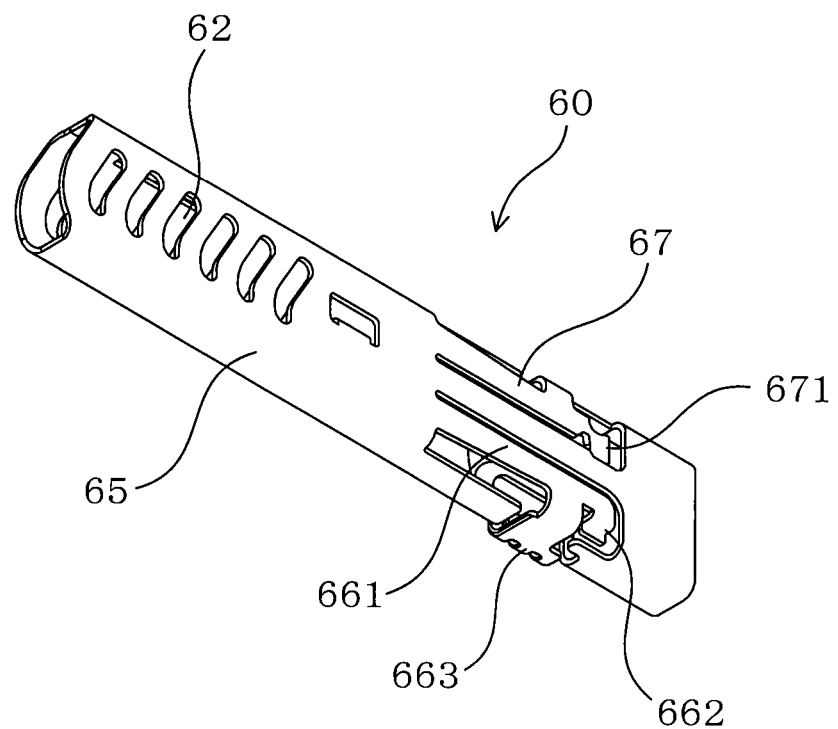
FIG. 74 is another perspective view of the spring-integrated cover according to the seventh embodiment.
Figure 75:
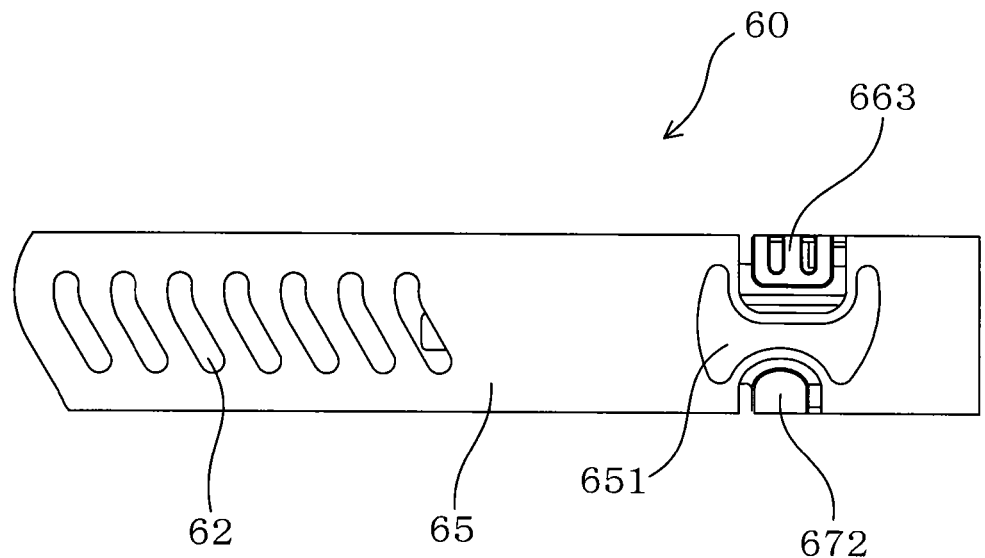
FIG. 75 is a front view of the spring-integrated cover according to the seventh embodiment.
Figure 77:
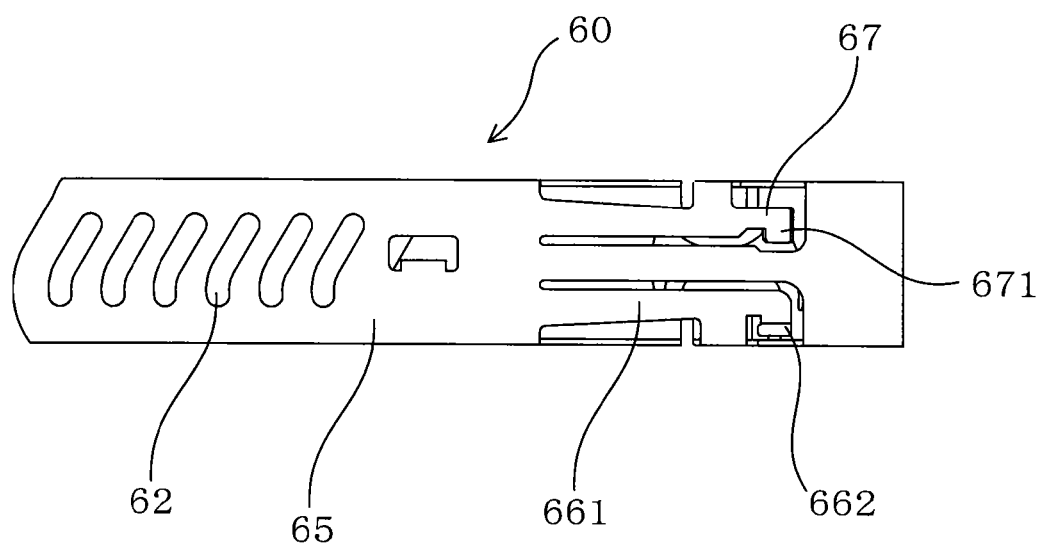
FIG. 77 is a rear face view of the spring-integrated cover according to the seventh embodiment.

As shown in FIG. 74 and FIG. 77, the flat spring section 661 is formed at a back side portion of the cover main body 65 of the spring-integrated cover 60 so as to extend from the foreside toward the backside in the longitudinal direction Y. Further, at a rear end section of the flat spring section 661, the lock claw 662 protrudes toward the front side (main body block 4 side). As shown in FIG. 73 to FIG. 75, the flat spring section 661 is provided with a claw pressing section 663 that stands toward the front side from the upper end of the spring-integrated cover 60 and protrudes further toward the front side than the face of the cover main body 65.

Figure 76:
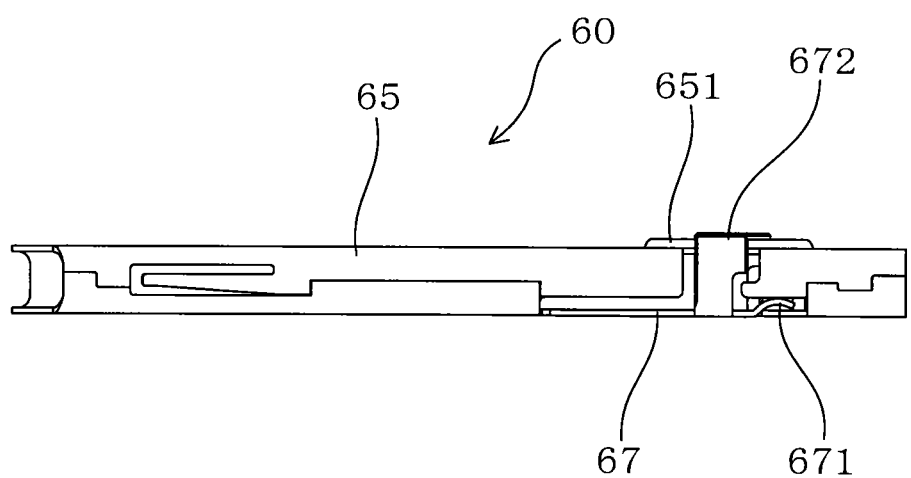
FIG. 76 is a bottom view of the spring-integrated cover according to the seventh embodiment.

Further, as shown in FIG. 74, FIG. 76 and FIG. 77, the spring-integrated cover 60 includes a stopper releasing part 67 formed to extend from the foreside toward the rear side in the longitudinal direction Y at the back side portion of the cover main body 65. The stopper releasing part 67 is formed substantially parallel to the flat spring section 661 below the flat spring section 661 (upper side in the drawings of FIG. 74 and FIG. 77). The stopper releasing part 67 protrudes toward the front side (main body block 4 side) in the thickness direction X at a back end section 671 thereof. Further, as shown in FIG. 73 to FIG. 76, the stopper releasing part 67 is provided with a releasing part pressing section 672 that stands toward the front side from the lower end of the spring-integrated cover 60 and protrudes further toward the front side than the front face of the cover main body 65.

The cover main body 65 is configured to include a bulge section 651 that partially protrudes toward the front side between the releasing part pressing section 672 and the claw pressing section 663.

The bulge section 651 has a function to suppress the stopper releasing part 67 and the lock claw 662 from concurrently being greatly displaced when a user attempts to press the releasing part pressing section 672 or the claw pressing section 663 with one's finger, and both the releasing part pressing section 672 and the claw pressing section 663 are concurrently pressed.

Further, window sections 62 are formed at the front side and the back side of the cover main body 65, similar to the second embodiment.

The cover main body 65, the flat spring section 661, the lock claw 662, and the stopper releasing part 67 are integrally formed by one metal plate.

Figure 69:
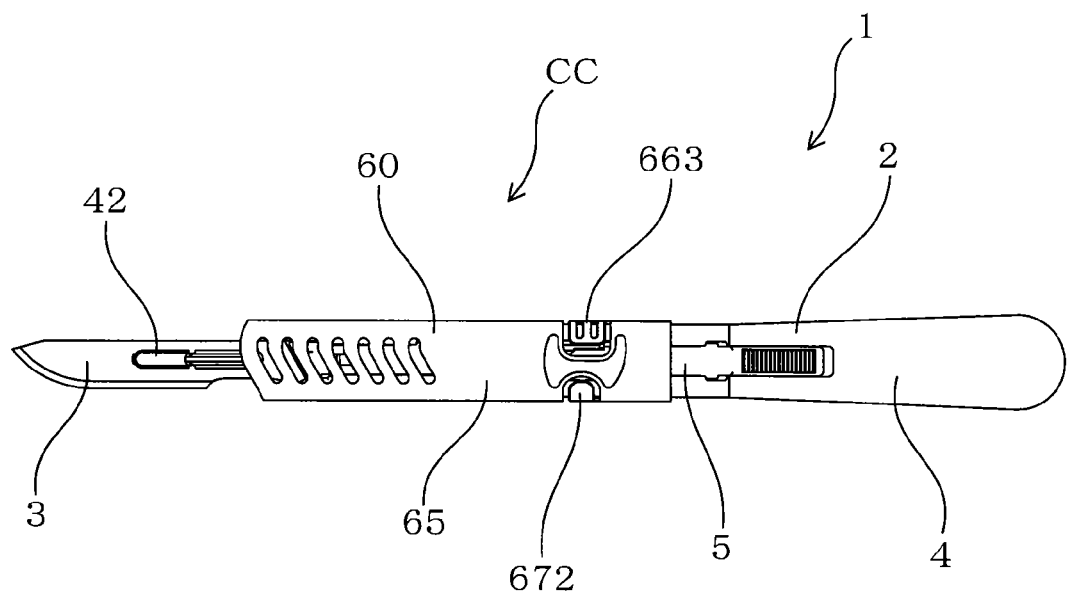
FIG. 69 is a front view of the cutter having the spring-integrated cover arranged at the intermediate position according to the seventh embodiment.
Figure 70:
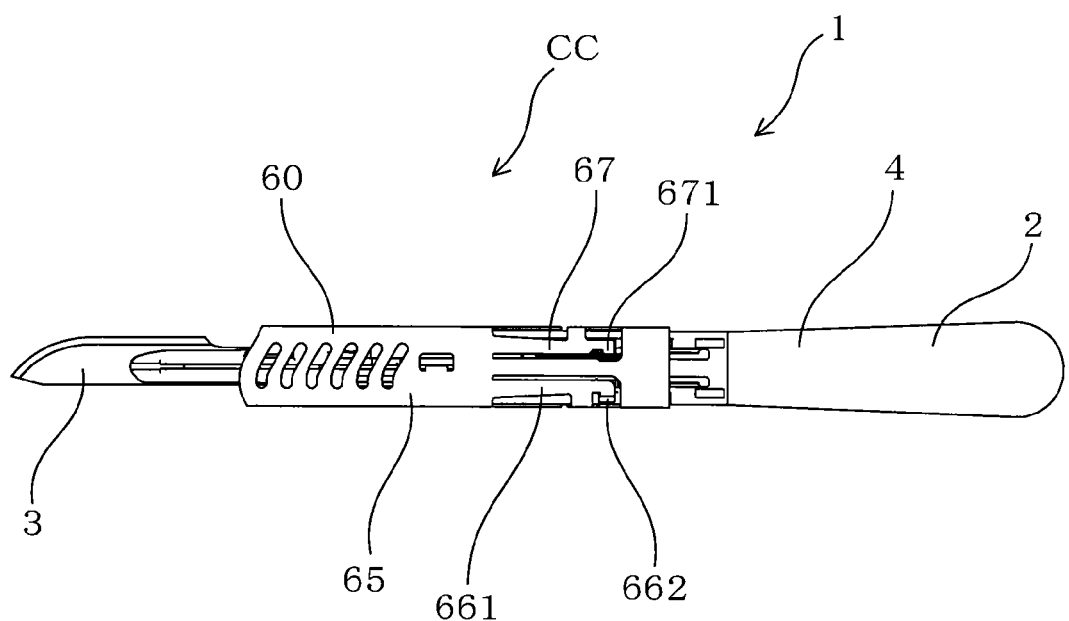
FIG. 70 is a rear face view of the cutter having the spring-integrated cover arranged at the intermediate position according to the seventh embodiment.
Figure 78:
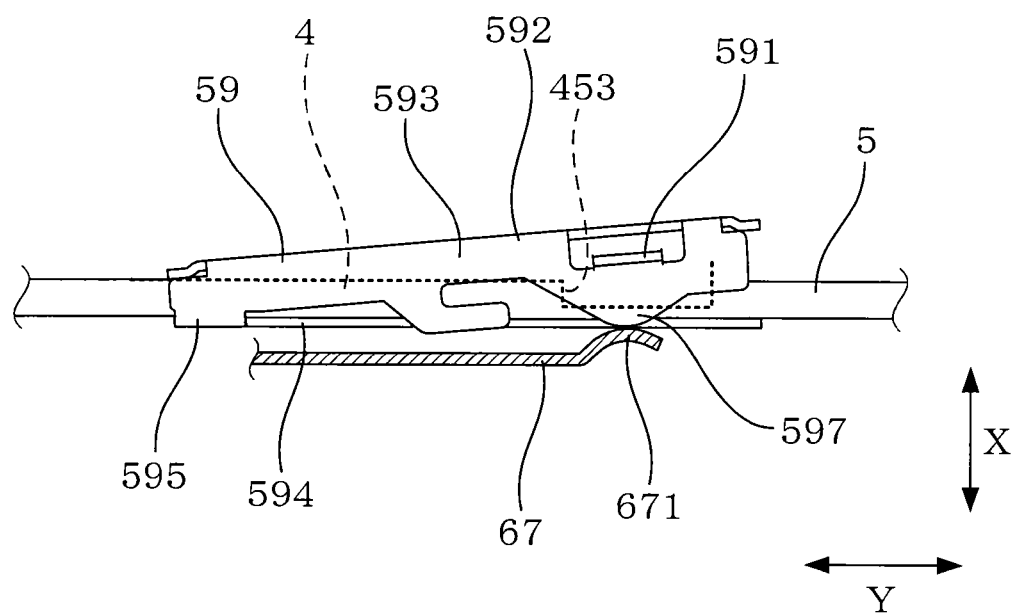
FIG. 78 is an explanatory diagram illustrating the function of a stopper releasing part according to the seventh embodiment.

As shown in FIG. 69 and FIG. 70, the stopper releasing part 67 is configured to allow the flat spring stopper 59 to elastically deform in the thickness direction X in a state where the spring-integrated cover 60 is locked with respect to the main body block 4 at the intermediate position CC. That is, in the state where the spring-integrated cover 60 is locked with respect to the main body block 4 at the intermediate position CC, as shown in FIG. 78, the stopper releasing part 67 is arranged at a position in which it would press the back face protruding section 597 of the flat spring stopper 59 from the rear side. Due to this, portions of the flat plate stopper 59 except for the back side plate 594 are elastically deformed so as to flow toward the front side. As a result of this, the pair of stopper protruding parts 591 is moved toward the front side, and is detached from the pair of stopper connecting sections 453 of the main body block 4.

Further, as shown in FIG. 61, a releasing part connecting concave section 467 with which the stopper releasing part 67 is connected when the spring-integrated cover 60 is at the foreside position CF (FIG. 71 and FIG. 72) is formed at the back face of the main body block 4. The movement of the spring-integrated cover 60 toward the foreside is restricted by the lock claw 662 connecting to this releasing part connecting concave section 467.

In the present embodiment, when the cutter 1 is used, as shown in FIG. 65 to FIG. 68, the spring-integrated cover 60 is locked at the rear side position CR. In this state, the lock claw 662 of the spring-integrated cover 60 is connected with the rear side connecting concave section 466 (see FIG. 61).

Further, when the replaceable blade 3 is replaced, as shown in FIG. 69 and FIG. 70, the spring-integrated cover 60 is locked at the intermediate position CC. In this state, the lock claw 662 is connected with the intermediate connecting concave section 465 of the main body block 4 (see FIG. 61). Further, as shown in FIG. 78, the stopper releasing part 67 of the spring-integrated cover 60 presses the back face protruding section 597 of the flat spring stopper 59 from the back side toward the front side, and causes the flat spring stopper 59 to elastically deform. Due to this, the stopper protruding part 591 is detached from the stopper connecting section 453, whereby a stopper function of the flat spring stopper 59 is released, and the slide block 5 is allowed to move forward.

Thus, in this state, the replaceable blade 3 can be detached and another replaceable blade 3 can be attached by moving the operating section 55 forward.

Figure 71:
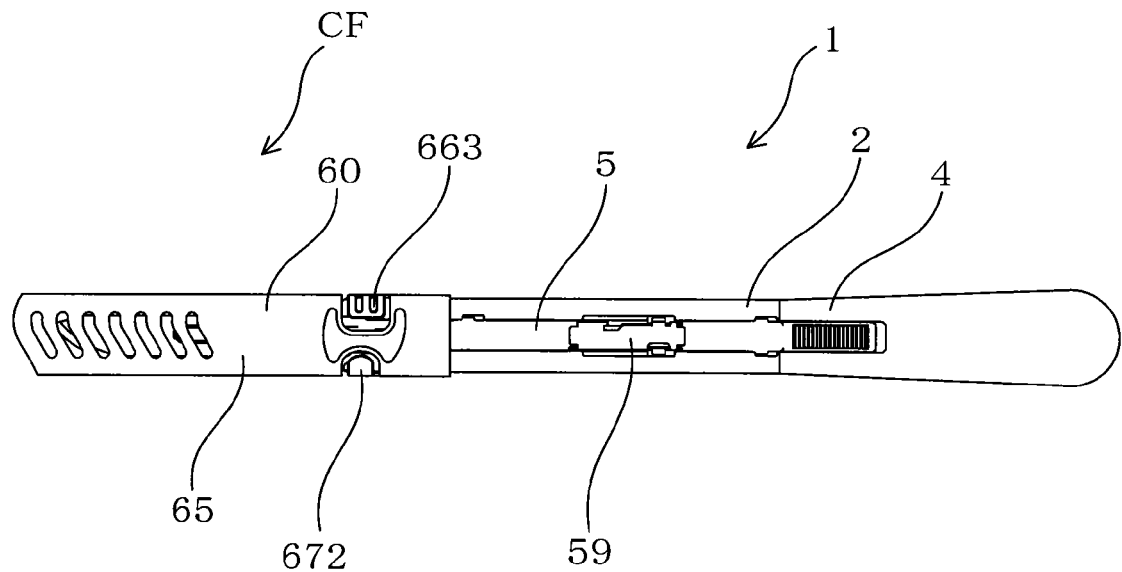
FIG. 71 is a front view of the cutter having the spring-integrated cover arranged at the foreside position according to the seventh embodiment.
Figure 72:
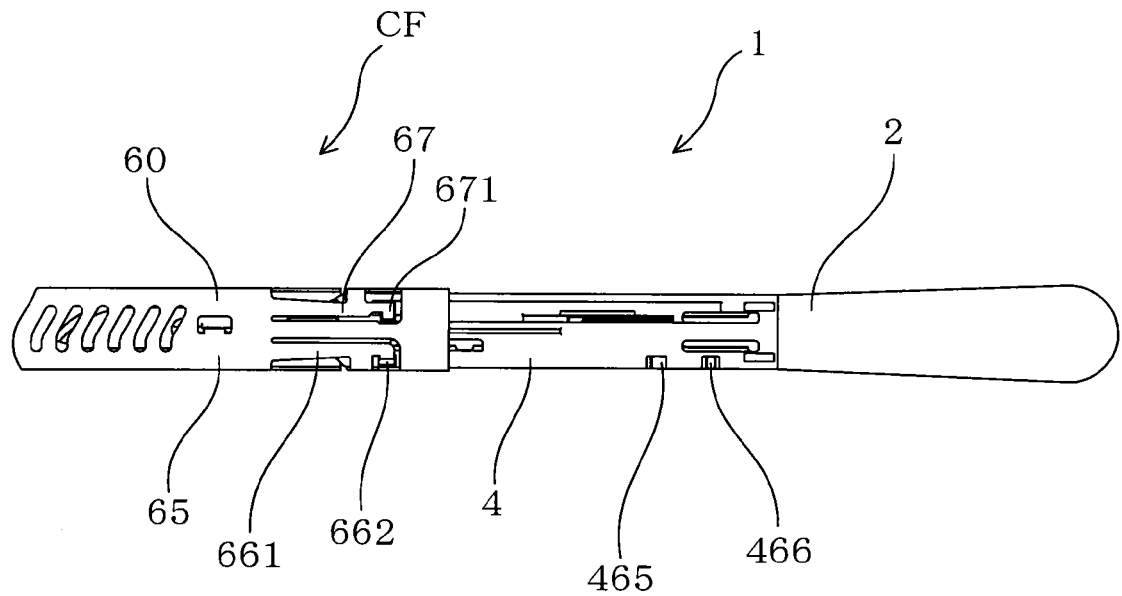
FIG. 72 is a rear face view of the cutter having the spring-integrated cover arranged at the foreside position according to the seventh embodiment.

Further, when the cutter 1 is not used, as shown in FIG. 71 and FIG. 72, the spring-integrated cover 60 is locked at the foreside position CF. In this state, the lock claw 662 of the spring-integrated cover 60 is connected with the foreside connecting concave section 464 (see FIG. 61). In this occasion, the stopper releasing part 67 is connected with the releasing part connecting concave section 467 of the main body block 4 (see FIG. 61). Due to this, the spring-integrated cover 60 is restricted from moving further forward with respect to the main body block 4.

Further, to unlock the locked state of the spring-integrated cover 60 at respective one of the foreside position CF, the intermediate position CC and the rear side position CR, the claw pressing section 663 is pushed in toward the back side in the thickness direction X (cutter body 2 side). Due to this, the lock claw section 662 is correspondingly detached from the foreside connecting concave section 464, the intermediate connecting concave section 465, or the rear side connecting concave section 466. Then, the spring-integrated cover 60 is moved among the foreside position CF, the intermediate position CC, and the rear side position CR by sliding the spring-integrated cover 60 in the longitudinal direction Y.

Further, to detach the spring-integrated cover 60 from the cutter body 2 by moving the spring-integrated cover 60 further forward from the foreside position CF with respect to the main body block 4, the releasing part pressing section 672 is pushed in toward the back side in the thickness direction X (cutter body 2 side). Due to this, the stopper releasing part 67 is detached from the releasing part connecting concave section 467 of the main body block 4. Further, the spring-integrated cover 60 is detached from the cutter body 2 (main body block 4) by sliding the spring-integrated cover 60 forward from this state.

The others are similar to those of the sixth embodiment.

In the case of the present embodiment, in the attached state S, user's safety can be ensured, and damage to the replaceable blade 3 can be prevented by locking the spring-integrated cover 60 at the foreside position CF. Further, the spring-integrated cover 60 includes the flat spring section 661 and the lock claw 662, and the main body block 4 includes the foreside connecting concave section 464, the rear side connecting concave section 466, and the intermediate connecting concave section 465. Due to this, the spring-integrated cover 60 can easily and surely be fixed to the cutter body 2 at one of the foreside position CF, the intermediate position CC, and the rear side position CR. Further, the spring-integrated cover 60 is configured such that the cover main body 65, the flat spring section 661 and the lock claw 662 are integrally formed by one metal plate. Thus, the number of components can be reduced, and cost of the cutter 1 can be reduced.

Further, the spring-integrated cover 60 includes the stopper releasing part 67. Due to this, when the spring-integrated cover 60 is locked at the intermediate position CC, the stopper function of the flat spring stopper 59 is automatically released. Thus, in this state, the slide block 5 can be moved forward with respect to the main body block 4, and the replaceable blade 3 can be replaced easily.

Other advantageous effects are identical to those of the sixth embodiment.

The invention claimed is:

1. A cutter formed by detachably attaching a replaceable blade to a cutter body, wherein
the replaceable blade has flexibility in a thickness direction,
the cutter body is composed of a main body block and a slide block retained in the main body block so as to be able to move in a longitudinal direction of the cutter,
the main body block includes a main body supporting section that supports a back face of the replaceable blade, and a main body connecting section that connects with the replaceable blade from a front face side,
the slide block includes a rear-side supporting section that supports the back face of the replaceable blade at a farther rear side from the main body supporting section, a slide connecting section that connects with the replaceable blade so as to retract the replaceable blade toward the rear side, and a back side protruding section that protrudes on a back side in the thickness direction, and
in an attached state in which the replaceable blade is attached to the cutter body, the replaceable blade is elastically deformed to curve in the thickness direction, the slide block is pressed toward the back side in the thickness direction by an elastic force of the replaceable blade, and the back side protruding section is engaged with an engaged section provided in the main body block.

2. The cutter according to claim 1, wherein
in the attached state, the rear-side supporting section protrudes farther than the main body supporting section toward a front side in the thickness direction.

3. The cutter according to claim 1, comprising:
a cylindrical dual-purposed stopper/cover mounted to the main body block so as to be slidable in the longitudinal direction and opened at both ends in the longitudinal direction, wherein
the dual-purposed stopper/cover is capable of being locked at three positions including a foreside position in which the replaceable blade is covered, a rear-side position in which the replaceable blade is significantly exposed, and an intermediate position between the foreside position and the rear-side position, and
the dual-purposed stopper/cover restricts a movement of the slide block with respect to the main body block when it is locked at the rear-side position.

4. The cutter according to claim 3, wherein
the dual-purposed stopper/cover includes a heightwise flat spring at one end in a height direction which is perpendicular to the longitudinal direction and the thickness direction, and a claw section at a free end of the heightwise flat spring, the heightwise flat spring being biased toward an opposite side from the main body block, and the claw section being formed toward an inner side in the thickness direction,
the main body block includes a slide groove section, formed in the longitudinal direction and a foreside connecting groove, an intermediate connecting groove, and a rear-side connecting groove respectively formed toward an outer side in the height direction from the slide groove section at three positions in the longitudinal direction, and
the claw section is slidably arranged in the slide groove section, and the dual-purposed stopper/cover can be locked at the foreside position, the intermediate position, or the rear-side position by connecting the claw section with the foreside connecting groove, the intermediate connecting groove, or the rear-side connecting groove, respectively.

5. The cutter according to claim 1, wherein
a thicknesswise flat spring biased toward the thickness direction is fixed to the slide block, the thicknesswise flat spring being elevated toward an outer side in the thickness direction, an elevation of which increases from a rear end side toward a fore end side, and in the attached state, a fore end section of the thicknesswise flat spring contacts with a contacted section provided in the main body block so that the slide block is prevented from moving forward with respect to the main body block.

6. The cutter according to claim 1, wherein a flat spring stopper capable of elastically deforming in the thickness direction is fixed to the slide block, the flat spring stopper includes a stopper protruding part that protrudes in a height direction perpendicular to the longitudinal direction and the thickness direction, and in the attached state, the stopper protruding part contacts with a stopper connection section provided in the main body block so that the slide block is prevented from moving forward with respect to the main body block.

7. The cutter according to claim 6, wherein the flat spring stopper includes a back side connecting part capable of deforming in the height direction, and the rear side connecting part is capable of being connected with a thicknesswise connecting part provided in the main body block from a back face side.

8. The cutter according to claim 6, comprising:

a spring-integrated cover including a cylindrical cover main body mounted with respect to the main body block so as to be slidable in the longitudinal direction and opened at both ends in the longitudinal direction, a flat spring section extending in the longitudinal direction and capable of elastically deforming in the thickness direction, and a lock claw provided at a movable end of the flat spring section, the cover main body, the flat spring section, and lock claw being integrally formed by one metal plate, wherein the main body block includes a foreside connecting concave section, a rear-side connecting concave section, and an intermediate connecting concave section, respectively concaved in the thickness direction at three positions in the longitudinal direction, and the spring-integrated cover is capable of being locked at a foreside position in which the replaceable blade is covered, a rear-side position in which the replaceable blade is significantly exposed, and an intermediate position between the foreside position and the rear-side position by connecting the lock claw with the foreside connecting concave section, the rear-side connecting concave section, or the intermediate connecting concave section, respectively.

9. The cutter according to claim 8, wherein the spring-integrated cover includes a stopper releasing part that presses the flat spring stopper, in a state the cover being locked at the intermediate position with respect to the main body block, to elastically deform the flat spring stopper in the thickness direction so that the stopper protruding part disconnects from the stopper connecting section.

10. The cutter according to claim 1, wherein the replaceable blade includes an opening section that penetrates the replaceable blade in the thickness direction, the main body connecting section protrudes on a foreside in the thickness direction from the main body supporting section, and is inserted in the opening section to make contact with a fore end of the opening section in the attached state, and the slide connecting section protrudes on the foreside in the thickness direction from the rear-side supporting section, and is inserted in the opening section to make contact with a rear end of the opening section in the attached state.

11. The cutter according to claim 10, wherein one of the slide block and the main body block includes a heightwise elastic member biased toward an opposing side in a height direction perpendicular to the longitudinal direction and the thickness direction, in using the blade, the replaceable blade is configured to be supported at three points including a lower face of the slide connecting section, an upper face of a rear end section of the main body connecting section and a lower face of a fore end section of the main body connecting section at the opening section by the slide block being pressed toward a lower side with respect to the main body block by a biasing force of the heightwise elastic member and the slide connecting section pressing the rear end section of the opening section toward the lower side, and the lower side is a side in the height direction on which a blade edge of the replaceable blade is formed, and the upper side is an opposite side from the lower side.

12. The cutter according to claim 10, wherein one of the main body block and the slide block on which the heightwise elastic member is not formed includes a foreside pressure-contact section that is capable of making a pressurized contact with the heightwise elastic member in the height direction in a blade replacing state in which the slide block is moved forward with respect to the main body block, and the movement of the slide block with respect to the main body block is restricted by the heightwise elastic member making a pressurized contact with the foreside pressure-contact section.

13. The cutter according to claim 1, wherein the slide block includes a rear-side opposing face that opposes a rear end of the replaceable blade in the longitudinal direction, and the rear-side opposing face presses the replaceable blade toward a foreside by the rear-side opposing face making contact with the rear end of the replaceable blade when the slide block is moved forward with respect to the main body block.

14. The cutter according to claim 13, wherein the slide block is diverged into a center part and a pair of diverged parts at a position on a foreside than the back side protruding section, the center part including the rear-side supporting section and the slide connecting section and the pair of diverged parts being arranged at both sides of the center part in a height direction perpendicular to the longitudinal direction and the thickness direction, and the rear-side opposing face is formed at fore ends of the pair of diverged parts.

* * * * *